(12) United States Patent
Gammelsaeter et al.

(10) Patent No.: US 8,557,295 B2
(45) Date of Patent: *Oct. 15, 2013

(54) USE OF CELLULAR EXTRACTS FOR SKIN REJUVENATION

(75) Inventors: Runhild Gammelsaeter, Oslo (NO); Jan Remmereit, Volda (NO)

(73) Assignee: Regenics AS, Oslo (NO)

( * ) Notice: Subject to any disclaimer, the term of this patent is extended or adjusted under 35 U.S.C. 154(b) by 4 days.

This patent is subject to a terminal disclaimer.

(21) Appl. No.: 13/101,445

(22) Filed: May 5, 2011

(65) Prior Publication Data

US 2012/0107412 A1    May 3, 2012

Related U.S. Application Data

(63) Continuation-in-part of application No. 12/437,100, filed on May 7, 2009, and a continuation-in-part of application No. 11/801,778, filed on May 11, 2007, now Pat. No. 8,075,920.

(60) Provisional application No. 61/332,047, filed on May 6, 2010, provisional application No. 61/051,931, filed on May 9, 2008, provisional application No. 61/120,146, filed on Dec. 5, 2008, provisional application No. 60/799,560, filed on May 11, 2006.

(51) Int. Cl.
  *A61K 35/60* (2006.01)
  *A61K 35/12* (2006.01)
  *A61K 35/52* (2006.01)
  *A61K 35/54* (2006.01)
  *C12N 5/00* (2006.01)
  *C12N 5/02* (2006.01)

(52) U.S. Cl.
  USPC ........... 424/523; 424/520; 424/561; 435/325; 435/375; 514/18.6

(58) Field of Classification Search
  None
  See application file for complete search history.

(56) References Cited

U.S. PATENT DOCUMENTS

| | | |
|---|---|---|
| 3,852,489 A | 12/1974 | Yip |
| 5,061,620 A | 10/1991 | Tsukamoto et al. |
| 5,166,065 A | 11/1992 | Williams et al. |
| 5,197,985 A | 3/1993 | Caplan et al. |
| 5,226,914 A | 7/1993 | Caplan et al. |
| 5,340,740 A | 8/1994 | Petitte et al. |
| 5,453,357 A | 9/1995 | Hogan et al. |
| 5,486,359 A | 1/1996 | Caplan et al. |
| 5,523,226 A | 6/1996 | Wheeler et al. |
| 5,589,376 A | 12/1996 | Anderson et al. |
| 5,591,625 A | 1/1997 | Gerson et al. |
| 5,651,992 A | 7/1997 | Wangh et al. |
| 5,654,183 A | 8/1997 | Anderson et al. |
| 5,672,499 A | 9/1997 | Anderson et al. |
| 5,716,827 A | 2/1998 | Tsukamoto et al. |
| 5,750,376 A | 5/1998 | Weiss et al. |
| 5,750,397 A | 5/1998 | Tsukamoto et al. |
| 5,843,780 A | 12/1998 | Thomson et al. |
| 5,849,553 A | 12/1998 | Anderson et al. |
| 5,968,829 A | 10/1999 | Carpenter et al. |
| 5,985,333 A | 11/1999 | Vainberg |
| 6,177,550 B1 | 1/2001 | Meyer et al. |
| 6,200,806 B1 | 3/2001 | Thomson et al. |
| 6,673,603 B2 | 1/2004 | Baetge et al. |
| 2002/0142397 A1 | 10/2002 | Collas et al. |
| 2003/0046722 A1 | 3/2003 | Collas et al. |
| 2004/0072288 A1 | 4/2004 | Collas et al. |
| 2005/0014258 A1 | 1/2005 | Collas et al. |
| 2005/0214257 A1 | 9/2005 | Zhao et al. |
| 2005/0260181 A1 | 11/2005 | Girsh |
| 2005/0271751 A1 | 12/2005 | Perrier et al. |
| 2006/0014282 A1 | 1/2006 | Fortunel et al. |
| 2006/0212952 A1 | 9/2006 | Collas et al. |
| 2007/0134792 A1 | 6/2007 | Dai et al. |
| 2009/0017147 A1* | 1/2009 | Lintner et al. ................ 424/780 |
| 2009/0069213 A1* | 3/2009 | Avila et al. ........................ 514/2 |

FOREIGN PATENT DOCUMENTS

| | | |
|---|---|---|
| CN | 1343496 | 4/2002 |
| DE | 2129212 A | 6/1971 |
| DE | 19917532 | 10/2000 |
| DE | 10001740 | 7/2001 |
| EP | 10600501 | 4/2005 |
| EP | 1629830 | 3/2006 |
| FR | 2096704 | 2/1972 |
| FR | 2500305 | 8/1982 |
| FR | 2827171 | 1/2003 |
| FR | 2843123 | 2/2004 |
| FR | 2096704 | 8/2007 |
| JP | 08169837 | 7/1996 |
| KR | 20030075297 | 4/2003 |
| RU | 2032398 | 4/1995 |
| RU | 2110984 | 5/1998 |

(Continued)

OTHER PUBLICATIONS

Liu et al 2009, Eur Food Res Technol, 228:411-416.*
Martin, "Wound Healing Aiming for Perfect Skin Regeneration," Science (1997) 276:75-81.
EP Office Communication dated Oct. 23, 2012 from related EP Patent Application No. 09 742 464.2-2107.

(Continued)

*Primary Examiner* — Valarie Bertoglio
(74) *Attorney, Agent, or Firm* — Casimir Jones SC

(57) ABSTRACT

The invention describes methods and agents for improving cosmetic appearance, for promoting, improving or restoring health of cells and tissues, preferably skin, and more preferably, for restoring aged or damaged skin to a healthy appearance. In preferred embodiments, the methods and agents comprise active extracts produced from fish eggs. The invention further provides processes for making active fish egg extracts.

26 Claims, 14 Drawing Sheets

(56) References Cited

FOREIGN PATENT DOCUMENTS

| | | |
|---|---|---|
| RU | 2232587 | 7/2004 |
| WO | 8907425 | 8/1989 |
| WO | 9222584 | 12/1992 |
| WO | 0189540 | 11/2001 |
| WO | 0218441 | 3/2002 |
| WO | 20040084828 | 10/2004 |
| WO | 2005099758 | 10/2005 |
| WO | 2008/020329 | 2/2008 |
| WO | 2009/136291 | 11/2009 |

OTHER PUBLICATIONS

Zoonoses of fish, amphibians and reptiles; http://www.apsu.edu/files/iacuc/Zoonoses-fish-reptiles-amphibians.pdf, website created on Feb. 12, 2007.

Dermatologische Rezepturen, Leitilinie der GD Gesellschaft Dermopharmazie e.V, Mar. 18, 2008, http://www.gd-online.de/german/veranstalt/images2008/GD_Leitilinie_Dermatologische_Rezepturen_18.3.2008.pdf.

Damian, Nutrition for Healthy Skin 2011, Part 2, 119-128.

Kawada, 2009, Journal of Dermatology, 36:583-586.

International Search Report and Written Opinion mailed May 3, 2012, PCT/IB2011/001488.

Anonymous: "Surgeon Caviar Extract", Internet Citation, Jan. 30, 2008, p. 1, retrieved from Internet: URL: http://www.magiray.info/id85.html, retrieved on May 10, 2010.

Database gnpd (online) mintel: Mar. 2010, "28 ultra intensive whitening kit," database accession No. 1295041.

Petsina A N et al., "Anti-aging face cream composition—comprises whole, homogenized sea urchin, mussel or salmon gonads, sea buckthorn, aloe and propolis extracts and polyethylene oxide gel," WPI / Thomson, vol. 1998, No. 50 May 20, 1998 (abstract).

Database gnpd (online) mintel; Nov. 2009 "gold caviar uv white," database accession No. 1202882.

Database gnpd (online) mintel; Dec. 2007, "luxurious travel set", database accession No. 822659'.

Database gnpd (online) mintel; Mar. 2004 "original hi-malt drink," database accession No. 260116.

Amoh et al., "Multipotent nestin-positive, keratin-negative hair follicle bulge stem cells can form neurons," PNAS, 2005, 102:5530-5534.

Bledsoe et al., "Caviars and Fish Roe Products," Critical Reviews in Food Science and Nutrition, 2003, 43:317-356.

Bradley et al., "Formation of germ-line chimeras from embryo-derived teratocarcinoma cell lines," Nature, 1994, 309:255-256.

Doetschmanet al., "Establishment of Hamster Blastocyst-Derived Embryonic Stem (ES) Cells," Dev Biol, 1988, 127:224-227.

English Translation of Abstract; Publication No. FR2500305; Published: Aug. 27, 1982; Applicant: Alvaro Mancori; (1 pg.).

English Translation of Abstract; Publication No. CN1343496; Published: Apr. 10, 2002; Applicant: Shenyang Farmacology University; (1 pg.).

English Translation of Abstract; Publication No. FR2827171 (A1); Published: Jan. 17, 2003; Applicant: SOC Extraction Principes Actif; (1 pg.).

English Translation of Abstract; Publication No. FR2843123 (A1); Published: Feb. 6, 2004; Applicant: Saint Laurent Parfums, et al.; (2 pgs.).

English Translation of Abstract; Publication No. RU2232587 (C1); Published: Jul. 20, 2004; Applicant: Mirra-M Stock Co.; (2 pgs.).

English Translation of Abstract; Publication No. JP08169837; Published: Jul. 2, 1996; Applicant: Shimizu Elko; (1 pg.).

English Translation of Abstract; Publication No. RU2110984 (C1); Published: May 20, 1998; Applicant: Biocomestic Wks Stock Co.; (1 pg.).

English Translation of Abstract; Publication No. DE199117532 (A1); Published: Oct. 26, 2000; Applicant: Christian Toloczyki; (1 pg.).

English Translation of Abstract; Publication No. DE10001740 (A1); Published: Jul. 26, 2001; Applicant: Jeannette Backhaus; (1 pg.).

English Translation; Publication No. FR2096704 (corresponding application to DE2129212), Aug. 30, 2007.

Evans et al., "Establishment in culture of pluripotential cells from mouse embryos," Nature, 1981, 292:154-156.

Evans et al., "Derivation and Preliminary Characterization of Pluripotent Cell Lines From Porcine and Bovine Blastocysts," Theriogenology, 1990, 33:125-128.

Giles et al., "Pluirpotency of Cultured Rabbit Inner Cell Mass Cells Detected by Isozyme Analysis and Eye Pigmentation of Fetuses Following Injection Into Blastocysts or Morulae," Mol. Reprod. Dev., 1993, 36:130-138.

Goldman et al., "Stem and progenitor cell-based therapy of the human central nervous system," Nat Biotechnol., 2005, 23:862-71.

Gottschalck, et al.; "International Cosmetic Ingredient Dictionary and Handbook"; The Cosmetic, Toiletry and Fragrance Association, Washington, D.C., (2004); 10th Edition, vol. 3; pp. 2041-2042.

Graves et al., "Derivation and Characterization of Putative Pluripotential Embryonic Stem Cells From Preimplantation Rabbit Embryos," Mol. Reprod. Dev., 1993, 36:424-433.

Iannaccone et al., "Pluripotent Embryonic Stem Cells from the Rat Are Capable of Producing Chimeras," Dev. Biol., 1994, 163:288-292.

Irie and Seki, "Retinoid composition and retinal localization in the eggs of teleost fishes," Comparative Biochemistry and Physiology Part B, 2002, 131:209-219.

Jack et al., "Processed lipoaspirate cells for tissue engineering of the lower urinary tract: implications for the treatment of stress urinary incontinence and bladder reconstruction," J Urol., 2005, 174:2041-5.

Kitmaura et al., "Establishment of renal stem/progenitor-like cell line from S3 segment of proximal tubules in adult rat kidney," Kidney Int., 2005, 68:1966.

Kocher et al., "Neovascularization of ischemic myocardium by human bone-marrow-derived angioblasts prevents cardiomyocyte apoptosis, reduces remodeling and improves cardiac function," Nat. Med., 2001, 7:430-436.

Leri et al., "Repair of the damaged heart," Kidney Int., 2005, 68:1962.

Levy et al., "Embryonic and adult stem cells as a source for cell therapy in Parkinson's disease," J Mol Neurosci, 2004, 24:353-86.

Li and, Gui, "Comparative studies on in vitro sperm decondensation and pronucleus formation in egg extracts between gynogenetic and bisexual fish," Cell Research, 2003, 13:159-169.

Martin et al., "Isolation of pluripotent cell line from early mouse embryos cultured in medium conditioned by teratocarcinoma stem cells," PNAS, 1981, 78:7634-7638.

Matzinger, "The Danger Model: A Renewed Sense of Self," Science, 2002, 296:301-305.

Menard et al., "Transplantation of cardiac-committed mouse embryonic stem cells to infarcted sheep myocardium: a preclinical study," Lancet, 2005, 366:1005-12.

Notarianni et al., "Maintenance and differentiation in culture of pluripotential embryonic cell lines from pig blastocysts," J. Reprod. Fertil., 1990, 41(Suppl.):51-56.

Sukoyan et al., "Isolation and Cultivation of Blastocyst-Derived Stem Cell Lines from American Mink (*Mustela vison*)," Mol. Reprod. Dev., 1992, 33:418-431.

Sukoyan et al., "Embryonic Stem Cells Derived From Morulae, Inner Cell Mass, and Blastocysts of Mink: Comparisons of Their Pluripotencies," Mol. Reprod. Dev., 1993, 36:148-158.

Taranger et al., "Induction of Dedifferentiation, Genome-wide Transcriptional Programming, and Epigenetic Reprogramming by Extracts of Carcinoma and Embryonic Stem Cells," Mol Biol Cell, 2005, 16:5719-5735.

Wener Baltes: "Lebensmittelchemie," Springer Verlag, Berlin, 4th ed., 1995, p. 295.

\* cited by examiner

* = p<0,05
** = p<0,01

USE OF CELLULAR EXTRACTS FOR SKIN REJUVENATION

This application claims the benefit of U.S. Prov. Appl. 61/332,047, filed May 6, 2010; and is a continuation-in-part of U.S. application Ser. No. 12/437,100, filed May 7, 2009, which claims the benefit of U.S. Prov. Appl. 61/051,931 filed May 9, 2008 and U.S. Prov. Appl. 61/120,146 filed Dec. 5, 2008; and is a continuation in part of U.S. application Ser. No. 11/801,778, filed May 11, 2007, allowed as U.S. Pat. No. 8,075,920 on Dec. 13, 2010, which claims the benefit U.S. Prov. Appl. 60/799,560, filed May 11, 2006, of all of which are incorporated herein by reference in their entirety.

FIELD OF THE INVENTION

This invention relates to the use of compositions comprising differentiable cells, egg cellular extracts or differentiable cell cellular extracts to prevent deterioration, damage and malfunction of cells and tissues, and to promote, improve and exceed cellular function in order to promote, improve and exceed appearance, vitality and health of cells and tissues, especially skin.

BACKGROUND OF THE INVENTION

Skin is the first barrier we have against outside aggressions, and carries out both physical and chemical defenses. Vitamin D is produced in the epidermis under the effects of solar radiation. This vitamin is necessary for calcium to be absorbed in the intestine and then fixed on the bones, which enables the development and growth of the human body. However, excessive sun exposure leads to skin damage and potentially cancer. In addition, skin cells may become damaged by physical means, i.e., wounded, or damaged due to age. In addition, aging decreases the activity of skin cells, especially fibroblasts, and the secretion of collagen from fibroblast. Thus, there is a need to identify compositions and methods for managing and improving skin health and preventing and treating skin conditions, and diseases, and maintaining normal skin appearance and restoring aged skin to a youthful appearance.

SUMMARY OF THE INVENTION

The invention relates to improving visible parts of a person contributing to cosmetic appearance directly or indirectly, including but not limited to skin, and to improve health and damage of cells and tissues preferably skin, and more preferably restoring aged skin to a youthful appearance. In some embodiments, the invention relates to compositions of cells, cell or egg extracts, and extract components which can induce de-differentiation, including but not limited to purified or synthetic nucleic acid sequences, polypeptides, or natural products contained in the extracts. In some embodiments, the cells are differentiable cells, preferably stem cells. In some embodiments, the compositions are used in a method that comprises application of the compositions to skin and/or wounds after removal the outer surface layers. In some embodiments, the invention relates to a method of de-differentiation of cells and/or de-differentiation followed by re-differentiation. In some embodiments, the invention relates to managing, preventing, and treating skin diseases. In some embodiments, the invention relates to a composition comprising i) a cellular component comprising differentiable cells, differentiable cell cellular extracts, egg cellular extracts or components of differentiable cell extracts or egg cellular extracts or combinations thereof and ii) lipids. In further embodiments, the composition further comprises purified or synthetic nucleic acid sequences, proteins, epigenetic inhibitors, or natural products contained in the extracts or combinations thereof. In further embodiments, the differentiable cells are embryonic stem cells, embryonic germ cells, or adult stem cells. The present invention is not limited to the use of any particular cellular extract or fraction. Indeed, the use of a variety of cellular extracts and fractions is contemplated, including, but not limited to, cytoplasmic extracts and fractions, nuclear extracts and fractions, water soluble extracts and fractions, and extracts and fractions prepared from cellular extracts by affinity chromatography, gradient centrifugation, HPLC, size exclusion chromatography and the like.

In some embodiments, the invention provides methods and the compositions find use for prevention of deterioration, damage and malfunction of cells and tissues, and to promote, improve and exceed cellular function in order to promote, improve and exceed appearance, vitality and health of cells and tissues.

In some embodiments, the lipid component is from a source other than the source of the extract, e.g., a purified lipid from a different source, either natural or synthetic. In further embodiments, the lipid component is derived from egg from fish, shrimp, sea urchin or frog and/or fish roe. In further embodiments, the lipid component contains cholesterol, fatty acids, and ceramides. In some embodiments, the lipid component is from a source different than the cellular component. In further embodiment, the composition contains keratin or flaggrin. In further embodiments, the composition further comprises glutamine, antiinfective agents, antioxidants and/or nicotinamide. In further embodiments, the antioxidant is vitamin E, A, or C or combinations thereof.

In some embodiments the invention provides a kit for improving the appearance of a scar comprising two compositions, wherein the first composition dissolves scar tissue and comprises collagen dissolving agents and the second composition improves wound healing and comprises a cellular component selected from the group consisting of differentiable cells, differentiable cell cellular extracts and an egg cellular extract or combinations thereof, lipids, proteins, and water. In further embodiments, the first composition further comprises an antiseptic compound, an antibacterial compound, an anti-inflammatory compound, an immunomodulator, a protease, or an analgesics or combinations thereof. In further embodiments, the second composition further comprises natural vernix, vernix extracts, vernix made from synthetic substances, and components of vernix extracts. In further embodiments the lipid component comprises squalene, aliphatic waxes, sterol esters, diol esters, triglycerides, free sterols, or combinations thereof. In further embodiments, the lipids and/or proteins are derived from eggs from fish, shrimp, sea urchin or frog and/or fish roe. In further embodiments, the lipid fraction contains cholesterol, fatty acids, or ceramides or a combination thereof. In some embodiments, the lipid component is from a different source than the cellular component. In further embodiments, the composition further comprises glutamine, antiinfective agents, antioxidants and/or nicotinamide.

In some embodiments, the invention provides methods for improving the appearance of a skin comprising: i) removing skin tissue by chemicals, a laser, or physical force and ii) applying a composition that improves wound healing comprising differentiable cells, differentiable cell or egg cellular extracts, components of differentiable cell extracts, lipids, proteins, and/or water. In further embodiments, improving the appearance of skin includes improving the appearance of a scar or improving the appearance of skin with wrinkles. In further embodiments, the differentiable cells are embryonic stem cells, embryonic germ cells, or adult stem cells. In further embodiments, the composition further comprises natural vernix, vernix extracts, vernix made from synthetic substances, and components of vernix extracts.

In additional embodiments, the invention provides methods for the topical administration of differentiable cells, egg or differentiable cell cellular extracts, components of cell extracts comprising: providing a composition comprising a cellular component comprising differentiable cells, egg or differentiable cell cellular extracts, components of cell extracts and a subject having skin and applying the extracts to the skin of the subject. In further embodiments, the egg or differentiable cellular extracts or components of cell extracts are effective as a nutrient to a cell of the skin. In further embodiments, the composition is a water-based gel. In further embodiments, the water-based gel comprises a compound selected from the group consisting of hyaluronic acid and chitosan. In further embodiments the composition is a component on a wound dressing. In further embodiments the composition is a component in a spray composition. In further embodiments the spray composition is an aerosol. In further embodiments, the spray composition dries on the skin. In further embodiments, the spray composition comprises gel-forming components. In some embodiments, the composition further comprises a lipid component as described above.

In some embodiments, the invention provides a wound healing dressing comprising a composition comprising differentiable cells, egg or differentiable cell cellular extracts, and components of cell extracts.

In additional embodiments, the invention provides methods for the topical administration of differentiable cells, cell extracts, components of cell extracts comprising: i) providing a) a composition containing differentiable cells, differentiable cell or egg cellular extracts, components of cell extracts, b) a subject having a wound in skin and c) wound dressing ii) applying the differentiable cells, cell extracts, components of cell extracts to the wound; and iii) covering the wound with the wound dressing. In further embodiments, the wound dressing is non-occlusive. In further embodiments, the wound dressing is plaster. In further embodiments, the wound dressing comprises: i) a waterproof layer; ii) a nutrient gel layer comprising differentiable cells, cell extracts, and components of cell extracts. In further embodiments, the waterproof layer is a polymeric (i.e., plastic) membrane that can be glued onto skin. In further embodiments, the nutrient gel layer comprises antibacterial agents and collagen modulating substances. In further embodiments, the nutrient gel layer improves the speed of wound healing.

In some embodiments, the invention provides methods for the topical administration of differentiable cells, egg or differentiable cell cellular extracts, or components of cell extracts comprising: i) providing a) a subject having 1) a wound in skin and 2) a tissue comprising specialized cells b) wound dressing; ii) harvesting the specialized cells from the tissue; iii) culturing the specialized cells under conditions such that a composition comprising the cultured specialized differentiable cells, cell extracts, or components of cell extracts is formed; iii) applying the composition to the wound; and iv) covering the wound with the wound dressing. In further embodiments, the specialized cells selected from the group consisting of a bulge hair-follicle stem cell, an embryonic stem, or germ stem cell. In further embodiments, the composition is a fluid suspension of specialized cells. In further embodiments, the composition is a plaster. In further embodiments, the composition is placed on a membrane with a nutrient gel layer prior to applying the composition to the wound. In further embodiments, the membrane is polymeric (i.e., plastic) functioning as an occlusive wound dressing when applied to the skin. In further embodiments, the wound dressing is a commercial band-aid. In further embodiments, prior to applying the composition a step of burning skin is performed, freezing skin is performed, and/or sanding skin is performed. In further embodiments, prior to applying the composition a transport vehicle which penetrate intact skin is applied to the composition or skin comprising a phospholipids, palmitylmyristrates, DMSO, polymer or chitosan suspensions or matrix, liposomes and/or trojan peptides, chariot peptides, small elastic vesicles (Van den Bergh et al., 1999), microspheres, nanoparticles, preloaded spherical beads, uni- and/or multilamellar vesicles, retinol molecular film, poly acrylo nitrile, beta-glucan (Redmond, Int. Journ. Cosmetic Science 2005), propylene glycol, butylenes glycol, polyethylene glycol, olive oil, dimethyl isosorbate, dimethylformamide, methyl salicylate, long chain oleic acids.

In some embodiments, the invention provides compositions for stimulating cells such as fibroblasts and keratinocytes comprising an effective amount of a purified cytoplasmic fraction of an embryonic stem cell, progenitor cell, somatic cell or eggs from animals, including but not limited to primates, rodents, fish, shrimp, sea urchin and/or frog egg. In further embodiments, the composition further comprises fats, proteins and/or natural products. In further embodiments, the composition further comprises an herbal substance. In further embodiments, the herbal substance is aloe vera. In further embodiments, the composition further comprises seed extracts. In further embodiments, the seed extracts are obtained from wheat, corn, rice, or avocado. In further embodiments, the composition further comprises a plant oil. In further embodiments, the composition further comprises a fungal substance. In further embodiments, the fungal substance is nepal fungus. In further embodiments, the composition further comprises fish, shrimp, sea urchin, or frog egg extracts, or components of these egg extracts. In further embodiments the components of egg extracts are glycosylation breakers and inhibitors. In further embodiments, the components of egg extracts are glycosylation breakers and inhibitors are aminoguanidine, carnosine, and fex pyridoxamine.

In additional embodiments, the invention provides methods of wound healing comprising providing a subject having a wound and a composition comprising differentiable cells, differentiable cell or egg cellular extracts, egg extracts, components of cell extracts or egg extracts and applying the composition to the wound under conditions such that the wound is healed. In further embodiments, the composition further comprises a collagen dissolving agent. In further embodiments, the collagen dissolving agent is an acid. In further embodiments, the composition further comprises a fruit acid. In further embodiments the composition is a cream. In further embodiments, the wound is an open wound and applying the composition topically. In preferred embodiments, the method further comprises providing a support matrix wherein, the support matrix comprises the composition. In further embodiments, the support matrix is a fabric or plastic wound dressing.

In some embodiments, the invention provides methods of skin regeneration comprising providing a subject having a wound and a composition comprising differentiable cells, differentiable cell or egg cellular extracts, or components of cell extracts or egg extracts and applying the composition to the wound under conditions that such skin is regenerated. In further embodiments the composition is a cream. In further embodiments, the wound is an open wound and the composition is applied topically.

In additional embodiments, the invention relates to a method of skin rejuvenation comprising providing a subject having an uneven skin and a composition comprising differentiable cells, differentiable cell or egg cellular extracts, egg extracts, or a component of a cellular extract and applying the composition to the uneven skin under conditions that such skin is rejuvenated. In some embodiments, the component of a cell extract is a nucleic acid sequence or the component of a cell extract is a peptide or combinations thereof. In some embodiments, the uneven skin is a result of a scar or wrinkles. In further embodiments, the composition is in a cream. In further embodiments the cream further comprises permeabilizing agents. In further embodiments, the permeabilizing agent is a non-toxic agent, DMSO or chitosan, chitosan polymer, or trypsin. In further embodiments, the permeabilizing agent is liposomes or alginate beads. In further embodiments, the liposomes or alginate beads comprise a peptide or a nucleic acid sequence of a cell extract or growth factor or a combination thereof. In further embodiments, the liposome comprises nucleic acid sequence of cell extracts or egg extracts generated by electroporation. In further embodiments, the composition comprises a fusion trojan peptide comprising a peptide of the cell extract. In further embodiments, the composition is applied topically. In additional embodiments, the method further comprises the step of applying the composition is executed after applying a chemical, laser, or physical force to the uneven skin under conditions that an outer lay of cells of the uneven skin are removed. In further embodiments, the composition further comprises an antiseptic compound, an antibacterial compound, an anti-inflammatory compound, an immunomodulator, a protease, or an analgesic compound or combinations thereof.

In some embodiments, the invention relates to a composition comprising: a lipid; a composition of plant seed components; an antioxidant; a purified or synthetic protein, or a purified or synthetic natural product contained in a cellular extract; a stabilizing component; autologous fat derived from adipose tissue of a subject.

In additional embodiments, the invention provides methods of improving a skin graft comprising grafting skin or skin substitute and applying a composition comprising: differentiable cells, differentiable cell or egg cellular extracts, egg extracts; components of cell extracts or egg extracts; a purified or synthetic nucleic acid sequence, a purified or synthetic protein, or a purified or synthetic natural product contain in cell extracts, egg extracts; or combinations thereof.

In some embodiments, the invention provides methods for managing, treating, and/or preventing scarring, abnormal scars, abnormal wound healing, widened scar, hypertrophied scar, keloid, keloid scar, wound-healing complications, cicatrix, and/or scar hypertrophy by administering in a prophylactic or non-prophylactic manner the compositions disclosed herein. In further embodiments, the invention provides methods for primary healing, wound closure, secondary healing, epithelialization, re-epithelialization, tertiary wound closure, delayed primary closure, debridement, and suture using the compositions described herein. In other embodiments, the compositions described herein are used to increase or decrease at the site of administration to a subject, inflammatory phase, proliferative phase, maturational phase, hemostasis, inflammation, collagen, clotting, thromboxane A2, prostaglandin 2a, prostaglandin 2-alpha, vasoconstrictor, hemorrhage, vasodilatation, histamine, platelet, chemokine, epidermal growth factor, fibronectin, fibrinogen, histamine, platelet derived growth factor, serotonin, von Willebrand factor, clot formation, platelet degranulation, complement cascade, neutrophil, leukocyte, macrophage, monocyte, collagenase, interleukin, tumor necrosis factor, fibroblasts, transforming growth factor, keratinocyte, angiogenesis, granulation tissue formation, collagen deposition, and insulin-like growth factor.

In some embodiments, the invention provides compositions comprising differentiable cells, preferably embryonic stem cells or precursor cells. In further embodiments, the compositions comprise the extracts of differentiable cells, preferably embryonic stem cells or precursor cells. In additional embodiments, the compositions contain components of extracts from differentiable cells, preferably embryonic stem cells or precursor cells.

In some embodiments, the invention provides compositions containing differentiable cells, preferably embryonic stem cells or precursor cells, the extracts of differentiable cells, preferably embryonic stem cells or precursor cells, components of extracts from differentiable cells, and/or natural vernix and/or vernix extracts and/or vernix components of vernix extracts that partially or totally synthetic.

In some embodiments, the invention provides methods for the topical administration of egg cellular extracts or differentiable cell cellular extracts comprising: providing a composition containing egg cellular extracts or differentiable cell cellular extracts and a subject having skin and applying the extracts to the skin. Preferably a nutritional signal in the extract reaches and is effective as a nutrient to the skin cells. Preferably the composition is in a water based gel comprising hyaluronic acid and/or chitosan. In another preferred embodiment, the extract is a spray acting as a liquid band-aid or fluid that dries on the skin. In further embodiments, the liquid contains gel-forming components such as collagen and chitosan. In further preferred embodiments, the composition is a component of a film on a support or cream.

The present invention also provides for use of the foregoing compositions for the treatment of skin, for removing wrinkles, for rejuvenation of skin, for wound healing, for improving the appearance of skin, the prevent damage to skin, to prevent deterioration of skin, or to provide nutrients to skin and any other use described herein.

The present invention further provides methods for preparing a composition for topical application to the skin comprising: providing differentiable cells or preparing an extract or fraction of differentiable cells or eggs; and formulating said differentiable cells or said extract with an agent for topical administration to the skin to provide a cream, gel, spray, emulsion, solid, plastic or matrix, ointment, powder or lotion suitable for topical administration. In further embodiments, the present invention provides compositions made by the foregoing methods.

In some embodiments, the present invention provides methods comprising: contacting the skin of said subject with a cellular extract in an amount effective to cause one or more effects selected from the group consisting of reduction of fine lines in the skin, normalization of skin color, increasing skin water content and hydration, decreasing or normalizing the amount of sebum in the skin, decreasing production of melanin, increasing collagen protein production, increasing collagen gene expression, increasing adult stem cell proliferation, increasing cellular metabolism of carbohydrates, increasing cellular metabolism of lipids, prevention of apoptosis, increasing angiogenesis, upregulation the cell cycle of cells, increasing angiogenesis, increasing the hair cycle, increasing follicular development, and increasing cell proliferation. In some embodiments, the effect is upregulation of a gene listed in Table 11 or regulation or upregulation of a pathway or effect listed in Table 11. In some embodiments, the present invention provides for the use of a cellular extract for one or more of reduction of fine lines in the skin, normalization of skin color, increasing skin water content and hydration, decreasing or normalizing the amount of sebum in the skin, decreasing production of melanin, increasing collagen protein production, increasing collagen gene expression, increasing adult stem cell proliferation, increasing cellular metabolism of carbohydrates, increasing cellular metabolism of lipids, prevention of apoptosis, increasing angiogenesis, upregulation the cell cycle of cells, increasing angiogenesis, increasing the hair cycle, increasing follicular development, and increasing cell proliferation. In some embodiments, the effect is upregulation of a gene listed in Table 11 or regulation or upregulation of a pathway or effect listed in Table 11. In some embodiments, the effect is on one or more types of cell-types associated with the skin. In some embodiments, the cell type associated with the skin is selected from the group consisting of a keratinocyte, fibroblast, melanocyte, and adipocyte.

In some embodiments, normalization of skin color comprises a reduction of skin erythema index. In some embodiments, the reduction in the skin melanin index or erythema index is measured by a skin analysis system, such as the Mexameter (MX18, Courage+Khazaka, Germany), using the protocol provided with the system. In some embodiments, the cellular extract comprises about 100 to 380 mg/ml protein in an aqueous solution; about 0.1 to 10 mg/ml RNA; about 0.1 to 5 mg/ml DNA and 0.1-10% lipids w/w; wherein said composition has an osmolarity of from about 330 to 440 mOsm, a pH of from about 5.0 to 7.7, and density of from about 0.8 to 1.4 g/ml. In some embodiments, the cellular extract is selected from the group consisting of an extract of an activated fish egg cellular extract and an unactivated fish egg cellular extract. In some embodiments, the fish egg cellular extract is from a fertilized egg. In some embodiments, the cellular extract is provided in a cream, gel, emulsion, ointment, spray, powder or lotion. In some embodiments, the cellular extract is a cytoplasmic extract.

In some embodiments, the present invention provides a composition comprising a cellular extract and an agent selected from the group consisting of Vitamin C and iron. In some embodiments, the cellular extract comprises about 100 to 380 mg/ml protein in an aqueous solution; about 0.1 to 10 mg/ml RNA; about 0.1 to 5 mg/ml DNA and 0.1-10 lipids w/w; wherein said composition has an osmolarity of from about 330 to 440 mOsm, a pH of from about 5.0 to 7.7, and density of from about 0.8 to 1.4 g/ml. In some embodiments, the cellular extract is selected from the group consisting of an extract of an activated fish egg cellular extract and an unactivated fish egg cellular extract. In some embodiments, the fish egg cellular extract is from a fertilized egg. In some embodiments, the cellular extract is provided in a cream, gel, emulsion, ointment, spray, powder or lotion. In some embodiments, the cellular extract is a cytoplasmic extract.

In some embodiments, the present invention provides processes comprising: treating fish eggs to reduce bacterial load; homogenizing said fish eggs by application of pressure to produce a fish egg homogenate; and separating an active fraction from said fish egg homogenate by centrifugation, wherein said active fraction comprises about 100 to 380 mg/ml protein in an aqueous solution; about 0.1 to 10 mg/ml RNA; about 0.1 to 5 mg/ml DNA and 0.1-10% lipids w/w. In some embodiments, the pressure is hydraulic pressure. In some embodiments, the pressure is about 5 to about 30 tons. In some embodiments, the centrifugation is continuous.

In some embodiments, the present invention provides a process for producing an active fish egg fraction comprising: milling the fish eggs between two surfaces, at least one of which is a milling surface, wherein the surfaces have a space there between so that said fish eggs are crushed when passed between the surfaces to provide a fish egg homogenate; and separating an active fraction from said fish egg homogenate, wherein said active fraction comprises about 100 to 380 mg/ml protein in an aqueous solution; about 0.1 to 10 mg/ml RNA; about 0.1 to 5 mg/ml DNA and 0.1-10% lipids w/w. In some embodiments, the milling surface comprising cutting elements. In some embodiments, the cutting elements comprise knurls. In some embodiments, the surfaces are cylindrical and rotate. In some embodiments, the surfaces are separated by about 0.1 to 2.0 mm. In some embodiments, the separating comprising centrifugal separation.

DESCRIPTION OF THE FIGURES

FIG. 1 using baseline 650 nm.

DEFINITIONS

Figure 1:
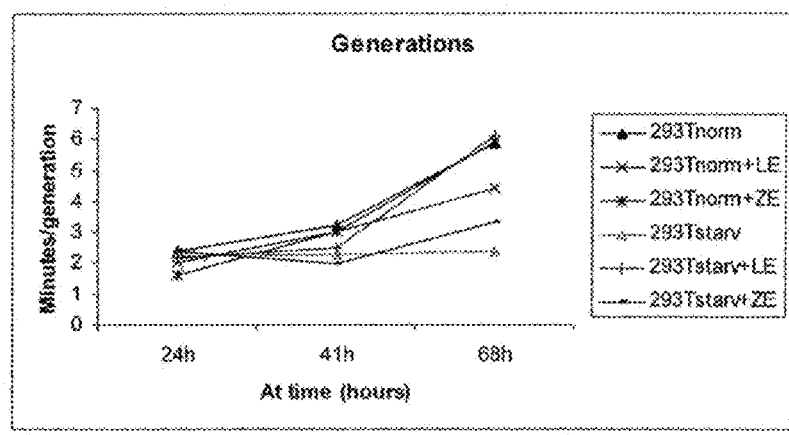
FIG. 1 is a graph of generations over time.
Figure 2:
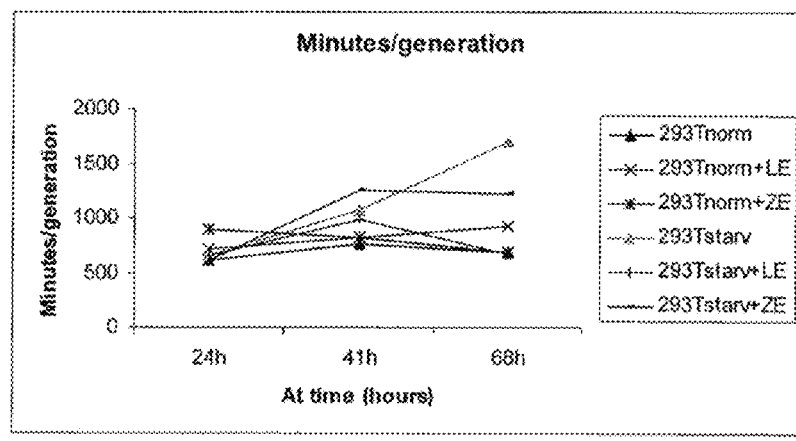
FIG. 2 is a graph of minutes/generation v. time.
Figure 3:
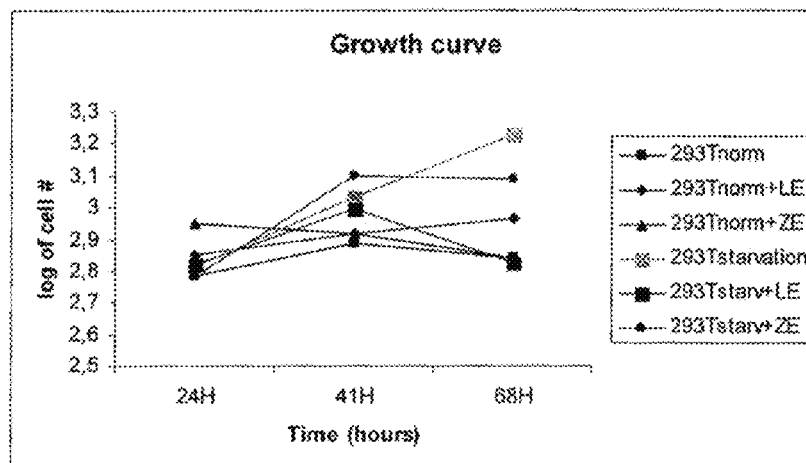
FIG. 3 is a growth curve graph.
Figure 4:
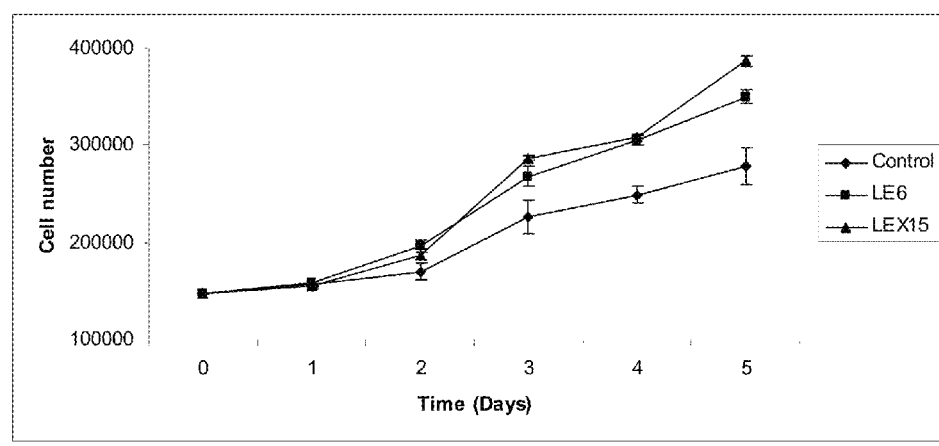
FIG. 4 provides a graph demonstrating the effect of LEX on proliferation of fibroblasts in vitro. Diamond—control, square—LEX6, triangle—LEX15.
Figure 5:
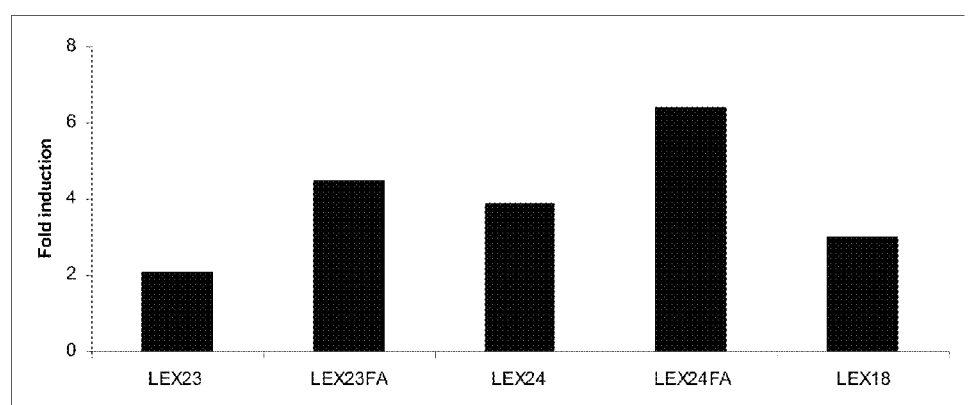
FIG. 5 provides a graph of the fold induction of trout roe, unfertilized salmon egg (salmon roe) and fertilized salmon egg (eyeroe) extracts.

"Anti-infective agents" include, but are not limited to benzylpenicillin, penicillin, penicillin G, 6-phenyl acetyl penicillin, penicillin V, micronomicin, clavulanate, oxacillin, dequalinium, cloxacillin, sulbenicillin, ampicillin, cilleral, and principen and combinations thereof.

"Anti-inflammatory" means a substance that reduces inflammation. Many analgesics remedy pain by reducing inflammation. Many steroids—specifically glucocorticoids—reduce inflammation by binding to cortisol receptors. Non-steroidal anti-inflammatory drugs (NSAIDs) alleviate pain by counteracting the cyclooxygenase (COX) enzyme. On its own COX enzyme synthesizes prostaglandins, creating inflammation. Many herbs have anti-inflammatory qualities, including but not limited to hyssop and willow bark (the latter of which contains salicylic acid, the active ingredient in aspirin), as well as birch, licorice, wild yam and ginseng.

"Antioxidants" means any of a variety of substances that prevent or slow the breakdown of another substance by oxygen. Synthetic and natural antioxidants are used to slow the deterioration of gasoline and rubber, and such antioxidants as vitamin C (ascorbic acid), butylated hydroxytoluene (BHT), and butylated hydroxyanisole (BHA) are typically added to foods to prevent them from becoming rancid or from discoloring. Nutrients such as beta-carotene (a vitamin A precursor), vitamin C, vitamin E, and selenium have been found to act as antioxidants. They act by scavenging free radicals, molecules with one or more unpaired electrons, which rapidly react with other molecules, starting chain reactions in a process called oxidation. Free radicals are a normal product of metabolism; the body produces its own antioxidants (e.g., the enzyme superoxide dismutase) to keep them in balance. However, stress, aging, and environmental sources such as polluted air and cigarette smoke can add to the number of free radicals in the body, creating an imbalance. The highly reactive free radicals can damage healthy DNA and have been linked to changes that accompany aging (such as age-related macular degeneration, a leading cause of blindness in older people) and with disease processes that lead to cancer, heart disease, and stroke.

An "antiseptic" is a substance that kills or prevents the growth and reproduction of various microorganisms, including bacteria, fungi, protozoa, and viruses on the external surfaces of the body. The objective of antiseptics is to reduce the possibility of sepsis, infection or putrefaction by germs. Antibacterials have the same objective but only act against bacteria. Antibiotics perform a similar function, preventing the growth or reproduction of bacteria within the body. Antiseptics include, but are not limited to, alcohol, iodine, hydrogen peroxide, and boric acid. There is great variation in the ability of antiseptics to destroy microorganisms and in their effect on living tissue. For example, mercuric chloride is a powerful antiseptic, but it irritates delicate tissue. In contrast, silver nitrate kills fewer germs but can be used on the delicate tissues of the eyes and throat. There is also a great difference in the time required for different antiseptics to work. Iodine, one of the fastest-working antiseptics, kills bacteria within 30 sec. Other antiseptics have slower, more residual action. Since so much variability exists, systems have been devised for measuring the action of an antiseptic against certain standards. The bacteriostatic action of an antiseptic compared to that of phenol (under the same conditions and against the same microorganism) is known as its phenol coefficient.

"Chitosan" is a beta-1,4-linked glucosamine polymer which, unlike chitin, contains few, if any, N-acetyl residues. It may be obtained from chitin, a polysaccharide found in the exoskeletons of crustaceans such as shrimp, lobster, and crabs. The shells may be ground into a pulverous powder. This powder is then deacetylated which allows the chitosan to absorb lipids.

"Collagen" means any of a variety of substances that contains the alpha chains of the collagen polypeptide with a sequence that generally follows the pattern Gly-X-Y, where Gly for glycine, X for proline, and Y for proline or hydroxyproline. Collagen proteins also contain significant amounts of glycine and proline. Hydroxyproline and hydroxylysine are not inserted directly by ribosomes. They are derivatised from proline and lysine in enzymatic processes of post-translational modification, for which vitamin C is required. This is related to why vitamin C deficiencies can cause scurvy, a disease that leads to loss of teeth and easy bruising caused by a reduction in strength of connective tissue due to, a lack of collagen, or defective collagen. Cells called fibroblasts form the various fibers in connective tissue in the body including collagen. The white collagen that makes up the matrix of most connective tissue in mammals consists of inter-woven fibres of the protein collagen. The collagen fibers consist of globular units of the collagen sub-unit, tropocollagen. Tropocollagen sub-units spontaneously arrange themselves under physiological conditions into staggered array structures stabilized by numerous hydrogen and covalent bonds. Tropocollagen sub-units are left-handed triple helices where each strand is, further, a right-handed helix itself. Thus, tropocollagen may be considered to be a coiled coil.

Although collagen is responsible for skin elasticity, and its degradation leads to wrinkles that accompany aging, it occurs in many other places throughout the body, and in different forms known as types: Type I collagen—This is the most abundant collagen of the human body present in scar tissue, the end product when tissue heals by repair; Type II collagen—Auricular cartilage Type III collagen—This is the collagen of granulation tissue, and is produced quickly by young fibroblasts before the tougher type I collagen is synthesized; Type IV collagen—Basal lamina; Type V collagen—most interstitial tissue, assoc. with type I; Type VI collagen—most interstitial tissue, assoc. with type I; Type VII collagen—epithelia; Type VIII collagen—some endothelial cells; Type IX collagen—cartilage, assoc. with type II; Type X collagen—hypertrophic and mineralizing cartilage; Type XI collagen—cartilage; Type XII collagen—interacts with types I and III.

With in the context of certain embodiments, "collagen modulating substances" means a variety of substances capable of facilitating the formation or breaking down of units or of any type of collagen.

A "gel" is a semisolid material formed from a colloidal solution. By weight, gels are mostly liquid, yet they behave like solids. An example is gelatin.

"Keratin" is any of a variety of fibrous protein molecules that serve as structural units for various living tissues. The keratins are the major protein components of hair, wool, nails, horn, hoofs, and the quills of feathers. These proteins generally contain large quantities of the sulfur-containing amino acids, particularly cysteine. The helical keratin molecules twist around each other to form elongated strands called intermediate filaments. The formation of a disulfide bridge between the sulfur atoms on two cysteines on separate polypeptide chains of keratin allows for the cross-linkage of these chains and results in a fairly rigid aggregate.

"Filaggrin" is any of a variety of filament-associated proteins that interact with keratin intermediate filaments of terminally differentiating mammalian epidermis via disulphide bond formation.

"Immunomodulator" means any of a variety of substance that influences the immune system. Examples include, but are not limited to, cytokines, Interleukin-2, immunostimulants, and immuno suppressors.

The term "natural product" means any of a variety of organic chemical moieties whose molecular arrangement is derived from enzymatic transformations in a living organism excluding amino acids, proteins, polypeptides, nucleic acids and sequences, and saturated fatty acids. Examples include, but are not limited to lipids (i.e., that are not saturated fatty acids), carbohydrates/saccharides and polysaccharides, the steroids and their derivatives, the terpenes and their derivatives, vitamins, carotenoids, and natural medicines such as taxol, etc. The term "synthetic natural product" is a natural product not obtained from its natural source.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside," as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

"Nucleic acid sequence" as used herein refers to an oligonucleotide, nucleotide or polynucleotide, and fragments or portions thereof, and to DNA or RNA of genomic or synthetic origin that may be single- or double-stranded, and represent the sense or antisense strand.

An "amino acid sequence" as used herein refers to a peptide or protein sequence.

A "peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al. (1993) Anticancer Drug Des., 8:53-63).

"Peptides", herein defined as polymers formed from the linking, in a defined order, of α-amino acids; including but not limited to milk peptides, ribosomal peptides, nonribosomal peptides, peptones and peptide fragments. Peptides are believed to have a good effect on skin and wrinkles. Because peptides are so small, it is thought that they may more easily penetrate the skin and yield their effects.

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

As used herein the term "portion" in reference to an amino acid sequence or a protein (as in "a portion of an amino acid sequence") refers to fragments of that protein. The fragments may range in size from four amino acid residues to the entire amino acid sequence minus one amino acid.

As used herein, the term "purified" refers to molecules, including but not limited to nucleic, ribonucleic, lipid or amino acid sequences, which are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

"Cancer" means any of various cellular diseases with malignant neoplasms characterized by the proliferation of anaplastic cells. It is not intended that the diseased cells must actually invade surrounding tissue and metastasize to new body sites. Cancer can involve any tissue of the body and have many different forms in each body area. Most cancers are named for the type of cell or organ in which they start.

"Cell" means the smallest structural unit of living matter capable of functioning autonomously, consisting of one or more nuclei, cytoplasm, and various organelles, all surrounded by a semipermeable membrane. Cells include all somatic cells obtained or derived from a living or deceased animal body at any stage of development as well as germ cells, including sperm and eggs (animal reproductive body consisting of an ovum or embryo together with nutritive and protective envelopes). Included are both general categories of cells: prokaryotes and eukaryotes. The cells contemplated for use in this invention include all types of cells from all organisms in all kingdoms: plans, animals, protists, fungi, archaebacteria and eubacteria. Stem cells are cells capable, by successive divisions, of producing specialized cells on many different levels. For example, hematopoietic stem cells produce both red blood cells and white blood cells. From conception until death, humans contain stem cells, but in adults their power to differentiate is reduced.

As used herein, the term "differentiation" related to cells means the process by which cells becomes structurally and functionally specialized, which is a progressive restriction of the developmental potential and increasing specialization of function which takes place during the development of the embryo and leads to the formation of specialized cells, tissues, and organs.

The term "dedifferentiation" related to cells means the reverse process of differentiation, where cells become less structurally and functionally specialized, which increases the developmental potential of the cell.

"Differentiable" means the ability of a cell to differentiate into a desired cell type. As used herein, the term "differentiates" means specialization (differentiation) or return to a more primitive cell type; dedifferentiation).

An "extract" as used in the context of "cell extract" and "egg extract" in this invention means a preparation of any type of cell as defined above obtained by chemical or mechanical action, as by pressure, distillation, evaporation etc. Extracts can include all or any single component or combination of components of the cells, including concentrated preparations of the active components. Such components of the extracts include but are not limited to RNA, DNA, lipids, all amino acid base structures including peptides and proteins, carbohydrates or combinations thereof. Extracts contemplated by this invention include but are not limited to extracts of fish eggs, urchin eggs, frog eggs, adult stem cells, plant seeds and plant stem cells.

"Growth media" are compositions used to grow microorganisms or cells in culture. There are different sorts of media for growing different sorts of cells. The biggest difference in growth media are between those used for growing cells in culture (cell culture uses specific cell types derived from plants or animals) and those used for growing microorganisms (usually bacteria or yeast). These differences arise due to the fact that cells derived from whole organisms and grown in culture are often incapable of growth without the provision of certain requirements, such as hormones or growth factors which usually occur in vivo. In the case of animal cells these requirements are often provided by the addition of blood serum to the medium. These media are often red or pink due to the inclusion of pH indicators. Growth media for embryonic stem cells preferably contains minimal essential medium, i.e., Eagle's: amino acids, salts (Ferric nitrate nonahydrate, Potassium chloride, Magnesium sulfate, Sodium chloride, Sodium dihydrogen phosphate), vitamins, (Ascorbic acid, Folic acid, Nicotinamide, Riboflavin, B-12) or Dulbecco's: additionally iron, glucose; non-essential amino acids, sodium pyruvate, β-mercaptoethanol, L-glutamine, fetal bovine serum and Leukemia Inhibitory Factor (LIF). In the case of microorganisms, there are no such limitations as they are often single cell organisms. One other major difference is that animal cells in culture are often grown on a flat surface to which they attach, and the medium is provided in a liquid form, which covers the cells. Bacteria such as *Escherichia coli* (*E. coli*, the most commonly used microbe in laboratories) may be grown on solid media or in liquid media, liquid nutrient medium is commonly called nutrient broth. The preferred growth media for microorganisms are nutrient broth or Luria-Bertani medium (L-B medium). Bacteria grown in liquid cultures often form colloidal suspensions. When agar (a substance which sets into a gel) is added to a liquid medium it can be poured into Petri dishes where it will solidify (these are called agar plates) and provide a solid medium on which microbes may be cultured.

Within the context of certain embodiments, "to glue to skin" means to stick or fasten to with or as if with any of various adhesives, such as, glue, paste or mucilage.

A "lipid" means any of a group of organic compounds, including the fats, oils, waxes, sterols, and triglycerides that are insoluble in water but soluble in nonpolar organic solvents, and are oily to the touch. Major classes of lipids include the fatty acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and long-chain alcohols and waxes. In living organisms lipids serve as the basis of cell membranes and as a form of fuel storage. Often lipids are found conjugated with proteins or carbohydrates, and the resulting substances are known as lipoproteins and lipopolysaccharides. The fat-soluble vitamins can be classified as lipids. Liposomes are spherical vesicles formed by mixing lipids with water or water solutions. They have found applications in the oral administration of some drugs (e.g., insulin and some cancer drugs), since they retain their integrity until they are broken down by the lipases in the stomach and small intestine.

Within the context of certain embodiment, a "nutrient gel layer" a gel comprising substances typically contained in a growth medium.

Within the context of certain embodiments, "specialized cell" of a subject means that the cell has characteristic immuno-identificative markers, such that differentiation of these cells and exposure to tissues of the subjects can be done under conditions such that immune system does not create antibodies to the differentiated cells. For example, when red blood cells carrying one or both A or B antigens are exposed to the corresponding antibodies, they agglutinate; that is, clump together. People usually have antibodies against those red cell antigens that they lack. Thus, specialized red blood cells of the subject would be those of the proper blood type. The cause of transplant rejection is recognition of foreign MHC antigens by T cells and activation of those T cells to become effector cytotoxic or helper T cells. T cell activation occurs in the case of vascularized grafts of nucleated cells expressing MHC Matching MHC Class I (especially HLA-B) and Class II HLA-DR alleles is more important for successful transplantation than matching other MHC antigens; and matching MHC is more important than matching minor histocompatibility antigens. Thus, specialized MHC presenting cells of the subject would be those presenting matching MHC alleles.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, the present invention also contemplates treatment that merely reduces symptoms, and/or delays disease progression.

Within the context of certain embodiments, a "waterproof layer" means a material or fabric that is substantially impervious to water or a layer of a sealing agent to intended to prevent substantial penetration by water.

As used herein, the term "transport vehicle" includes substances capable of aiding penetration of intact skin or skin cells or other somatic cells. The term "transport vehicle" is used synonymously with the term "permeabilizing agents". Such transport vehicles include, but are not limited to: phospholipids, palmitylmyristyrates, DMSO, polymer or chitosan suspensions or matrix, liposomes, Trojan peptides, chariot peptides, small elastic vesicles, microspheres (functionalized vectors made from naturally derived materials such as collagen, glycosaminoglycans, chondroitin sulfate, chitosan or polysaccharides), nanoparticles (carries lipophilic substances and enhance bioavailability of the encapsulated material into skin), preloaded spherical beads and sponges, uni- and/or multilamellar vesicles (stabilize contents of extracts in cream base and help transport into skin), retinol molecular film fluid (thin uniform monolayer film that facilitates the transfer of actives through the stratum corneum), poly acrylo nitrile (polymers comprising a controlled release system that synchronizes the release of an active ingredient along with a fragrance as a sensory marker which conveys the efficacy of the product), beta-glucan (oat fiber which aids in penetration of the skin, (Redmond, Int. Journ. Cosmetic science 2005), propylene glycol (as drug carrier, work best with a mineral oil based cream/lotion etc), butylene glycol, polyethylene glycol, olive oil, dimethyl isosorbide, dimethylformamide, methyl salicylate (these all enhance absorption through skin), long chain oleic acids (disrupts the bilayer within the stratum corneum, vital for permeation of compositions in propylene glycol-based formulations), substances capable of adjusting pH, hydration and local metabolism in skin. Agents modifying these factors include a vehicle containing an active hydrophobic agent, de-ionization of active ingredients, increased hydration of the skin (water content of carrier solution/cream/medium), lactic acid (alters the pH).

As used herein, the term "NANOG" refers to a homeobox gene. NANOG is thought to be required for stem cells to multiply without limit while remaining able to make many different types of cells. The gene is a potential master gene that helps make embryonic stem cells grow in the laboratory, making stem cells immortal.

As used herein, the term "OCT4" refers to a gene that is not active in somatic cells, including adult stem cells, but is expressed in embryonic stem and germ cells. OCT4 is essential to maintain pluripotency of embryonic stem cells.

As used herein, the term "SOX2" refers to the sex determining region Y (SRY) box 2 protein coding gene. This intronless gene encodes a member of the SRY-related HMG-box (SOX) family of transcription factors involved in the regulation of embryonic development and in the determination of cell fate.

As used herein, the term "GAPDH" refers to the housekeeping gene glyceraldehydes-3-phosphate dehydrogenase. This gene is involved in basic functions needed for cell maintenance. Housekeeping genes are constitutively expressed.

DETAILED DESCRIPTION OF THE INVENTION

The invention relates to improving health and damage of cells and tissues preferably skin, and more preferably restoring aged or damaged skin to a youthful and healthy appearance. In some embodiments, the invention relates to compositions of cells, cell or egg extracts, and extract components which can induce differentiation, including but not limited to purified or synthetic nucleic acid sequences, polypeptides, or natural products contained in said extracts. In some embodiments, the cells are differentiable cells, preferably stem cells or eggs. In some preferred embodiments, the extracts are aqueous extracts. In some embodiments, the extracts are from a non-avian source. In some embodiments, compositions are used in a method that comprises application of compositions to skin and/or wounds after removal the outer surface layers. In some embodiments, the invention related to a method of dedifferentiation of cells and/or dedifferentiation followed by redifferentiation. In some embodiments, the invention relates to managing, preventing, and treating skin diseases.

Application of the composition to the desired surface may be prophylactic, so that the composition is applied to the skin or other surface before exposure to an agent occurs. Application of the composition may be curative, for example, to further protect a compromised skin surface or to provide a protectant surface during natural or mediated healing of an exposed skin surface. Application of the composition may be protective, for example, to protect a skin surface should exposure to the agent Occur.

The present invention relates to the use of extracts or components of differentiable cells for topical application to surfaces of the body. Accordingly, the present invention provides methods and compositions for cosmetic and therapeutic uses. The present invention is not limited to the use of extracts or components of any particular type of differentiatable cell. Indeed, the use of variety of types of cells and differentiable cells from any organism is contemplated, including, but not limited to, mammalian embryonic stem cells, mammalian adult stem cells, cord blood cells, fish, shrimp or sea urchin eggs and embryos, and amphibian eggs and embryos.

In some embodiments, the invention relates to dedifferentiating existing epithelial/epidermal cells to a primordial state, wherein the cells have stem-cell capacities and can reform the correct and needed cells for the regeneration of the whole layer of skin (epidermis, dermis and subdermis). Although many differentiated cells are typically committed to their fate, dedifferentiation events can take place. Urodele amphibians and teleost fish can replace lost anatomical parts by a process of migration, dedifferentiation, proliferation and redifferentiation of epithelial cells in the wounded area. Functional reprogramming of differentiated cell nuclei has also been illustrated by the derivation of pluripotent embryonic stem cells (ESCs), and by the live birth of cloned animals after nuclear transplantation into unfertilized eggs.

The term plasticity, as used in this herein, means that a cell from one tissue can generate the differentiated cell types of another tissue. *Xenopus* eggs can reprogram mammalian somatic nuclei to express the POU family member homeodomain transcription factor gene Oct4 by a process requiring DNA demethylation. DNA demethylation also occurs after fusion of mouse thymocytes with embryonic germ cells (EGCs) but interestingly, only EG cells are capable of demethylating imprinted genes. Fusion of neuronal progenitor cells or bone marrow derived cells with ESCs results in hybrids which express markers of pluripotency. Similar results are obtained from fusing human fibroblasts with ESCs. Fusion of embryonal carcinoma cells (ESCs) with T-lymphoma cells also promotes the formation of colonies expressing pluripotent cell transcripts from the lymphoma genome. Components of pluripotent EG, ES or EC cells can elicit reprogramming events in a somatic genome.

Somatic nuclear function can be altered using nuclear and cytoplasmic extracts because extracts provide the necessary regulatory components. Extracts of regenerating newt limbs promote cell cycle reentry and downregulation of myogenic markers in differentiated myotubes. Teratocarcinomas are a particular type of germ cell tumors which contain undifferentiated stem cells and differentiated derivatives that can include endoderm, mesoderm and ectoderm germ layers. Undifferentiated carcinoma cells can be cultured to give rise to lines of ECCs. ECCs form malignant teratocarcinomas when transplanted into ectopic sites; however, some ECC lines can also contribute to tissues of the developing fetus when introduced into a blastocyst.

Undifferentiated human teratocarcinoma NCCIT cells can be established from a mediastinal mixed germ cell tumor. NCCIT is at a stage intermediate between a seminoma (a precursor of germ cell tumors) and an embryonal carcinoma. NCCIT is a developmentally pluripotent cell line that can differentiate into derivatives of all three embryonic germ layers and extraembryonic cell lineages an extract of undifferentiated somatic cells can elicit dedifferentiation in a somatic cell line. See Taranger et al., "Induction of Dedifferentiation, Genome-wide Transcriptional Programming, and Epigenetic Reprogramming by Extracts of Carcinoma and Embryonic Stem Cells" Mol Biol Cell. (2005).

Stem cells can establish in damaged tissue. See Menard et al., "Transplantation of cardiac-committed mouse embryonic stem cells to infarcted sheep myocardium: a preclinical study" Lancet, 366(9490):1005-12 (2005); Goldman "Stem and progenitor cell-based therapy of the human central nervous system" Nat. Biotechnol. 23(7):862-71 (2005); Leri et al., "Repair of the damaged heart" Kidney Int. 68(5):1962 (2005); Levy et al., "Embryonic and adult stem cells as a source for cell therapy in Parkinson's disease" J Mol. Neurosci. 24(3):353-86 (2004); Jack et al., "Processed lipoaspirate cells for tissue engineering of the lower urinary tract: implications for the treatment of stress urinary incontinence and bladder reconstruction" J. Urol. 174(5):2041-5 (2005); Kitmaura et al., Establishment of renal stem/progenitor-like cell line from S3 segment of proximal tubules in adult rat kidney Kidney Int. 68(5):1966 (2005).

In some embodiments, the invention relates to extracts that are capable of stimulating the immune system to aid in healing. For example, the extracts may contain fibrogen and heat shock proteins. These endogenous cellular components are alarm signals typically expressed in distressed or injured cells. They bind Toll-like receptors (TLRs) in antigen presenting cells (APCs) and put the immune system on alert of a damaged area. See Matzinger "The Danger Model: A Renewed Sense of Self" Science 296:301-305 (2002).

In some embodiments, the invention relates to stimulating existing stem cells in skin, such as stem cells found in and around hair follicles to duplicate and/or differentiate into epithelial cells or neurons. Nestin, a marker for neural progenitor cells, is expressed in cells of the hair-follicle bulge and behave as stem cells, differentiating to form much of the hair follicle during each hair growth cycle. The hair follicle is dynamic, cycling between growth (anagen), regression (catagen), and resting (telogen) phases throughout life. Stem cells located in the hair-follicle bulge area give rise to the follicle structures during each anagen phase. Bulge hair-follicle stem cells can generate all epithelial cell types within the intact follicle and hair during normal hair-follicle cycling. The bulge hair-follicle stem cells differentiate into hair-follicle matrix cells, sebaceous-gland basal cells, and epidermis. In response to wounding, some stem cells exit the bulge, migrate, and proliferate to repopulate the infundibulum and epidermis. Multipotent adult stem cells from the skin dermis, termed skin-derived precursors (SKPs), can proliferate and differentiate to produce neurons, glia, smooth muscle cells, and adipocytes. Pluripotent neural crest stem cells are present in the dermal papillae of adult mammalian hair follicles. See Amoh et al., "Multipotent nestin-positive, keratin-negative hair-follicle bulge stem cells can form neurons" Proc Natl Acad Sci USA. 12; 102(15):5530-4 (2005).

The bone marrow contains three stem cell populations—hematopoietic stem cells, stromal cells, and endothelial progenitor cells. Bone marrow stem cells, the hematopoietic stem cells (HSCs), are responsible for forming all of the types of blood cells in the body. The bone marrow-derived cells are sometimes sorted—using a panel of surface markers—into populations of hematopoietic stem cells or bone marrow stromal cells. The HSCs may be highly purified or partially purified, depending on the conditions used. Another way to separate population of bone marrow cells is by fractionation to yield cells that adhere to a growth substrate (stromal cells) or do not adhere (hematopoietic cells). The mesenchymal stem cells of the bone marrow also give rise to these tissues, and constitute the same population of cells as the bone marrow stromal cells. Progenitor cells that differentiate into endothelial cells, a type of cell that lines the blood vessels, can be isolated from circulating blood. Pericytes are related to bone marrow stromal cells.

Combinations of surface markers are used to identify, isolate, and purify HSCs derived from bone marrow and blood. Undifferentiated HSCs and hematopoietic progenitor cells express c-kit, CD34, and H-2K. These cells usually lack the lineage marker Lin, or express it at very low levels (Lin−/low). BM stromal cells have several features that distinguish them from HSCs. The two cell types are separable in vitro. When bone marrow is dissociated, the mixture of cells it contains is plated at low density, the stromal cells adhere to the surface of the culture dish, and the HSCs do not. Given specific in vitro conditions, BM stromal cells form colonies from a single cell called the colony forming unit-F (CFU-F). These colonies may then differentiate as adipocytes or myelo supportive stroma, a clonal assay that indicates the stem cell-like nature of stromal cells. Unlike HSCs, which do not divide in vitro (or proliferate only to a limited extent), BM stromal cells can proliferate for up to 35 population doublings in vitro. Endothelial stem cells are CD34+ (a marker for HSCs), and they express the transcription factor GATA-2 see Kocher, et al., "Neovascularization of ischemic myocardium by human bone-marrow-derived angioblasts prevents cardiomyocyte apoptosis, reduces remodeling and improves cardiac function" Nat. Med. 7, 430-436 (2001).

The present invention contemplates the use of any type of cell including stem cells from any multicellular organism in any kingdom of species, both eukaryotes including animals, plants, protists, fungi, and prokaryotes including the kingdoms archaebacteria and eubacteria. Multicellular organisms contain totipotent, mulitpotent, pluripotent and unipotent stem cells capable of dividing and replenishing tissues and cells which compose the organism. Stem cells are well documented in mammalian animals, but are present in all animals, e.g. insects. Adult fruit flies have the same stem cells controlling cell regulation in their gut as humans do. Vertebrate and invertebrate digestive systems show extensive similarities in their development, cellular makeup and genetic control. The *Drosophila* midgut is typical: enterocytes make up the majority of the intestinal epithelial monolayer, but are interspersed with hormone-producing enteroendocrine cells. Human (and mouse) intestinal cells are continuously replenished by stem cells, the misregulation of which may underlie some common digestive diseases and cancer. In contrast, stem cells have not been described in the intestines of flies, and *Drosophila* intestinal cells have been thought to be relatively stable. By lineage labelling it has been shown that adult *Drosophila* posterior midgut cells are continuously replenished by a distinctive population of intestinal stem cells (ISCs). (Benjamin Ohlstein and Allan Spradling, The adult *Drosophila* posterior midgut is maintained by pluripotent stem cells, Nature, online Dec. 7, 2005).

In addition to animal stem cells, plants also contain stem cells. Stem cells in plant shoot and root meristems are maintained throughout the life of the plant and produce somatic daughter cells that make up the body of the plant. Plant stem cells can also be derived from somatic cells in vivo and in vitro. (Plants stem cells: divergent pathways and common themes in shoots and roots. Byrne M E, Kidner C A, Martienssen R A. Curr Opin Genet Dev. 2003 October; 13(5):551-7.) Animal cells and organisms move, conduct cell divisions which serve to regenerate and maintain tissues and circulating cell populations, grow in a concurrently repetitive manner, contain a reserved germline set aside in embryogeny, have a low tolerance to genetic abnormalities, produce embryos complex and incomplete, and display essentially no asexual propagation and have no cell wall. Plants respond by physiological adjustment, their cell divisions contribute to de novo formation of organs all the way through to senescence, plant growth is serial, repetitive, and plastic, plants have no reserved germline, are more tolerant of genetic abnormalities, their embryos simple and complete, and plant cells are totipotent. Plant stem cells and seeds (plant gametes) are contemplated for use in this invention. Contrary to the rarity of totipotent cells in animals, almost every cell formed by a fungus can function as a "stem cell". The multicellular fruiting bodies of basidiomycete fungi consist of the same kind of filamentous hyphae that form the feeding phase, or mycelium, of the organism, and visible cellular differentiation is almost nonexistent (Money NP. Mushroom stem cells. Bioessays. 2002 October; 24(10):949-52).

The description is organized into the following sections: A. Adult stem cell extracts; B. Non-mammalian cell, egg and embryo extracts; C. Methods for preparing extracts; D. Epigenetic inhibitors; E. Enzymes involved in collagen synthesis and degradation; F. Ascorbic acid (vitamin C) as a cofactor in collagen synthesis; G. Iron as a cofactor in collagen synthesis; H. Topical delivery methods; I. Other delivery methods; J. Additional components for extracts; K. Composition profiles; L. Topical application; M. Therapeutic uses.

A. Adult Stem Cell Extracts

In some embodiments, the present invention provides compositions comprising adult stem cells or extracts prepared from adult stem cells. In some preferred embodiments, the cells or extracts are formulated for topical application as described in more detail below. The adult stem cell is an undifferentiated (unspecialized) cell that is found in a differentiated (specialized) tissue; it can renew itself and become specialized to yield specialized cell types of the tissue from which it originated. These precursor cells exist within the differentiated tissues of the adult of all multicellular organisms in the animal, plant, protist and fungi kingdoms as a community of cells dispersed throughout the tissue. Precursor cells derived from adults can be divided into three categories based on their potential for differentiation. These three categories of precursor cells are epiblast-like stem cells, germ layer lineage stem cells, and progenitor cells. Precursor cells have been isolated from a wide variety of tissues, including, but not limited to, skeletal muscle, dermis, fat, cardiac muscle, granulation tissue, periosteum, perichondrium, brain, meninges, nerve sheaths, ligaments, tendons, blood vessels, bone marrow, trachea, lungs, esophagus, stomach, liver, intestines, spleen, pancreas, kidney, urinary bladder, and testis. Precursor cells can be released from the connective tissue compartments throughout the body by mechanical disruption and/or enzymatic digestion and have been isolated from, but not limited to, newborns, adolescent, and geriatric mice, rats and humans, and adult rabbits, dogs, goats, sheep, and pigs.

The first category of precursor cells, epiblast-like stem cells (ELSCs), consists of a stem cell that will form cells from all three embryonic germ layer lineages. Stem cells from adult rats and stem cells from adult humans can be released from the connective tissue compartments throughout the body by mechanical disruption and/or enzymatic digestion. The stem cells from either adult rats or adult humans can be preferentially slow frozen and stored at −80° C.±5° C. using 7.5% ultra-pure dimethyl sulfoxide. Fast thawing of stem cells from both species from the frozen state to ambient temperature yields recovery rates exceeding 98%. These cells in the undifferentiated state express the Oct-3/4 gene that is characteristic of embryonic stem cells. ELSCs do not spontaneously differentiate in a serum free environment lacking progression agents, proliferation agents, lineage-induction agents, and/or inhibitory factors, such as recombinant human leukemia inhibitory factor (LIF), recombinant murine leukemia inhibitory factor (ESGRO), or recombinant human anti-differentiation factor (ADF). Embryonic stem cells spontaneously differentiate under these conditions. In contrast, ELSCs derived from both species remain quiescent unless acted upon by specific proliferative and/or inductive agents and/or environment.

ELSCs proliferate to form multiple confluent layers of cells in vitro in the presence of proliferation agents such as platelet-derived growth factors and respond to lineage-induction agents. ELSCs respond to hepatocyte growth factor by forming cells belonging to the endodermal lineage. Cell lines have expressed phenotypic markers for many discrete cell types of ectodermal, mesodermal, and endodermal origin when exposed to general and specific induction agents.

The second category of precursor cells consists of three separate stem cells. Each of the cells forms cells of a specific embryonic germ layer lineage (ectodermal stem cells, mesodermal stem cells and endodermal stem cells). When exposed to general and specific inductive agents, germ layer lineage ectodermal stem cells can differentiated into, for example, neuronal progenitor cells, neurons, ganglia, oligodendrocytes, astrocytes, synaptic vesicles, radial glial cells, and keratinocytes.

The third category of precursor cells present in adult tissues is composed of a multitude of multipotent, tripotent, bipotent, and unipotent progenitor cells. In solid tissues these cells are located near their respective differentiated cell types. Progenitor cells do not typically display phenotypic expression markers for pluripotent ELSCs, such as stage specific embryonic antigen-4, stage-specific embryonic antigen-1 or stage-specific embryonic antigen-3, or carcinoembryonic antigen cell adhesion molecule-1. Similarly, progenitor cells do not typically display phenotypic expression markers for germ layer lineage stem cells, such as nestin for cells of the ectodermal lineage or fetoprotein for cells of the endodermal lineage.

A progenitor cell may be multipotent, having the ability to form multiple cell types. A precursor cell of ectodermal origin residing in the adenohypophysisand designated the adenohypophyseal progenitor cell is an example of a multipotent progenitor cell. This cell will form gonadotrophs, somatotrophs, thyrotrophs, corticotrophs, and mammotrophs. Progenitor cells for particular cell lineages have unique profiles of cell surface cluster of differentiation (CD) markers and unique profiles of phenotypic differentiation expression markers. Progenitor cells do not typically spontaneously differentiate in serum-free defined medium in the absence of a differentiation agent, such as LIF or ADF. Thus, unlike embryonic stem cells which spontaneously differentiate under these conditions, progenitor cells remain quiescent unless acted upon by proliferative agents (such as platelet-derived growth factor) and/or progressive agents (such as insulin, insulin-like growth factor-I or insulin-like growth factor-II).

Progenitor cells can regulate their behavior according to changing demands such that after transplantation they activate from quiescence to proliferate and generate both new satellite cells and substantial amounts of new differentiated cells. For example, the contractile units of muscle are myofibers, elongated syncytial cells each containing many hundreds of postmitotic myonuclei. Satellite cells are resident beneath the basal lamina of myofibers and function as myogenic precursors during muscle regeneration. In response to muscle injury, satellite cells are activated, proliferate, and differentiate, during which they fuse together to repair or replace damaged myofibers. When satellite cells are removed from their myofibers by a non-enzymatic physical titration method, they retain their ability to generate substantial quantities of new muscle after grafting that they are not able to attain by enzymatic digestion. Conventional enzymatic disaggregation techniques impair myogenic potential. Collins and Partridge "Self-Renewal of the Adult Skeletal Muscle Satellite Cell" Cell Cycle 4:10, 1338-1341 (2005).

Accordingly, the present invention also contemplates the use of non-embryonic stem cells, such as those described above. In some embodiments, mesenchymal stem cells (MSCs) can be derived from marrow, periosteum, dermis and other tissues of mesodermal origin (See, e.g., U.S. Pat. Nos. 5,591,625 and 5,486,359, each of which is incorporated herein by reference). MSCs are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, various methods have been described for isolating, purifying, and greatly replicating the marrow-derived mesenchymal stems cells in culture, i.e. in vitro (See also U.S. Pat. Nos. 5,197,985 and 5,226,914 and PCT Publication No. WO 92/22584, each of which are incorporated herein by reference).

Various methods have also been described for the isolation of hematopoietic stem cells (See, e.g., U.S. Pat. Nos. 5,061,620; 5,750,397; 5,716,827 all of which are incorporated herein by reference). It is contemplated that the methods of the present invention can be used to produce lymphoid, myeloid and erythroid cells from hematopoietic stem cells. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Accordingly, the present invention also contemplates the use of neural stem cells, which are generally isolated from developing fetuses. The isolation, culture, and use of neural stem cells are described in U.S. Pat. Nos. 5,654,183; 5,672,499; 5,750,376; 5,849,553; and 5,968,829, all of which are incorporated herein by reference. It is contemplated that the methods of the present invention can use neural stem cells to produce neurons, glia, melanocytes, cartilage and connective tissue of the head and neck, stroma of various secretory glands and cells in the outflow tract of the heart.

In some embodiments, extracts are prepared from the mammalian embryonic stem cells. In some embodiments, cells are washed in phosphate buffered saline (PBS) and in cell lysis buffer (100 mM HEPES, pH 8.2, 50 mM NaCl, 5 mM $MgCl_2$, 1 mM dithiothreitol and protease inhibitors), sedimented at 400 g, resuspended in 1 volume of cold cell lysis buffer and incubated for 30-45 min on ice to allow swelling. Cells are sonicated on ice in 200-µl aliquots using a Labsonic-M pulse sonicator fitted with a 3-mm diameter probe (B. Braun Biotech, Melsungen, Germany) until all cells and nuclei are lysed. The lysate is sedimented at 15,000 g for 15 min at 4° C. to pellet the coarse material. The supernatant is aliquoted, frozen in liquid nitrogen and can be stored for up to 9 months at −80° C. If necessary, extracts can be diluted with $H_2O$ prior to use to adjust the osmolarity to ~300 mOsm (i.e., isotonicity).

In some embodiments, the adult stem cell extracts are used as is, while in other embodiments, the extracts are formulated either alone or with other components as described in more detail below.

B. Non-Mammalian Cell, Egg and Embryo Extracts

In some embodiments, the compositions of the present invention utilize cell, egg and embryo extracts from vertebrates, including but not limited to Superclass Gnathostomata (jawed vertebrates), Euteleostomi (bony vertebrates), Class Actinopterygii (ray-finned fishes), Class Sarcopterygii (lobe-finned fishes and terrestrial vertebrates), Tetrapoda (tetrapods), Amniota (amniotes), Synapsida (synapsids), Class Mammalia (mammals), Early Therapsida (early therapsids), Class Reptilia (reptiles), Anapsida (tortoises and turtles), Order Testudines (tortoises and turtles), Diapsida (birds, crocodiles, lizards, snakes, and relatives), Archosauria (birds and crocodiles), Order Crocodilia (caimans, crocodiles, and relatives), Lepidosauria (amphisbaenians, lizards, snakes, and tuataras), Order Rhynchocephalia (tuataras), Order Squamata (amphisbaenians, lizards, and snakes), Class Amphibia (amphibians), Subclass Dipnoi (lungfishes), Actinistia, Order Coelacanthiformes (coelacanths), Class Chondrichthyes (rays, sharks, and relatives), Placodermi (armored fishes and placoderms), Class Cephalaspidomorphi, more preferably fish, shrimp, sea urchin or amphibian eggs or embryos. In some embodiments, unfertilized but activated fish, shrimp, sea urchin or amphibian eggs are used. The present invention is not limited to the use of any particular types of eggs. Indeed, the use of a variety of eggs is contemplated, including, but not limited to eggs from *Xenopus*, shrimp, sea urchin, salmon, trout or zebrafish. In some embodiments, eggs are collected from mature females and spontaneously activate upon contact with water. In further embodiments, the eggs are washed in Ringer's saline. In some embodiments, the eggs are not from an avian species.

C. Preparation and Stabilization of Extracts and Fractions

Extracts of the present invention are prepared from any of the sources described in section A-D. In some embodiments, the extracts are cellular extracts. Cellular extracts of the present invention are compositions of disrupted cells such as stem cells or eggs. The cells may be disrupted by a variety of methods, including, but not limited to, mechanical shearing or blending, sonication, or osmotic lysis. In some embodiments, the cellular extracts are preferably further processed to yield a composition that is substantially free of lipids naturally associated with the cells, such as cell membrane components. By substantially free of lipids, it is meant that the cellular extract comprises less than about 1%, preferably less than about 0.5%, and more preferably less than about 0.1% of lipids that are naturally associated with the cells used to make the cellular extract. In some embodiments, the extracts comprise less than about 1% and preferably less than 0.1% cholesterol or ovalbumin. Accordingly, in some embodiments, the cellular extract comprises carbohydrates, proteins, glycosylated or otherwise modified proteins, peptides, amino acids, RNA (mRNA, sRNA, miRNA, rRNA), DNA, water etc, and combinations thereof. In some embodiments, the cellular extracts can comprise small amounts of lipids naturally associated with the cells, as well as nuclear components such as chromosomes, nucleic acids, and nuclear proteins. In some embodiments, the cellular extract is preferably a cytoplasmic extract or fraction prepared by removing nuclear, cell membrane and other water insoluble materials naturally associated with the cells. In some embodiments, these components are removed by centrifugation or fractionation of the disrupted cells. In some embodiments, the cellular extract is preferably an aqueous extract or fraction comprising water soluble cellular components such as proteins, mRNA, and carbohydrates.

A variety of methods may be used to prepare extracts. For example, in some embodiments, eggs are placed "dry" in a glass 15 ml centrifuge tube, and crushed by sedimentation at 15,000 g for 15 min. This produces three layers: a lipid top fraction, which is collected, aliquoted and frozen; a middle cellular or cytoplasmic fraction, which is also collected, aliquoted and frozen; and a pellet fraction, which is discarded. In some embodiments, the cellular fraction or extract primarily comprises contents of the cytoplasm. The cellular fraction is used as extract. In some embodiments, the cellular fraction may be used in combination with a lipid fraction. The cytoplasmic fraction may be cleared further by sedimentation at 50,000, 100,000 or 200,000 g to yield a further cellular extract which is primarily a water soluble extract fraction. Regardless of the fraction used, the extract can be diluted to about 300 mOsm with cell lysis buffer (see above), if necessary. Accordingly, in some preferred embodiment's, a water soluble extract prepared from eggs or embryos is utilized.

In other embodiments, the eggs are suspended in 0.5 volume of cell lysis buffer and sonicated on ice until all eggs are lysed. The particulate material is sedimented at 15,000 g for 15 min at 4° C. The supernatant constitutes the extract. As above, osmolarity can be adjusted to 300 mOsm if needed. The extract can also be cleared as above.

In still other embodiments, the eggs are suspended in cell lysis buffer as in method 2. Eggs are lysed by Dounce homogenization using a glass mortar and pestle (Kontes, type A or B). The lysate is sedimented and treated as described above.

In some preferred embodiments, the present invention provides compositions, either prepared from natural sources as described above or from artificial source materials, or a combination thereof. In some embodiments, the extracts are characterized as having an osmolarity of from about 330 to 440, preferably about 350 mOsm. In some embodiments, the extracts have a pH of from about 5.0 to about 7.7, preferably a pH of about 6.5-7.0. In some embodiments, the extracts have a protein content of about 100 to 250 mg/ml, preferably about 160 to 190 mg/ml, and most preferably about 120 mg/ml. In some embodiments, the compositions have a water content of about 20 to 90 percent water weight/weight (w/w), preferably about 37 to 79% water w/w. In some embodiments, the extracts have a density of about 0.8 to about 1.4 g/ml, preferably about 1.1 g/ml. In some embodiments, the compositions comprise trace elements including, but not limited to, calcium, phosphorus, zinc, copper and iron. In some embodiments, the compositions comprise vitamins, including, but not limited to vitamins A, C, E, riboflavin, niacin, B 6, calcium pantothenate and B 12. In some embodiments, the present invention provides a fresh roe composition comprising: 2.7 to 3.4% protein; 3 to 5% carbohydrates; 1.0 to 1.7% fats in the form of phospholipids, and 0.01 to 0.05% minerals in fresh roe, should be less fats and higher total protein in the extract), 37 to 79 weight percent water. In some embodiments, the extracts further comprise a lipid fraction. In some embodiments, the lipid fraction comprises from about 60% to about 80% unsaturated fatty acids. In further embodiments, the compositions comprise phospholipids, including phosphatidyl cholines (lecithins) or as phosphatidyl ethanolamine (cephalins), and to a lesser extent inositol phosphatides, cerebrosides and sphingomyelines. In some embodiments, the lipid fraction is from about 0.1% to about 1%, 2%, 3%, 4% or 5% of the total composition, while in other embodiments, the compositions are substantially free or free of lipids.

In some embodiments, the artificial extracts are prepared from 1) water, 2) any type of protein (BSA, albumine, vitellogenin, amino acid mixtures, etc.), 3) vitamins and minerals as described above, 4) salts or osmoles to create osmolarity of approx 350 mOsm, 5) glycerol or other agent to increase viscosity, 6) lipids such as lecithins, cephalins and other phospholipids, 7) carbohydrates, 8) growth factors such as FGF, EGF and IGF, 9) and chemo-attractants such asSLC/6Ckine/Exodus2/TCA4 and CKbeta-11/MIP-3beta/ELC, 10) acid or base to adjust pH to 6.2-7.2, and 11) preservatives such as methyl paraben, propyl paraben, BHA or BHT.

In some embodiments, the eggs or extracts are treated to prevent bacterial growth. The use of a variety of methods is contemplated. In some embodiments, the following methods are combined. In some embodiments, unfertilized or fertilized eggs (e.g., fish or amphibian eggs) are treated prior to homogenization with a bactericidal or bacteriostatic agent. Preferred agents include, but are not limited to, iodine containing agents such as betadine, buffodine, and povidone-iodine, and other agents such as novasan, sodium hypochlorite, bacitracin, polymyxin B sulfate, silver containing compounds such as silver sulfadiazine and silver nitrate, mafenide acetate, nystatin, gentamicin, neomycin. In other embodiments, the extracts are treated post-homogenization to prevent bacterial growth. In some embodiments, the extracts, such as the cellular extracts or cytoplasmic fractions, are treated by heating. In some embodiments, the extracts are heated to about 37, 40, 50, 60, 70, 80 or 90 degrees Celsius for about 30 seconds or 1, 2, 5, 10, 20, 30, 60 or 120 minutes.

In some embodiments, the eggs or extracts are filtered, preferably through 0.22 or 0.45 um filters to remove bacteria. In some embodiments, before or after filtering, the extracts are treated by additional centrifugation (15 min-2 hrs) after heating the extract to 56° C. to spin down any bacteria present.

In other embodiments, eggs are washed in a sulfur-containing agent (e.g., calcium polysulfide or calcium thiosulfate (lime sulfur)) prior to preparation. In some embodiments, sulfur is added to the extracts to remove bacteria. In other embodiments, benzoyl peroxide is added to the extracts. In some embodiments, eggs are washed in 0.001% to about 0.2% by weight of a metal chlorite and sufficient acid to adjust the pH of the solution from about 2.2 to about 4.5 to remove bacteria. In further embodiments, the eggs and/or extract are placed in a vacuum drum and mixed with a natural solution containing salt, vitamin C or citric acid, and water to remove bacteria. In some embodiments, the eggs and/or extract are stirred, vortexed, sonicated, agitated or shaken with salt water or liquid buffer to dislodge bacteria and vacuum filter off the liquid to remove bacteria. It will be possible to check bacterial content in the liquid and on the treated eggs for quality control. In some embodiments, electrophoresis of the eggs and/or extract is used to remove bacteria. It is contemplated that such methods utilize the influences of electrical double layer, intensity of electrical field, electric density gradient, pH of the buffer solution, ionic strength of buffer solution, stage of growth of bacteria, and anion surface-active agent upon the electrophoretic mobility of some species of bacteria.

In some embodiments, lipids are removed by treatments the homogenate prior to centrifugation or the extract after centrifugation. The use of a variety of methods is contemplated. In some embodiments, lipids are removed by filtering through fat-absorbing paper or filter by applying a vacuum suction system to a container with a filter in the bottom, where the extract is placed in the container and suctioned through the filter. In some embodiments, lipids are removed by using an absorbent material and an outer containment vessel. The extract is entered to a container filled with absorbent material through a pump and then recovered by applying a vacuum. In some embodiments, lipids are removed with hollow fiber contraction systems and/or extraction solvents for removing lipids from viscous fluids, where contact a fluid with an extraction solvent, which causes the lipids in the fluid to separate from the fluid or causes lipids in the lipid-containing organisms to separate from the lipid-containing organism, using at least one hollow fiber contactor.

In some embodiments, the homogenates and extracts may be stabilized by the addition of one or more stabilizing agents, such as a lipid stabilizing agent, or by packaging in a package designed to prevent oxidation. In some embodiments, antioxidants such as vitamin E are added to the extract to reduce rate of lipid oxidation. In some embodiments, the extracts are packaged in a container under an inert atmosphere. In some embodiments, the extract is packaged to reduce rate of lipid oxidation in air-free containers such as aluminum coated bags (less than 10 kg per bag for efficient removal of oxygen), or containers filled with nitrogen to remove oxygen. In other embodiments, the extracts are packaged in vacuum packed containers with a pump delivery system.

In some embodiments, extracts from stem cells, such as embryonic stem cells, are prepared in a like manner. In these embodiments, the stem cells are first disrupted and then centrifuged as above to remove insoluble cellular debris. The stem cells generally comprise much less lipid material, so the initial centrifugation yields two main fractions, a pellet and cellular fractions which primarily contains cytoplasmic components. In some embodiments, cells, either a plate of cells or cells collected from flasks or fermentors, are washed in ice cold PBS. When a plate of cells is utilized, the cells are scraped and transferred to an ice cold centrifuge tube, such as an Eppendorf tube. In some embodiments, the cells are then pelleted and the supernatant is removed. The cells are then disrupted. In some embodiments, a hypotonic solution is added to the cells in a volume of from about 1.5:1 to 3.0:1 as compared to the cell pellet. A suitable hypotonic solution comprises 10 mM HEPES pH 7.9, 1.5 mM $MgCl_2$, 10 mM KCl 3.33, 0.5 mM DTT, and 0.2 mM PMSF. In some embodiments, a 10% solution of Triton X is then added (about 1/20 volume) to the pellet and the pellet resuspended by vortexing. In some embodiments, the cells are then homogenized, for example with a Dounce homogenizer or sonicated to further disrupt the cells. In some embodiment, the cellular debris is then pelleted by centrifugation, for example 6,000 RPM at 4° C. for 30 seconds. The supernatant is then collected as the cellular extract.

In some embodiments where fish eggs are utilized, the fish eggs are treated to prevent bacterial growth as described above. The fish eggs are then homogenized by subjecting the fish eggs to a pressure treatment. In some embodiments, the eggs are subjected to a pressure of from about 1 ton to about 100 tons, preferably about 5 tons to about 50 tons, more preferably about 10 tons to about 30 tons and most preferably about 20 tons. In some embodiments, the pressure is applied via a hydropress. Suitable hydropresses are available from Speidel. In some embodiments, components of the homogenate are separated. In some preferred embodiments, an aqueous cytoplasmic fraction is obtained that comprises protein, DNA, RNA, and other components as described in more detail elsewhere herein. In some embodiments, the extracts comprise a lipid component in addition to the water soluble components. In some embodiments, the extract is separated from the homogenate by centrifugation. In some embodiments, the centrifugation is a continuous-feed process facilitated by a separator. Suitable separators are available, for instance, from GEA Westfalia.

In some embodiments, the present invention provides processes for producing an active fish egg fraction comprising milling the eggs between two or more surfaces disposed so as to cause crushing of the eggs as the eggs pass the surfaces. In some embodiments, at least one of the surfaces comprises cutting elements, for example knurls. In some embodiments, the mill is a roller mill comprising two or more cylindrical rollers. In some embodiments, each of the rollers comprising a cutting surface, for example a knurled surface. In some embodiments, the eggs are placed in a hopper and fed to the milling surface(s). In the case of a roller mill, the eggs are passed between the rollers, causing the eggs to be crushed to form a homogenate. In some embodiments, the milling surfaces (e.g., the surfaces of rollers) are spaced apart to effectuate crushing of eggs passing the surfaces. For example, in some embodiments, the surfaces are separated by from 0.1 to 5 mm, preferably about 0.5 to 2 mm. In some preferred embodiments, the processes further comprise separating an active fraction from said fish egg homogenate, wherein the active fraction comprises about 100 to 380 mg/ml protein in an aqueous solution; about 0.1 to 10 mg/ml RNA; about 0.1 to 5 mg/ml DNA and 0.1-10% lipids w/w. In some embodiments, the separating of the active fraction is by a centrifugal force, as described above.

In some embodiments, the cellular extracts described above, and most preferably the middle fractions, are further fractionated. A variety of method may be used, including, but not limited to, FICOL gradients, gradient centrifugation, protein precipitation, freeze drying, column chromatography, such as size exclusion chromatography and affinity chromatography, gel separation, high pressure liquid chromatography, ChIP, and immunoprecipitation. It will be recognized that these fraction steps yield corresponding fractions such as freeze dried fractions, affinity chromatography fractions, precipitated fractions, etc.

In some embodiments, the fractions are then combined with or resolubilized with components suitable for preparing compositions for topical administration as described in more detail below.

D. Epigenetic Inhibitors

In some embodiments, the compositions of the present invention further comprise epigenetic inhibitors. In preferred embodiments, one or more epigenetic inhibitors are combined with one or more of the cellular extracts described in Sections A-E. The present invention is not limited to the use of any particular epigenetic inhibitors. Indeed, the use of variety of epigenetic inhibitors is contemplated, including, but not limited to synthetic epigenetic inhibitors and epigenetic inhibitors isolated or derived from natural sources. Examples of epigenetic inhibitors include, but are not limited to histone deacetylase inhibitors, DNA methyltransferase inhibitors and some vitamins.

In some embodiments, the epigenetic inhibitors comprises a natural extract containing butyrate or butyric acid made from natural foods such as butter from animal fats or milk (e.g. cows milk or cheese), plant oils (e.g. *Heracleum giganteum* (cow parsnip) and *Pastinaca sativa* (parsnip)), or Kombucha tea (includes Butyric Acid as a result of fermentation containing butyrate). Extract preparation may include fermentation by obligate anaerobic bacteria (e.g. *Clostridium butyricum, Clostridium kluyveri, Clostridium pasteurianum, Fusobacterium nucleatum, Butyrivibrio fibrisolvens, Eubacterium limosum*). Animal fat or plant oil product extracts may be prepared by chemical or physical processes inducing the liberation of butyric acid from the glyceride by hydrolysis.

The extract could also be prepared by the fermentation of sugar or starch in the natural foods by the addition of *Bacillus subtilis*, with calcium carbonate added to neutralize the acids formed.

In other embodiments, the epigenetic inhibitors comprise a natural extract of red grapes containing the phytoalexin resveratrol, including an extract from juice or fermented juice (wine) of red grapes. Extracts could be prepared by mechanical disruption of grapes, separation of the skin from the flesh and seeds, and either extracting phytoalexin by chemical or mechanical methods, or be prepared from fresh or fermented grape juice by chemical or physical methods including boiling, fractionation, affinity chromatography, freeze-drying or gel separation.

In other embodiments, the epigenetic inhibitors comprise a natural extract containing Cyanocobalamin (vitamin B-12) made from organisms containing enzymes required for the synthesis of B12 such as bacteria and archaea, or natural products which harbor such B12 producing bacteria including meat (especially liver and shellfish), eggs, and milk products. Extracts can be prepared by chemical or physical methods such as homogenization followed by fractionation, affinity chromatography, freeze-drying or gel separation.

In other embodiments, the epigenetic inhibitors comprise a natural extract containing one or several variants of vitamin B, made from either potatoes, bananas, lentils, chilli peppers, tempeh, liver, turkey, tuna, nutritional yeast (or brewer's yeast), beer or marmite. Extracts can be prepared by chemical or physical methods such as homogenization followed by e.g. fractionation, affinity chromatography, freeze-drying or gel separation.

In other embodiments, the epigenetic inhibitors comprise a natural extract containing retinoids or retinoid precursors, made from either animal sources (e.g. milk and eggs) which contain retinyl esters, or from plants (e.g. carrots, spinach) which contain pro-vitamin A carotenoids. The extract may be modified by hydrolysis (animal sources) of retinyl esters to result in retinol, while plant extracts containing pro-vitamin A carotenoids can be cleaved to produce retinal (retinaldehyde), which can be further be reversibly reduced to produce retinol or it can be irreversibly oxidized to produce retinoic acid. The best described active retinoid metabolites are 11-cis-retinal and the all-trans and 9-cis-isomers of retinoic acid, which may be added to this extract.

Examples of other DNA methyltransferase inhibitors include, but are not limited to, 5-Azacytidine, 5-Aza-20-deoxycytidine, Arabinosyl-5-azacytidine, 5-6-Dihydro-5-azacytidine, 5-Fluoro-20-deoxycytidine, EGX30P, Epigallocatechin-3-gallate, Green tea polyphenol, Hydralazine, MG98, Procainamide, Procaine, and Zebularine. Examples of other histone deacetylase inhibitors include, but are not limited to Apicidin, Butyrates, Phenylbutyrate, m-Carboxycinnamic acid bishydroxamide (CBHA), Cyclic hydroxamic-acid-containing peptide 1 (CHAP1), TSA-Trapoxin Hybrid, Depudecin Epoxide, Depsipeptide FR901228, Benzamidine, LAQ824, Oxamflatin, MGCD0103, PXD101, Pyroxamide, Suberic Bishydroxamic Acid (SBHA), Suberoylanilide Hydroxamic Acid (SAHA), Trichostatin A (TSA), Trapoxin A, and Valproic acid.

E. Enzymes Involved in Collagen Synthesis and Degradation

In some embodiments, the extracts described above (or components of the extracts) are in a composition further including, but not limited to the enzymes, procollagen peptidase, which form tropocollagen; hydroxylases, responsible for the step of hydroxylation of selected proline and lysine amino acids in the newly synthesized procollagen protein. The hydroxylase enzymes require Vitamin C and Iron as cofactors. If a patient is Vitamin C deficient, then this reaction will not occur (Reference: Mussini E, Hutton J J, Udenfriend S. Collagen proline hydroxylase in wound healing, granuloma formation, scurvy, and growth. Science 1967; 157:927-9).

F. Ascorbic Acid (Vitamin C) as a Cofactor in Collagen Synthesis

In some embodiments, the extracts described above (or components of the extracts) are in a composition further including ascorbic acid (Vitamin C) on which the hydroxylation step in the formation of collagen intracellularly is dependent. Additionally, Vitamin C is beneficial for skin because deficiency causes scurvy, a serious and painful disease in which defective collagen prevents the formation of strong connective tissue. Gums deteriorate and bleed, with loss of teeth; skin discolors, and wounds do not heal.

G. Iron as a Cofactor in Collagen Synthesis

In some embodiments, the extracts described above (or components of the extracts) are in a composition further including iron (Fe) on which the hydroxylation step in the formation of collagen intracellularly is dependent.

H. Other Delivery Methods

In some embodiments, the extracts described above (or components of the extracts) are formulated for delivery by a variety of methods. In some embodiments, the extracts described above are formulated for delivery to skin, gastrointestinal tractus, fat deposits, cartilage, bone, connective tissue, muscle or internal organs. In some embodiments, the extracts or components thereof are formulated for oral administration with or without suitable carriers such as starch, sucrose or lactose in tablets, pills, dragees, capsules, solutions, liquids, slurries, suspensions and emulsions. In some embodiments, the oral delivery vehicle comprises an enteric coating. In other embodiments, the extracts or components thereof are formulated for rectal administration as a capsule, cream, suppository or liquid. In some embodiments, the extracts of components thereof are injected by syringe to the peritoneal cavity or into internal organs or tissues. In some embodiments, the extracts or components thereof are formulated for delivery an osmotic pump.

In still other embodiments, the extracts or components thereof are delivered by microinjection, preferably via particle bombardment (i.e., with a gene gun). Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue. Other particle bombardment methods are also available. Generally, these methods involve depositing the extract or components thereof upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles that maximizes the number of cells receiving particles under uniform conditions, resulting in the introduction of the nucleic acid sample into the target tissue. This invention contemplates the described use of gene-gun to deliver extracts or components of extracts as defined above.

In still other embodiments, the embryonic stem cell, adult stem cell or egg extracts or components are microencapsulated (e.g., with collagen or glycosaminoglycans), formed into nanoparticles (e.g., lecithin encapsulated in an oil core), liposomes, microemulsions, or nanoemulsions, oil bodies, retinol molecular fluid films, unilamellar vesicles, multilamellar vesicles, preloaded spherical beads or sponges, elastic vesicles, etc.

I. Composition Profiles

In some embodiments the composition for topical and/or internal application is a combination of extracts with lipids and/or water and/or carbohydrates and/or nucleic acids and/or proteins and/or signaling substances. In some embodiments the extract herein is composed of whole cells or a combination of lipids and/or carbohydrates and/or nucleic acids and/or proteins and/or signaling substances of the cells from which the extract is made, or from synthetic and/or natural versions of lipids and/or carbohydrates and/or nucleic acids and/or proteins and/or signaling substances. Signaling profiles include combinations of active substances released from cells which are contained in extracts of cells, and include synthetic and/or natural versions of these signaling substances added to extracts. Signaling substances contemplated include but are not limited to growth factors, endorphins, hormones, amino acid transmitters, immunoregulatory cytokines and other immunity-associated factors.

Growth factor-β1 orchestrates the biology of irradiated tissue as a tissue level sensor of oxidative stress, and is integral to the cellular DNA damage response. Transforming growth factor-β5 (TGF-β5), a member of this signaling factor family found in amphibians, is expressed in regenerating blastemas formed under limb regeneration (King et al., 2003), and all mammalian isoforms of TGF-β are released locally from various cells at sites of injury and are important in the control of fibrosis and scarring during mammalian tissue repair. Manipulation of specific TGF-β isoforms is capable of producing scar-free healing of wounds in mice (Ferguson and O'Kane, 2004). TGF-β1 is a potent immunoregulatory cytokine involved in suppression of inflammation and regulatory T cell activity, resulting in immune tolerance (Chen and Wahl, 2003). Studies on wound healing and immunosuppression in mammals indicates that differential activity of TGF-β in regenerating amphibian limb stumps may be involved suppression of fibrosis and establishing conditions permissive for blastema formation.

Transforming growth factor-alpha (TGF-alpha) and brain-derived neurotrophic factor (BDNF) secreted in vitro from human pluripotent stem cells derived from embryonic germ cells, termed embryoid body-derived (EBD) cells, have the capacity to restore neurologic function in animals by protecting host neurons from death and facilitate reafferentation of motor neuron cell bodies (Kerr D A, et al., Human embryonic germ cell derivatives facilitate motor recovery of rats with diffuse motor neuron injury. J. Neurosci. 2003 Jun. 15; 23(12):5131-40).

Fibroblast growth factors (FGFs) such as FGF-10 have been demonstrated to be of importance in regrowth of limbs in frogs (Christen and Slack, 1997; Yokoyama et al., 2000).

The Pro-opiomelanocortin (POMC) precursor for a-melanocyte stimulating hormone (α-MSH), endorphins, and several other peptide hormones, is expressed in regeneration blastemas (King et al., 2003), in skin as well as brain, pituitary, and other organs. POMC is a central importance in modulating immune activity within skin, primarily due to the activity of α-MSH (Luger et al., 1999). Paracrine release of α-MSH peptides exerts a potent immunomodulatory effect on immune cells. α-MSH inhibits all forms of inflammation against which it has been tested (Lipton et al., 1997) and localized production of α-MSH helps maintain optimal immune response at specific sites in the skin (Paus et al., 2003). Expression of α-MSH cells of a blastoma would be expected to confer an anti-inflammatory effect potentially important for inhibiting fibrosis and regeneration necessary for limb or tissue regrowth.

Thymosin-β4 is a thymic maturation factor that has also been shown to promote angiogenesis, keratinocyte migration and wound healing (Malinda et al., 1999). Thymosin-β4 exerts potent anti-inflammatory activity and is secreted by macrophages and T lymphocytes of skin, gut and other organs in addition to the thymus (Young et al., 1999; Girardi et al., 2003). Thymosin-β4 is up-regulated in frog pseudoblastemas (King et al., 2003) and regenerating blastemas and activities of thymosin-β4 in tissues of amputated limbs may include immunomodulation of the inflammatory response in addition to stimulation of epithelial migration and other aspects of regeneration.

J. Additional Components

In some embodiments, the extracts or components thereof described above are combined with additional components. In some embodiments, these additional components enhance uptake, bioavailability or penetration of the extract components. In preferred embodiments, extract components may contain natural or a mixture of synthetic components. The components may be partially or totally synthetic. In some embodiments, the cell or extract or synthetic components made from substances identified in the extracts are mixed with a composition comprising water, sebaceous and epidermal lipids and cell extracts, proteins, and components thereof, preferably comprises about a 10% lipid fraction by weight, about a 10% protein fraction by weight, and about an 80% volatile fraction by weight.

In some embodiments, the compositions of the present invention further comprise lipids, preferably lipids having beneficial effects in skin. The lipids include but are not limited to omega-3 fatty acids, myristic acid, and stearidonic acid, and combinations thereof. In some embodiments, the omega-3 fatty acid is eicosapentaenoic acid (EPA), which has been shown to have a photoprotective and anti-aging effect on skin (Kim H H. et al. Photoprotective and anti-skin-aging effects of eicosapentaenoic acid in human skin in vivo. J Lipid Res. 2006 May; 47(5):921-30.) In other embodiments, the omega-3 fatty acid is docosapentaenoic acid (DPA), which is beneficial for the cell membrane in fibroblast skin cells. In other embodiments, the omega-3 fatty acid is docosahexaenoic acid DHA). In some embodiments, the lipids comprise a combination of one or more these omega-3 fatty acids. Stearidonic acid reduces skin redness. Myristic acid increases penetration of active substances into skin, specifically into fibroblasts (Eric R. Brown and Papasani V. Subbaiah. Differential effects of eicosapentaenoic acid and docosahexaenoic acid on human skin fibroblasts. Lipids. 1994 Dec. 29(12): 803-913); Zulfakar M. H. et al. Enhanced topical delivery and ex vivo anti-inflammatory activity from a betamethasone dipropionate formulation containing fish oil. J Inflammation Res. Volume 59 (1): 1-88); Mittal A, et al. The effect of penetration enhancers on permeation kinetics of nitrendipine in two different skin models. Biol Pharm Bull 2008 September; 31(9):1766-72.).

In further embodiments, the compositions further comprise natural marine-derived fat-soluble vitamins such as Vitamin A and E. These are well known to be beneficial for skin both as antioxidants and by direct effect on fibroblast health. Vitamin E is vital in protecting skin cells from ultra violet light, pollution, drugs, and other elements that produce cell damaging free radicals (Riedel S B et al. Vitamin E analog, alpha-tocopherol ether-linked acetic acid analog, alone and in combination with celecoxib, reduces multiplicity of ultraviolet-induced skin cancers in mice. Anticancer Drugs. 2008 February; 19(2):175-81). Vitamin A has been shown in many studies to prevent and reverse cancerous changes in cells in some parts of the body, including the skin, and repairs skin damage caused by the sun (REFERENCE: Alberts D. et al. Safety and efficacy of dose-intensive oral vitamin A in subjects with sun-damaged skin. Clinical Cancer Research 2004; 10:1875-80.).

In further embodiments the compositions comprise natural or synthetic proteins including but not limited to the protein vitellogenin, known for its rejuvenating properties. Vitellogenin is also present in honey, heralded for giving bees prolonged lives (Münch D, Amdam G V. The curious case of aging plasticity in honey bees. FEBS Lett. 2010 Apr. 10). Ref 9) In further embodiments the composition contains natural or synthetic peptides, herein defined as polymers formed from the linking, in a defined order, of α-amino acids; including but not limited to milk peptides, ribosomal peptides, nonribosomal peptides, peptones and peptide fragments. Peptides are believed to have a good effect on skin and wrinkles. Because peptides are so small, it is thought that they may more easily penetrate the skin and yield their effects.

Vernix caseosa (vernix) is a naturally occurring skin protectant. Vernix is a lipid rich substance composed of sebum, epidermal lipids, and desquamated epithelial cells that progressively covers the skin of the developing fetus, completely surrounded by amniotic fluid, during the last trimester of pregnancy. In some embodiment, the invention relates to compositions where the lipid fraction preferably comprises components in vernix, i.e., lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). In preferred embodiments, the vernix lipid components are as follow, with the relative percentages indicated, squalene (9%), aliphatic waxes (12%), sterol esters (33%), diesters (7%), triglycerides (26%), free sterols (9%), other lipids (4%). In additional embodiments, the lipid composition is composed of lipids from egg and/or fish roe with wound healing properties 30% of which are barrier lipids (proteolipid matrix); cholesterol (1.1%, 52.8% of barrier), free fatty acids (0.6%, 27.7% of barrier), phospholipids (0.4%), ceramides (0.7%, 20.1% barrier). In another preferred embodiment, the protein fraction contains the protein components of vernix, i.e., keratin, filaggrin, regulator proteins (e.g. EGF), and glutamine.

The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor (EGF), and trace amounts of about nanomolar to micromolar concentrations of surfactant protein such as Surfactant A and Surfactant B. The volatile fraction is primarily water. The rate of evaporation of volatile components is relatively slow, presumably due to increased energy requirements for the dissociation of hydrogen bonds and for diffusion from the cellular component through the lipid component to change water from the liquid to the gaseous state. In additional preferred embodiments, the composition contains mRNA contained in cell extracts, preferably stem cell extracts.

In some embodiments, the embryonic stem cell, adult stem cell or egg extracts or components are combined with phospholipids or other lipophilic substances, palmitylmyristrates, dimethylsulfoxide (DMSO), chitosan, long chain organic polymers such as polysaccharides, non-aqueous solvents, beta-glucan, pH adjusting components, skin metabolism inhibition agents, propylene glycol, butylenes glycol, polyethylene glycol, olive oil or other naturally occurring oils, dimethyl isosorbide, dimethylformamide, methyl salicylate, long chain oleic acid, mucopolysaccharides, and other agents.

In some embodiments, the additional agents include, but are not limited to, ubiquitin, antimicrobial agents (alpha-defensins, LL37, beta-defensins, etc.), surfactant proteins from the collectin family (collecting associated protein A and D), nicotinamide and psoriacin.

In some embodiments, the additional agents include, but are not limited to, vitamins, antioxidants, minerals, extracts, and chemical compounds such as alpha-tocopherol (vitamin E), melanin, vitamin C, provitamin A, retinyl proprionate, retinoic acid, Vitamin D3, Nicotinamide (vitamin B), Niacinaminde (Vit B3, exfoliates surface skin), d-panthenol (aids in skin repair of damage), vitamin A, hyaluronic acid, ceramides, Seaweed (algae) Mineral oil (paraffinum liquidium) Petrolatum Glycerin Isohexadecane *Cirtus aurantifolia* (lime) extract Microcrystalline wax (*cera microcristallina*) Lanolin alcohol *Sesamum indicium* (sesame) seed oil, Eucalyptus globules (eucalyptus) leaf oil, Magnesium sulfate, *Sesamum indicum* (sesame) seeds, *Medicago satvia* (alfalfa) seeds, *Helianthus annuus* (sunflower) seeds, *Prunus dulcis* (powdered almonds), Sodium, Potassium, Copper, Calcium, Magnesium, zinc gluconate, Paraffin, Vitamin E succinate, Niacin, Beta-carotene, Decyl oleate, Aluminum distearate, Octyuldodecanol, Citric acid, Cyanocobalamin, Magnesium stearate, Panthenol, Limonene, Geraniol, Linalool, Hydroxycitronellal, Citronellol, Benzyl salicylate, Citral, Methylchloroisothiazoline, Methylisothiazolinone, Alcohol denat., Fragrance (parfum), Butylene glycol, *Byrospermum parkii* (shea butter), Fish (pisces) cartilage extract, Polyethylene, Hydrogenated polyisobutene, Cyclopentasiloxane, Cetyl esters, Cetearyl alcohol, Malachite, Isostearyl neopentanoate, Polybutene, Sucrose, Silica, Tocotrienol, *Cucumis satvius* (cucumber) fruit extract, *Centella asiatica* (hydrocotyl) extract, *Sesamum indicium* (sesame) seeds, Eucalyptus globules (eucalyptus) leaf oil, *Medicago satvia* (alfalfa) seeds, *Helianthus annuus* (sunflower) seeds, *Prunus dulcis* (powdered almonds), Potassium, Copper, Calcium, Magnesium, Caffeine, Sodiumhyaluronate, Linoleic acid Cholesteryl/behenyl/octyldodecyl lauroyl glutamate, Methyl glucose sesquisterate, Cholesterol, Dimethicone, *Ocimum basilicum* (basil), *Mentha arvensis* (wild mint), Acrylates/C10-30 alkyl acrylate crosspolymer, Glyceryl distearate, Cetearyl glucoside, Steareth-10, Carbomer, Aminomethyl propanol, Limonene, Linalool, Benzyl salicylate, Disodium EDTA, BHT, Sodium dehydroacetate, Phenoxyethanol, Methylparaben, Titanium dioxide (CI-77891), C12-20 acid PEG-8 Ester, Hydrogenated vegetable oil, Petrolatum, Butylene Glycol, Glycerin, Acetylated Lanolin, Glycoproteins, Panax, Ginseng Root extract, *Equisetum Arvense* (Horsetail) Extract, Sodium carbomer, Beeswax (*cera alba*), Cetyl phosphate, Polyperfluoromethylisoporpyl ether, Benzyl alcohol, Linalool, Hydroxycitronellal, Alpha-isomethyl ionone, Amyl cinnamal, Hexyl cinnamal, *Verenia furfuracea* (treemoss) extract, Geraniol, Benzyl benzoate, Bytulphenol methylpropional, Eugenol, Benzyl salicylate, Chlorphenesin, Phenoxyethanol, and Methylparaben.

In some embodiments, the compositions of the present invention are useful for facilitating the delivery of active compounds via the skin. In some preferred embodiments, one or more active agents, such as a protein, small organic compound, or one of the agents identified above are combined with the cytoplasmic fraction of, for example, a fertilized or unfertilized amphibian or fish eggs. Cytoplasmic fractions and method for making such fractions are disclosed elsewhere in the application in detail. Accordingly, in some embodiments, the present invention provides compositions comprising a cytoplasmic fraction of amphibian or fish eggs and one or more active agents. In some embodiments, the present invention provides methods of facilitating the penetration of one or more active agents into the skin, comprising providing a composition comprising a cytoplasmic extract from amphibian and/or fish eggs and one or more active agents and contacting the skin of a subject with the composition. As described above, the composition can be preferably be an emulsion, salve, cream, gel, spray, aerosol, liquid, etc.

Exemplary proteins that can be active agents include, but are not limited to, Alzheimer's amyloid peptide (Aβ), SOD1, presenillin 1 and 2, renin, α-synuclein, amyloid A, amyloid P, activin, anti-HER-2, bombesin, enkephalinase, protease inhibitors, therapeutic enzymes, α1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as α FGF and β FGF), insulin-like growth factor-I and -II, des(1-3)-IGF-I (brain IGF-I), insulin-like growth factor binding proteins, nerve growth factor (such as NGF-β, platelet-derived growth factor (PDGF), vascular endothelial growth factor (VEGF), receptors for growth hormones or growth factors, transforming growth factor (TGF) (such as TGF-α, TGF-β1, TGF-β2, TGF-β3, TGF-β4 or TGF-β5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin β-chain, insulin receptor, proinsulin, luteinizing hormone, integrin, interleukins (ILs) (such as IL-1 to IL-10, IL12, IL-13), erythropoietin, thrombopoietin, fibrillin, follicle stimulating hormone, clotting factors (such as factor VIIIC, factor IX, tissue factor, and von Willebrands factor, anti-clotting factors (such as Protein C, atrial naturietic factor, lung surfactant), a plasminogen activator (such as human tissue plasminogen activator or urokinase), thrombin, tumor necrosis factor-α or β, α-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-α, -β and -γ), keratin, osteoinductive factors, PRNP, regulatory proteins, superoxide dismutase, surface membrane proteins, transport proteins, T-cell receptors, viral antigens such as a portion of the AIDS envelope, immunoglobulin light chain, antibodies, antibody fragments (such as single-chain Fv fragment (scFv), single-chain antibody (scAb), $F_{AB}$ antibody fragment, diabody, triabody, fluorobody), antigens such as gp120(IIIb) immunotoxins, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, gp120, p300, CREB, AP1, ras, NFAT, jun, fos, dentaorubral pallidoluysian atrophy-associated protein, a microbial protein (e.g., maltose binding protein, ABC transporter, glutathione S transferase, thioredoxin, β-lactamase), green fluorescent protein, red fluorescent protein, or derivatives or active fragments or genetic variants of any of the peptides listed above.

Examples of small organic compounds include, but are not limited to, non-steroidal anti-inflammatory drugs (NSAIDS) (the NSAIDS can, for example, be selected from the following categories: (e.g., propionic acid derivatives, acetic acid derivatives, fenamic acid derivatives, biphenylcarboxylic acid derivatives and oxicams)); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenflurarnine); central stimulant drugs (e.g., amphetamine, methamphetamine, dextroamphetamine and methylphenidate); minoxidil; antiarrhythmic drugs (e.g., propanolol, procainamide, disopyraminde, quinidine, encamide); P-adrenergic blocker drugs (e.g., metoprolol, acebutolol, betaxolol, labetalol and timolol); cardiotonic drugs (e.g., milrinone, aminone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); PDE5 inhibitors such as Viagra® or Clalis®; tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The compositions can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful active compounds include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

In some embodiments, components of the extract may act as chemotaxants. Mesenchymal stem cells and fibrocytes circulates in the blood stream and in case of skin wound they penetrate the wound area where they can differentiate to skin cells like fibroblasts, keratinocytes, pericytes, adipose and endothelial cells. Chemotaxants in the extract may act as ligands for the CCR7 involved in attractin immune cells and dendritic cells and may include SLC/6Ckine/Exodus2/TCA4 and CKbeta-11/MIP-3beta/ELC K. Topical Application In some embodiments, the extracts described above (or components of the extracts) are formulated for topical delivery. General formulations for topical delivery are described in Remington's Pharmaceutical Sciences, 18th Edition, Mack Publishing, p. 1288-1300 [1990]. Accordingly, in some embodiments, the extracts are formulated as a water based gel or paste, ointment, cream (anhydrous or hydrous), lotion (anhydrous or hydrous), emulsion, spray, solution, aerosol, stick (solid cream), liquid band aid, powder, inhalation spray, nasal spray, basal drops, cheek drops, sublingual drops, eye drops or sprays, ear drops or sprays, and transdermal patches.

It is contemplated that the compositions for topical application find use for both cosmetic and therapeutic purposes. In some embodiments, it is contemplated that the compositions described above are applied directly to the skin or other epithelial or epidermal surfaces of the body. The compositions may be applied one, two, three or more times each day as is appropriate for the indication. The amount applied is not generally important, but generally a composition comprising from about 0.001 µg to 10 grams of the extract (or components thereof) may be applied to a given surface of the body. As described above, the composition may comprise other components such as adjuvants, carriers, other active ingredients, etc.

In some embodiments, the invention relates to compositions that include preservatives and antioxidants (including vitamins) to prevent product deterioration preferably trisodium and tetrasodium edetate (EDTA) and tocopherol (vitamin E). In further embodiments the composition contains antimicrobials to fight bacteria preferably butyl, propyl, ethyl, and methyl parabens, DMDM hydantoin, methylisothiazolinone phenoxyethanol (also rose ether fragrance component), quaternium-15. In further embodiments, the composition contains thickeners and waxes used in stick products such as lipsticks and blushers preferably candelilla, carnauba, and microcrystalline waxes carbomer and polyethylene-thickeners. In further embodiments, the composition contains solvents to dilute preferably butylene glycol and propylene glycol, cyclomethicone (volatile silicone), ethanol (alcohol) and glycerin. In further embodiments, the composition contains emulsifiers to break up and refine preferably glyceryl monostearate (also pearlescent agent), lauramide DEA (also foam booster) and polysorbates. In some embodiments, the compositions contain color additives—synthetic organic colors derived from coal and petroleum sources preferably D&C Red No. 7 Calcium Lake (and other dyes that do not dissolve in water), iron oxides, mica (iridescent), and aminophenols. In further embodiments, the compositions contain pH adjusters to stabilize or adjust acids and bases preferably ammonium hydroxide—in skin peels and hair waving and straightening, citric acid—adjusts pH, and triethanolamine—pH adjuster used mostly in transparent soap. In further embodiments, the compositions contains agents preferably magnesium aluminum silicate—absorbent, anti-caking agent, silica (silicon dioxide)—absorbent, anti-caking, abrasive, sodium lauryl sulfate—detergent, stearic acid—cleansing, emulsifier, talc (powdered magnesium silicate)—absorbent, anti-caking, and zinc stearate—used in powder to improve texture, lubricates.

The composition includes the recited components and combinations thereof in a total amount of about 0.5 to 50 grams per liter, preferably about 3 to 10 grams per liter, although higher or lower concentrations are permissible. Such compositions being in the form of an emulsion, cream, salve or the like, the active materials being admixed with water, alkylene glycols, various oils natural and synthetic, petrolatum, preservatives, coloring agents, perfumes, and like ingredients conventional in the cosmetic arts.

The composition can be applied to the face, eyelids or other body parts in an amount varying with the individual. About 0.01 to 1, advantageously about 0.02 to 0.75 and preferably about 0.3 to 0.5, grams per $cm^2$ has been found useful but more or less can be used. The application can be once weekly or more often, even several times a day.

In accordance with the compositions and method of the present invention, the egg, embryo or stem cell extracts of the present invention may be administered in the form of a pharmaceutical composition additionally comprising a pharmaceutically acceptable carrier. One skilled in the art will appreciate that suitable methods of administering the extract compositions to an animal, such as a mammal, are available and, although more than one method can be used to administer a particular composition, a particular method and dosage can provide a more immediate and more effective reaction than others. Pharmaceutically acceptable carriers are also well known to those skilled in the art. The choice of carrier will be determined, in part, both by the particular composition and by the particular method used to administer the composition. Accordingly, there is a wide variety of suitable formulations of the pharmaceutical compositions of the present invention.

In some preferred embodiments, the formulations of this invention are designed for topical administration. Typical of such formulations are ointments, creams, and gels.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient (e.g., salmon egg extract or stem cell extract) is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (e.g., salmon egg extract or stem cell extract) customarily is added in an amount to achieve the desired concentration.

Gels comprise a base selected from an oleaginous base, water, or an emulsion-suspension base, such as described above. To the base is added a gelling agent which forms a matrix in the base, increasing its viscosity. Examples of gelling agents are hydroxypropyl cellulose, acrylic acid polymers, and the like. Customarily, the active ingredient (IGF-II) is added to the formulation at the desired concentration at a point preceding addition of the gelling agent.

Serums may be watery or thicker liquids, often (but not always) clear in color. Serums are water based making them light in consistency. They are easily and quickly absorbed into the skin and provide an excellent way to deliver topical ingredients including Vitamin C, peptides, alpha hydroxy acids, retinols. Serums may be layered under other serums as well as creams or lotions making them a very flexible product to incorporate into your skin care regimen. Serums are tolerated well by all skin types as long as the individual is not sensitive to any of the ingredients. Serums may include glycerol or glycerine. The amount of extract incorporated into the formulation of this invention is not critical; the concentration should only be in a range sufficient to permit ready application of the formulation to the wound area in an amount which will deliver the desired amount of extract.

The customary amount of formulation to be applied will depend upon concentration of the active ingredient in the formulation. In some embodiments, the amount of protein in the extract is determined. Then, a specific amount of the extract is included in the pharmaceutically acceptable carrier based on the amount of protein. Generally, the formulation will be applied to the wound in an amount affording from about 0.1 to about 500 μg of protein per $cm^2$ of skin. Preferably, the applied amount of protein will range from about 1 to about 300 μg/$cm^2$, more preferably, from about 5 to about 200 μg/$cm^2$. In other embodiments, a specific volume of extract is added to the pharmaceutically acceptable carrier. Accordingly, in some embodiments, the compositions of the present invention comprise on a volume/volume basis (volume of extract and volume of pharmaceutically acceptable carrier), for example, from about 0.001 to 50% extract, about 0.01 to 50% extract, about 0.1 to 50% extract, about 0.001 to 10% extract, about 0.01 to 10% extract, about 0.1 to 10% extract, about 0.001 to 5% extract, about 0.01 to 5% extract, about 0.1 to 5% extract, about 0.001 to 4% extract, about 0.01 to 4% extract, about 0.1 to 4% extract, about 0.001 to 2% extract, about 0.01 to 2% extract, about 0.1 to 2% extract, about 0.001 to 1% extract, about 0.01 to 1% extract, or about 0.1 to 1% extract.

The present invention may be formulated as necessary with additives used commonly in the pharmaceutical sciences, such as surfactants, oils and fats, polyhydric alcohols, lower alcohols, thickening agents, UV absorbents, light scattering agents, preservatives, antioxidants, antibiotics, chelating agents, pH regulators, flavoring agents, pigments and water.

Examples of surfactants include polyoxyethylene (hereinafter abbreviated as POE-branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monolaurate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE-dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic acids, salts of N-acylamino acids, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives and other amphoteric surfactants.

Examples of oils and fats include vegetable oils and fats such as castor-oil, olive oil, cacao oil, camellia oil, coconut oil, wood wax, jojoba oil, grape seed oil and avocado oil; animal oils and fats such as mink oil and egg yolk oil; waxes such as beeswax, whale wax, lanolin, carnauba wax and candelilla wax; hydrocarbons such as liquid paraffin, squalene, microcrystalline wax, ceresine wax, paraffin wax and vaseline; natural or synthetic fatty acids such as lauric acid, myristic acid, stearic acid, oleic acid, isostearic acid and behenic acid; natural or higher alcohols such as cetanol, stearyl alcohol, hexyldecanol, octyldecanol and lauryl alcohol; and esters such as isopropyl myristate, isopropyl palmitate, octyldodecyl myristate, octyldodecyl oleate and cholesterol oleate.

Examples of polyhydric alcohols include ethylene glycol, polyethylene glycol, propylene glycol, 1,3-butyrene glycol, 1,4-butyrene glycol, dipropylene glycol, glycerol, diglycerol, triglycerol, tetraglycerol and other polyglycerols, glucose, maltose, maltitose, sucrose, fructose, xylitose, sorbitol, maltotriose, threitol and erythritol.

Examples of thickening agents include naturally-occurring high molecular substances such as sodium alginate, xanthene gum, aluminum silicate, quince seed extract, gum tragacanth, starch, collagen and sodium hyaluronate; semi-synthetic high molecular substances such as methyl cellulose, hydroxyethyl cellulose, carboxymethyl cellulose, soluble starch and cationized cellulose; and synthetic high molecular substances such as carboxyvinyl polymer and polyvinyl alcohol.

Examples of UV absorbents include p-aminobenzoic acid, 2-ethoxyethyl p-methoxycinnamate, isopropyl p-methoxycinnamate, butylmethoxybenzoylmethane, glyceryl-mono-2-ethylhexanoyl-di-p-methoxybenzophenone, digalloyl trioleate, 2,2'-dihydroxy-4-methoxybenzophenone, ethyl-4-bishydroxypropylaminobenzoate, 2-ethylhexyl-2-cyano-3,3'-diphenyl acrylate, ethylhexyl p-methoxycinnamate, 2-ethylhexyl salicylate, glyceryl p-aminobenzoate, homomethyl salicylate, methyl o-aminobenzoate, 2-hydroxy-4-methoxybenzophenone, amyl p-dimethylaminobenzoate, 2-phenylbenzoimidazole-5-sulfonic acid and 2-hydroxy-4-methoxybenzophenone-5-sulfonic acid.

Examples of preservatives include benzoates, salicylates, sorbates, dehydroacetates, p-oxybenzoates, 2,4,4'-trichloro-2'-hydroxydiphenyl ether, 3,4,4'-trichlorocarbanilide, benzalkonium chloride, hinokitiol, resorcinol and ethanol.

Examples of antioxidants include tocopherol, ascorbic acid, butylhydroxyanisole, dibutylhydroxytoluene, nordihydroguaiaretic acid and propyl gallate.

Examples of chelating agents include sodium edetate and sodium citrate.

Examples of antibiotics include penicillin, neomycin, cephalothin, potassium permanganate, selenium sulfide, erythromycin, bacitracin, tethacyclin, chloramphenicol, vancomycin, nitrofurantoin, acrisorcin, chlorodontoin, and flucytosine.

Some of these additives function to enhance the efficacy of the composition by increasing the stability or percutaneous absorbability of the essential components of the present invention.

Also, any dosage form is acceptable, whether in solution, emulsion, powder dispersion, or others. Applicability is wide, including fundamental dosage forms such as lotions, emulsions, creams and gels.

In addition to those stated above, suitable vehicles, carriers and adjuvants include water, vaseline, petrolatum, mineral oil, vegetable oil, animal oil, organic and inorganic waxes, polymers such as xanthanes, gelatin, cellulose, collagen, starch, kaolin, carrageenan, gum arabic, synthetic polymers, alcohols, polyols, and the like. The carrier can also include sustained release carrier such as lypizomes, microsponges, microspheres, or microcapsules, aqueous base ointments, water in oil or oil in water emulsions, gels or the like.

The dose administered to an animal, particularly a human, in the context of the present invention should be sufficient to effect a therapeutic response over a reasonable time frame. The dose will be determined by the strength of the particular compositions employed and the condition of the person. The size of the dose and the frequency of application also will be determined by the existence, nature, and extent of any adverse side effects that may accompany the administration of a particular composition.

L. Uses

In some embodiments, the cell or extract compositions are useful for hydration (i.e., treating intravascular dehydration and edema in a wounds), waterproofing (i.e., compensate for hypovolemia in wounds), guarding against infection (i.e., protecting wound against infections), protection against oxidation (i.e., prevention of oxygen-free radical production during inflammatory reactions of ischemic tissue), wound healing (i.e., increased metabolism to aid in hypoxic conditions especially of burned skin or cells in anaerobic metabolism). In some preferred embodiments, the compositions are odorless (i.e., characterized by an absence of volatile carbon or nitrogen containing compounds).

In some embodiments, the invention relates to methods of using a plurality of compositions. In preferred embodiments, a first cream is used to loosen and/or dissolve cars by collagen dissolving agents or acids, such as lactic acid. A second cream with extracts or components thereof as well as other wound healing substances as described herein. In another preferred embodiment a laser, chemical peel, razor, acid, freezing, exfoliant and/or abrasive is used to remove scars or wrinkles followed by application of a cream with extracts or components thereof as well as other wound healing substances as described herein.

In some embodiments, the invention relates to a first composition preferably a cream that slows wound healing, reduces inflammation, and/or reduces scab formation. This composition is applied for several days. In preferred embodiments, the composition comprises a combination of one or more of anti-inflammatory agents, antihistamines, an extract component or components capable of dampening neutrophil migration and/or proliferation, an extract component or components the stimulate macrophages, phospholipases, arachidonic acid. In further embodiments, there is a water, lipid, protein content that provides vernix properties in the composition. In further embodiments, the components in the composition reduce activity of fibrogen cytokines. Preferably, the first composition is applied for about 1 to 3 days.

In another embodiment, the invention relates to a second composition preferably a cream that heals wounds by stimulating needed cells. Preferably this composition is applied to a subject after the first composition is applied. Preferably, the second composition is applied for about 3 to 14 days. This second composition contains components of cell and cell extracts that regulate collagenases, activate plasminogenases for clot dissolution, stimulate epithelializaiton, (i.e., migration, proliferation, dedifferentiation, redifferentiation), activate fibronectin and fibroblast growth factors, stimulate angiogenesis, reduce activity of fibrogenic cytokines and regulate genes such as TP53.

In another embodiment, the invention relates to a third composition preferably a cream. Preferably this composition is applied to a subject after the application of the second composition. This third composition functions to control collagen remodeling by collagen synthesis and destruction preferably by collegenases and metalloproteins and preferably collagan I and inactivate fibronectin, hyaluroinic acid and glycosaminoglycans, and dehydrate swelling. The third composition is preferably applied for about one to six weeks, following the application of the firs and second compositions. In some embodiments, a matrix is provided, such as a chitosan matrix, biodegradable polymer matrix, collagen matrix, or liquid band aid.

In some embodiments, the cell and/or extract composition is dispersed in a biocompatible liquid was applied to a physiologically acceptable support structure in a liquid state to form a film. A film is defined herein as a surface and/or interfacial covering, in either a liquid or a solid state, with temperature-dependant properties. Film-forming techniques include but are not limited to spraying, extruding, blowing, pouring, evaporating, coating and painting. The dispersion is presented as droplets that coalesce to form a film upon encountering the support.

In an alternate embodiment, a preformed film is applied to a support. The physiologically acceptable support structure is one that can withstand sterilization, preferably by standard sterilization techniques known to one skilled in the art such as exposure to gamma radiation, autoclaving, and so on. The support structure is not limited to a particular composition or configuration and, depending upon its use, may or may not be sterilized and may take various forms.

In another embodiment, the film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II®. (Sterling Drug Inc., New York, N.Y.) or circular nylon filters of suitable porosity (Micron Separations Inc., Westboro, Mass.). Other support materials, however, could also be used to practice the invention.

In another embodiment, the film is used to treat or prevent injury due to substance exposure or trauma, and may be applied to various materials for placement either in direct contact or indirect contact with an exposed skin site. The skin site may be intact (e.g., normal skin) or may be compromised, defined as skin that is damaged or that lacks at least some of the stratum corneum (e.g., skin damaged by exposure to the agent in question, another agent, the presence of a pathological condition such as a rash or contact dermatitis, a physical trauma such as a cut, wound, or abrasion, a underdeveloped skin such as occurs in a preterm infant, conditions in which either all or part of the epidermis is exposed, conditions in which part of the dermis has been removed such as partial thickness wounds encountered in resurfacing procedures such as chemical peels, dermabrasions, and laser resurfacing, etc.).

The support structure may be permeable to physical and/or chemical agents, and may take a variety of forms, depending upon its purpose and the extent of the area requiring dressing or treatment. The film may be applied to various synthetics such as thermoplastic films, blown films and breathable films, and various natural and synthetic fabric compositions such as woven, non-woven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

In some embodiments, the invention relates to regeneration of the function of skin with a desired cosmetic appearance and the prevention of skin damage. In further embodiments, early scar formation is prevented by application of a scar prevention composition when the wound is formed. In further embodiments, stimulating the rejuvenation and regeneration of stressed and aging skin prevents wrinkle formation. In further embodiments, the product is applied intermittently to slow the continual damage process that occurs as skin ages.

The skin has two main layers, the epidermis and dermis. Below these is a layer of subcutaneous ('under the skin') fat. The outer surface of the skin is the epidermis, which itself contains several layers, the basal cell layer, the spinous layer, the granular cell layer, and the stratum corneum. The deepest layer of the epidermis is the basal cell layer. Here cells are continually dividing to produce plump new skin cells. These cells move towards the skin surface, pushed upward by the dividing cells below them. Blood vessels in the dermis, which is below the basal cell layer, supply nutrients to support this active growth of new skin cells. As the basal cells move upwards and away from their blood supply, their cell content and shape change. Cells above the basal cell layer become more irregular in shape and form the spinous layer. Above this, cells move into the granular layer. Being distant from the blood supply in the dermis, the cells begin to die and accumulate a substance called keratin.

The stratum corneum ('horny layer') is the top layer of the epidermis—it is the layer of the skin that we see from the outside. Cells here are flat and scale-like ('squamous') in shape. These cells are dead, contain a lot of keratin and are arranged in overlapping layers that impart a tough and waterproof character to the skin's surface. Dead skin cells are continually shed from the skin's surface. This is balanced by the dividing cells in the basal cell layer, thereby producing a state of constant renewal. Also in the basal cell layer are cells that produce melanin. Melanin is a pigment that is absorbed into the dividing skin cells to help protect them against damage from sunlight (ultraviolet light). The amount of melanin in your skin is determined by genetic makeup and one's exposure to sunlight. The more melanin pigment present, the darker the color of your skin.

Below the epidermis is the layer called the dermis. The top layer of the dermis, the one directly below the epidermis, has many ridges called papillae. On the fingertips, the skin's surface follows this pattern of ridges to create our individual fingerprints. The dermis contains a variable amount of fat, and also collagen and elastin fibres that provide strength and flexibility to the skin. In an older person the elastin fibres fragment and much of the skin's elastic quality is lost. This, along with the loss of subcutaneous fat, results in wrinkles Blood vessels supply nutrients to the dividing cells in the basal layer and remove any waste products. They also help maintain body temperature by dilating and carrying more blood when the body needs to lose heat from its surface; they narrow and carry less blood when the body needs to limit the amount of heat lost at its surface. The skin also contains a number of nerves and glands.

Overall skin quality and appearance can be affected by a variety of disorders, including aging, photoaging, acne, enlarged pores, and scarring. The intrinsic process of chronological aging results from thinning of the epidermis and dermis and loss of elasticity. This process affects all layers of the face, including subcutaneous tissue, the musculofascial system, the superficial musculoaponeurotic system, and the facial skeleton. The result is bony resorption, atrophy of subcutaneous fat, attenuation of the musculofibrous system, and alterations of skin surface. The dermal-epidermal junction flattens, which results in loss of rete ridges and a thinner appearance to the epidermis. The dermis also becomes thin, with a decrease in elastic fibers, collagen production, vascularity, and ground substance. The biochemical alterations in collagen and elastin result in a dermis that is more lax yet less elastic and resilient. Collectively, these changes result in fine wrinkling of the skin and sagging of the tissues that overlay the facial skeleton.

In some embodiments, the invention relates to composition comprising extracts that can stimulate skin cells to regenerate spontaneously. In additional embodiments, cells with elongated telomeres made in situ from the subject's own cells are reintroduced to the subject.

Many modalities can resurface the skin to improve skin quality, reduce age spots, soften fine lines, and treat acne or other scars. Modalities include traditional dermabrasion, chemical peeling, laser resurfacing, and microdermabrasion. The techniques attempt to remove the outer layers of skin with the idea that stimulating new growth will improve appearance. The initial evaluation of skin condition is typically accomplished using Fitzpatrick's scale of sun-reactive skin types, which denotes patients' reactions to ultraviolet radiation and existing degree of pigmentation. Type I patients always burn and never tan. Type II patients tan only with difficulty and usually burn. Type III patients tan but sometimes burn. Type IV patients rarely burn and tan with ease. Type V patients tan very easily and very rarely burn. Type VI patients tan very easily and never burn.

Chemical peeling is the chemical removal of layers of skin to improve dermatologic defects. The mechanism of action of peeling agents is relatively straightforward. Stronger agents such as phenol (with various additives such as croton oil and glycerin) and trichloroacetic acid (TCA) produce a chemical necrosis of the skin to variable depths, depending on a number of controlled and uncontrolled variables. The weaker agents change the pH sufficiently to cause a superficial shock to the cells and, depending on many variables, cell injury or death. When used with a moisturizer, the acid acts simply to cause cellular and intercellular swelling and plumping, leading to transient increase in cell and matrix size and lessening of fine lines and rhytides. Sequential treatments lead to exfoliation and a smoother complexion. Continued irritation can lead to many of the same effects of tretinoin or retinoid treatment (i.e., increased thickness of dermis, increased blood flow to skin). The phenol peel "The Baker formula" is phenol USP 88% 3 cm$^3$ 49%; distilled water 2 cm$^3$ 44%; croton oil 3 drops 2.1%; and Septisol 8 drops 4.5%.

The microdermabrasion technique abrades the skin with a high-pressure flow of crystals. Microdermabrasion is most effective with superficial skin conditions because it produces a superficial depth of injury. Superficial skin conditions include early photoaging, fine lines, and superficial scarring. Microdermabrasion is accomplished by placing the skin under tension so that an effective vacuum is achieved. Typically, stretching the treatment area with the nondominant hand and using the dominant hand to guide the handpiece is the method used to achieve this effect. When treating the neck, the neck is placed in extension to assist in skin tension. The handpiece is moved over the treatment area in a single, smooth stroke, which can then be repeated. The pressure of the crystal stream is controlled with a foot pedal. Thicker skin, such as that on the forehead, chin, and nose, can be treated more aggressively (ie, adjust the speed of handpiece movement or number of passes). Decrease the pressure when treating the thinner skin of the lower eyelids and upper cheek. Vertically orient all strokes when treating the neck.

Laser skin resurfacing (LSR) can be performed as an isolated procedure or as an adjunct to procedures such as transconjunctival blepharoplasty (TCB), facelift, and endoscopic browlift. The laser allows for precise control of ablation depth, and it permits the surgeon to vary these depths as needed. In addition to such precision, LSR causes favorable heating of the dermis, which tightens collagen fibers and stimulates neocollagen secretion by fibroblasts. Two laser wavelengths are preferred for facial skin resurfacing: pulsed carbon dioxide and erbium:yttrium-aluminum-garnet (Er:YAG). Each Er:YAG pulse removes only 25-30 micrometers of tissue compared to the pulsed carbon dioxide, which removes 50-100 micrometers. The Er:YAG produces less collateral dermal energy because the thermal conduction is approximately 5 micrometers; pulsed carbon dioxide is 30-50 micrometers. The laser output of Er:YAG is directly absorbed by collagen and dermal proteins, whereas the carbon dioxide laser vaporizes extracellular water in the dermis. Each Er:YAG pass generates the same amount of ablation, whereas the pulsed carbon dioxide generates a decreased vaporization depth with each pass.

The composition of the present invention also finds use in wound healing. A wound is a break in the skin (the outer layer of skin is called the epidermis). Wounds are usually caused by cuts or scrapes. Healing is a response to the injury that sets into motion a sequence of events. With the exception of bone, all tissues heal with some scarring. The object of proper care is to minimize the possibility of infection and scarring.

Pressure ulcers are chronic wounds caused by unrelieved pressure that results in tissue damage. The ulcers are staged from I to IV, according to the level of tissue damage observed. Pressure ulcers are most common in hospitalized patients, nursing home patients and those with spinal cord injuries. The standard of care for pressure ulcers includes interval dressing changes, pressure relief, repositioning, physical strengthening, nutritional support and infection management. If the wound becomes severe, surgical interventions include wound debridement and skin-flap, muscle-flap or free-flap reconstruction.

The present invention also finds use for the treatment of various skin disorders. Uneven skin, discoloration, and growths can be caused by a variety of factors including genetics, exposure to sun, and/or use of medications. Callus formation (Clavus) is a thickening of the skin due to intermittent pressure and frictional forces. The shape of the hands and feet are important in clavus formation. Specifically, the bony prominences of the metacarpophalangeal and metatarsophalangeal joints often are shaped in such a way as to induce overlying skin friction. As clavus formation ensues, friction against the footwear is likely to perpetuate hyperkeratosis. Toe deformity, including contractures and claw, hammer, and mallet-shaped toes, may contribute to pathogenesis. Bunionettes, ie, callosities over the lateral fifth metatarsal head, may be associated neuritic symptoms due to compression of the underlying lateral digital nerves. Furthermore, Morton toe, in which the second toe is longer than the first toe, occurs in 25% of the population; this may be one of the most important pathogenic factors in a callus of the common second metatarsal head, ie, an intractable plantar keratosis.

Moles (Nevi) are nests of melanocytes that are in contact with each other. They typically start formation during early childhood. It has been suggested that they form in response to sun exposure. However, a genetic factor is clearly involved in nevi. Some kinships express an autosomal dominant condition in which members have a large number of large nevi, sometimes more than 150 nevi scattered over the integument. Nevi have been observed to develop rapidly after blistering events, such as second-degree thermal burns or sunburns; toxic epidermal necrolysis; and in persons with genetic blistering diseases, such as epidermolysis bullosa. Growth factors, such as basic fibroblast growth factor, have been suggested to be released by proliferation keratinocytes and to stimulate melanocyte proliferation. Melanocytic nevi are benign neoplasms or hamartomas composed of mostly melanocytes, the pigment-producing cells that colonize the epidermis. Melanocytes are derived from the neural crest and migrate during embryologic development to selected ectodermal sites (primarily the skin and the CNS) but also to the eyes and the ears. Ectopic melanocytes have been identified at autopsy in the gastrointestinal and genitourinary tracts. Congenital melanocytic nevi are thought to represent an anomaly in embryogenesis and as such could be considered a malformation or a hamartoma. In contrast, most acquired melanocytic nevi are considered to be benign neoplastic proliferations.

Atypical moles/dysplastic nevi are acquired melanocytic lesions of the skin whose clinical and histologic definitions are still evolving. Atypical moles differ from common acquired melanocytic nevi in several respects, including diameter and lack of pigment uniformity Birth marks (Capillary hemangiomas) are one of the most common benign orbital tumors of infancy. They are benign endothelial cell neoplasms that are typically absent at birth and characteristically have rapid growth in infancy with spontaneous involution later in life. This is in contrast to another known group of childhood vascular anomalies, vascular malformations. Vascular malformations, such as lymphangiomas and arteriovenous malformations, are present at birth and are characterized by very slow growth with persistence into adult life.

Striae distensae (Stretch marks) affect skin that is subjected to continuous and progressive stretching; increased stress is placed on the connective tissue due to increased size of the various parts of the body. It occurs on the abdomen and the breasts of pregnant women, on the shoulders of body builders, in adolescents undergoing their growth spurt, and in individuals who are overweight. Skin distension apparently leads to excessive mast cell degranulation with subsequent damage of collagen and elastin. Prolonged use of oral or topical corticosteroids or Cushing syndrome (increased adrenal cortical activity) leads to the development of striae.

Acne manifestation is defined by the distribution of the pilosebaceous glands. Adolescence causes endocrine maturation of the adnexal elements, resulting in an accumulation of cellular products within the ductile systems. In addition to the cellular products are coexistent microorganisms, most commonly *Propionibacterium acnes* and *Staphylococcus epidermidis*.

Rosacea is a common condition characterized by symptoms of facial flushing and a spectrum of clinical signs, including erythema, telangiectasia, coarseness of skin, and an inflammatory papulopustular eruption resembling acne. Rosacea is defined by persistent erythema of the central portion of the face lasting for at least 3 months. Supporting criteria include flushing, papules, pustules, and telangiectasias on the convex surfaces. Secondary characteristics are burning and stinging, edema, plaques, a dry appearance, ocular manifestations, and phymatous changes. Perioral dermatitis (POD) is a chronic papulopustular facial dermatitis. It mostly occurs in young women. The clinical and histologic features of the lesions resemble those of rosacea.

Warts are benign proliferations of skin and mucosa caused by the human papilloma virus (HPV). Currently, more than 100 types of HPV have been identified. Certain HPV types tend to occur at particular anatomic sites; however, warts of any HPV type may occur at any site. The primary clinical manifestations of HPV infection include common warts, genital warts, flat warts, and deep palmoplantar warts (myrmecia). Less common manifestations of HPV infection include focal epithelial hyperplasia (Heck disease), epidermodysplasia verruciformis, and plantar cysts. Warts are transmitted by direct or indirect contact, and predisposing factors include disruption to the normal epithelial barrier. Treatment can be difficult, with frequent failures and recurrences.

Genital warts are a result of human papillomavirus (HPV) infection acquired by inoculation of the virus into the epidermis via defects in the epithelium (eg, maceration of the skin) Autoinoculation of virus into opposed lesions is common. Spread of HPV infection is usually through skin-associated virus and not from blood-borne infection.

Bowenoid papulosis (BP) occur on the genitalia of both sexes in sexually active people. BP is manifested as papules that are induced virally by human papillomavirus (HPV) and demonstrate a distinctive histopathology (bowenoid dysplasia).

Psoriasis is characterized by exceedingly rapid turnover of skin and appears as a chronic, bilaterally symmetric, erythematous plaquelike lesion with a silvery scale covering. The lesions classically are located over the extensor surfaces, including the elbows, knees, back, and scalp. Confluent generalized lesions also may occur.

In Von Recklinghausen disease multiple neural tumors appear on the body. Numerous pigmented skin lesions occur. The classic café au lait spots predominate. Additionally, pigmented iris hamartomas (i.e., Lisch nodules) are common. Bone lesions and intracranial and GI lesions and symptoms may be identified.

Necrobiosis lipoidica diabeticorum is a plaquelike, depressed, atrophic yellow lesion typically found in patients with diabetes. It has a strong association with diabetes and actually may be a clinical prodrome of the onset of the disease systemically. It rarely is found in locations other than the lower extremities and seldom is found in the absence of diabetes. The lesion tends to progress from a red plaquelike area to one with atrophy that occasionally may ulcerate.

Seborrheic dermatitis is a papulosquamous disorder patterned on the sebum-rich areas of the scalp, face, and trunk. In addition to sebum, this dermatitis is linked to Malassezia, immunologic abnormalities, and activation of complement.

Seborrheic keratosis (also known as seborrheic wart, senile wart, and basal cell papilloma) is a common benign tumor in advanced and middle-aged persons. It is typically a raised papular lesion of variable color from light to dark brown. Seborrheic keratosis may be smooth or wartlike with visible pitting. Common sites include the face, trunk, and extremities. The lesion also may be pedunculated or sessile. A variant known as dermatosis papulosa nigra occurs over the forehead and malar regions of individuals with black skin.

Acrochordons (also known as skin tag, fibroepithelial polyp, fibroma molle, and fibroepithelial papilloma) occasionally are associated with pregnancy, diabetes mellitus, and intestinal polyposis syndromes. They tend to be located in the intertriginous areas of the axilla, groin, and inframammary regions as well as in the low cervical area along the collar line. They are soft fleshy papules and usually, although not necessarily, pedunculated.

Actinic keratosis is the most common sun-related growth. Actinic keratoses are chiefly found on the sun-exposed areas of the face, the ears, the forearms, and the dorsum of the hands. However, they may occur on any area that is chronically or repeatedly exposed to the sun, such as the back, the chest, and the legs. They usually appear as multiple discrete, flat or elevated, verrucous, keratotic lesions. Lesions typically have an erythematous base covered by scale (hyperkeratosis). They are usually 3-10 mm in diameter and gradually enlarge into broader, more elevated lesions. With time, actinic keratoses may develop into invasive cutaneous horns or skin cancers. Histologically, the epidermal changes are characterized by acanthosis, parakeratosis, and dyskeratoses. Cellular atypia is present, and the keratinocytes vary in size and shape. Mitotic figures are common.

The compositions of the present invention also find use in the treatment of burns. Sunburn is an acute cutaneous inflammatory reaction that follows excessive exposure of the skin to ultraviolet radiation (UVR). Exposure to solar radiation has the beneficial effects of stimulating the cutaneous synthesis of vitamin D and providing radiant warmth. Unfortunately, when the skin is subjected to excessive radiation in the ultraviolet range (wavelength<400 nm), deleterious effects may occur. The most common is acute sunburn or solar erythema. Eyes, particularly the cornea (the clear window of tissue on the front of the eyeball), can be damaged easily by exposure to ultraviolet radiation from the sun and from other sources of ultraviolet light, such as a welder's arc, a photographer's flood lamps, a sun lamp, or even a halogen desk lamp.

Epithelialization, angiogenesis, granulation tissue formation, and collagen deposition are involved in the proliferation phase anabolic portion of wound healing. Epithelialization occurs early in wound repair. If the basement membrane remains intact, the epithelial cells migrate upwards in the normal pattern. This is equivalent to a first-degree skin burn. The epithelial progenitor cells remain intact below the wound, and the normal layers of epidermis are restored in 2-3 days. If the basement membrane has been destroyed, similar to a second- or third-degree burn, then the wound is reepithelialized from the normal cells in the periphery and from the skin appendages, if intact (eg, hair follicles, sweat glands)

Angiogenesis, stimulated by TNF-alpha, is marked by endothelial cell migration and capillary formation. The new capillaries deliver nutrients to the wound and help maintain the granulation tissue bed. The migration of capillaries into the wound bed is critical for proper wound healing. The granulation phase and tissue deposition require nutrients supplied by the capillaries, and failure for this to occur results in a chronically unhealed wound. Mechanisms for modifying angiogenesis are under study and have significant potential to improve the healing process.

During granulation tissue formation, fibroblasts differentiate and produce ground substance and then collagen. The ground substance is deposited into the wound bed; collagen is then deposited as the wound undergoes the final phase of repair. Many different cytokines are involved in the proliferative phase of wound repair. The steps and the exact mechanism of control are not well understood. Some of the cytokines include PDGF, insulinlike growth factor (IGF), and EGF.

During a remodeling stage, the framework (collagen) becomes more organized making the tissue stronger. The blood vessel density becomes less, and the wound begins to lose its pinkish color. Over the course of 6 months, the area increases in strength, eventually reaching 70% of the strength of uninjured skin. In the maturational phase, the wound undergoes contraction, ultimately resulting in a smaller amount of apparent scar tissue. The entire process is a dynamic continuum with an overlap of each phase and continued remodeling. The wound reaches maximal strength at one year, with a tensile strength that is 30% of normal skin. Collagen deposition continues for a prolonged period, but the net increase in collagen deposition plateaus after 21 days.

Epithelialization is the process of laying down new skin, or epithelial, cells. The skin forms a protective barrier between the outer environment and the body. Its primary purpose is to protect against excessive water loss and bacteria. Reconstruction of this layer begins within a few hours of the injury and is complete within 24-48 hours in a clean, sutured (stitched) wound. Open wounds may take 7-10 days because the inflammatory process is prolonged, which contributes to scarring. Scarring occurs when the injury extends beyond the deep layer of the skin (into the dermis).

Collagen production is elevated in keloid biopsy samples and in cultured fibroblasts derived from keloids. Increased collagen production by cultured fibroblasts derived from keloids persists throughout their in vitro life span; they do not revert to normal after transfer of the lesion to culture. No significant differences in DNA content or cellularity are found when keloid dermis is compared with normal dermis. This suggests that each fibroblast is producing more collagen rather than an increase occurring in the number of fibroblasts producing a normal amount of collagen. In keloid formation, excessive collagen production by fibroblasts is likely due to the wound environment.

Widened scar formation is thought to result from wound edge separation with tension perpendicular to the healing skin wound. A state of tension exists naturally in skin; wounded skin gapes and becomes elliptical rather than round. When a wound is closed opposite to the lines of tension, the chance of widened scar formation is increased.

Upon clinical examination, keloids and hypertrophic scars are raised above the skin level. Hypertrophic scars are self-limited; they hypertrophy within the confines of the wound. Initially, hypertrophied scars can be raised, red, pruritic, and even painful; however, over time, they become pale and flat. Hypertrophied scars appear worst at 2 weeks to 2 months. Keloid scars can be differentiated from hypertrophic scars by their spread beyond the original wound. Keloid scars tend to remain red, pruritic, and painful for many months to years until menopause. Patients usually have a personal or familial history of keloid formation. Different from hypertrophic and keloid scars, widened scars are flat and sometimes depressed. With adequate wound maturation, these wounds fade to the pigment of the surrounding uninjured skin. Widened scars are not usually red or pruritic.

The relaxed skin tension lines follow furrows formed when the skin is relaxed. Unlike wrinkles, they are not visible features of the skin. They are merely derived from the furrows produced by pinching on the skin. These furrows are produced preferably with pinching perpendicular to the lines. When the skin is pinched oblique to the relaxed skin tension lines, an S-shaped pattern is created. Fewer and higher furrows are created if skin is pinched parallel to the lines. Closing incisions opposite to the relaxed skin tension lines can increase the risk of widened or hypertrophic scar formation.

A potential relative contraindication to scar revision surgery exists when the scar is a keloid because of the risk of worsening the scar. Sometimes, when keloids recur, they become larger than the original. Widened scars can be easily differentiated from hypertrophic and keloid scars based on findings from a physical examination. Widened scars are flat and sometimes even depressed. Hypertrophic scars and keloids are indistinguishable under light microscopy. However, there are a number of differences when viewed under an electron microscope and when evaluated immunochemically. Keloids contain thick collagen fibers with increased epidermal hyaluronic content, whereas hypertrophic scars exhibit nodular structures with fine collagen fibers and increased levels of alpha smooth muscle actin. The collagen in both keloids and hypertrophic scars is organized in discrete nodules, frequently obliterating the rete pegs in the papillary dermis of the lesions. While collagen in normal dermis is arranged in discrete fascicles separated by considerable interstitial space, collagen nodules in keloids and in hypertrophic scars appear avascular and unidirectional and are aligned in a highly stressed configuration.

Different nonsurgical options treat abnormal scars. Pressure is thought to decrease tissue metabolism and increase collagen breakdown within the wound. The different methods of applying pressure include the use of elastic bandages (ACE wraps), thromboembolic disease stockings, or Isotoner-type gloves on extremities. Alternatively, custom-fitted compression garments can be used to apply pressure to the more difficult areas, including the neck and torso. Because these devices are uncomfortable, patient compliance varies. Unfortunately, for optimal results, these devices must be used for 6-12 months during the maturation of the wound.

Silicone gel can be used to treat abnormal scars. Silicone gel is shown to significantly decrease scar volume when used over time particularly for hypertrophic scar formation. The effect of the silicone gel on the scar is believed to be due to wound hydration. The silicone gel is applied to the wound for at least 12 h/d. Patients find it more appealing to apply the silicone to their wounds at night. Silicone gel is gaining popularity because it can be applied to a smaller area for 12 h/d, usually at night. However, skin breakdown, rashes, and difficulty with wound adherence can lead to disuse.

Steroid injections have become a common nonsurgical option in the treatment of problem scars. The steroid used for intralesional injection is triamcinolone (Kenalog). Triamcinolone injections have been the standard treatment to induce flattening, fading, and decreased symptomatology of hypertrophied scars. These injections can be administered as soon as a problem scar is identified. The dose of the injection can vary from 10-120 mg, depending on the size of the scar.

One may make use of a triamcinolone injection for thin-to-wide hypertrophied scars and silicone for very wide hypertrophied scars. Some patients prefer triamcinolone injections to avoid applying and wearing the silicone every day for 6-9 months, especially on body areas where adherence is poor. Adverse effects of triamcinolone injections include hypopigmentation and subcutaneous atrophy. Other nonsurgical options include corticosteroid intralesional injections, vitamin E therapy, zinc oxide therapy, antineoplastic agents, and immunotherapy.

If nonoperative measures are unsuccessful in the treatment of abnormal scars, operative intervention can be considered. Closing wounds to orient the wound along the relaxed skin tension lines is important. A standard practice often used rather subconsciously after excision of a lesion involves assessing the direction of least tension based on the configuration of the edges of the wound or by pinching the wound.

The first-line procedure used for scar revision is fusiform excision. In general, fusiform excision does not require lengthening the scar. In order to avoid canine auricles, ensure the wound has a length-to-width ratio of 4:1. Fusiform excision is preferred for short wounds oriented along relaxed skin tension lines. The Millard flap procedure is similar to fusiform excision, but it involves preserving the scar and its connection to the underlying fat. The skin is incised in a fusiform fashion around the scar to the subcutaneous level. The scar is then deepithelialized, and the skin edges are approximated over the deepithelialized scar. The Millard flap technique is preferred for widened, depressed scars.

Scars not oriented along the relaxed skin tension lines can be modified with a Z-plasty procedure. Limbs of equal length are created for the Z plasty. The angle of the Z dictates the length of scar tension distribution and elongation (eg, 30° for 25%, 45° for 50%, 60° for 75%, 75° for 100%, 90° for 120%). The W-plasty technique for scar revision is similar to Z plasty because of the result of breaking up a straight-line scar into a pattern that is less conspicuous. Similar to a fusiform excision, W plasty involves the removal of skin; therefore, avoid this method if significant tension is present across the wound edges. W-plasty scar revision is preferred for scars along relaxed skin tension lines; scars with a bowstring contracture; short, depressed scars; and facial scars.

Tissue expansion and serial excision can be considered for larger scar revisions when excess wound tension is predicted. If more than 2 serial excisions are expected, tissue expansion is preferred. Finally, other procedures that have been described to treat scars include dermabrasion, cryosurgery, and laser therapy. Widened scars may be treated differently than hypertrophied scars. Widened scars can be flat or even depressed. Therefore, the administration of intralesional steroids is not preferred; these agents might worsen the depression. Widened scars are preferably treated with the Millard 2-flap technique over a deepithelialized scar. This technique provides soft tissue fill under the approximated wound edges. Furthermore, if the widened scar recurs, the risk for another recurrence may be minimized by reorienting the wound tension along the lines of relaxed skin tension. Other adjuncts described in the treatment of widened scars include the injection of fat grafts or other tissue substitutes. When oriented close to the relaxed skin tension lines, hypertrophic scars can be excised in a fusiform fashion. If the hypertrophic scar developed because of excessive tension across the wound as a result of unfavorable wound orientation, Z plasty can sometimes help reorient the wound to distribute tension in a different direction to minimize the risk of recurrence.

Postoperatively, compression garments and silicone gel are preferred for 4-6 months to decrease the risk of recurrence. Patients are encouraged to refrain from strenuous activities for at least 6 weeks, until which time the wound achieves approximately 80% original wound tensile strength. Patients are monitored for 6 months postoperatively to detect and potentially circumvent recurrences early. Postoperatively, patients are at risk for hypertrophic scar and widened scar recurrence. Other risks include infection, hematoma, seroma, and painful or unattractive scarring. The risk of recurrence is significant for both hypertrophic and widened scars, and it is increased with repeat operations. Wound healing requires approximately 1 year, during which time the surgeon and patient should observe for and expect improvement. Once the scar has had an opportunity to mature, scar revision can be considered.

In some embodiments of the present invention, compositions comprising cell extracts are utilized to improve any area of the person visible and contributing to cosmetic appearance of a person, including but not limited to skin, hair, nails, teeth, subcutaneous fat, cartilage, muscle and skeletal structures. The described gene-gun and microinjection delivery methods are contemplated to introduce extracts or extract components to structures below the surface skin of a person.

This invention relates to prevention of deterioration, damage and malfunction of cells and tissues, and to promote, improve and exceed cellular function in order to promote, improve and exceed appearance, vitality and health by treating cells and tissues with differentiable cells, cell or egg extracts, or components of said extracts including signaling molecules, peptides, carbohydrates, lipids or nucleic acids.

The current invention contemplates the assessment of a persons needs for healing, regeneration or repair of damage by several means, including but not limited to analysis and measurements of visible surfaces, skin pH, thickness, structure and elasticity of skin layers, analysis of blood or tissue samples by microchip, RT-PCR, Mass spectrometry, high pressure liquid chromatography, ELISA-assays, RNA analysis, analysis of accumulation of DNA damage or defective genes by DNA sequencing, assessment of internal organ and tissue health by X-ray imaging, ultrasound imaging, computed tomography (CT), magnetic resonance imaging (MRI), positron emission tomography (PET).

Subcutaneous fat contributes to the cosmetic appearance of a person, and is redistributed during ageing, by smoking and in a number of diseases, including HIV and diabetes as well as in burn-victims. The human immunodeficiency virus (HIV)-lipodystrophy syndrome is associated with fat redistribution and metabolic abnormalities, including insulin resistance. Increased intramyocellular lipid (IMCL) concentrations are thought to contribute to insulin resistance, being linked to metabolic and body composition variables. Among HIV-infected subjects, calf subcutaneous fat area and extremity fat are reduced. Extremity fat is significantly associated with IMCL among HIV-infected patients, controlling for visceral abdominal fat, abdominal subcutaneous fat, and antiretroviral medications in a regression model. Increased IMCL in HIV-infected women with a mixed lipodystrophy pattern are most significantly associated with reduced extremity fat. (Torriani M et al., J Appl Physiol. 2006 February; 100(2):609-14. Epub 2005 Oct. 13). Saturation of the subcutaneous fat depot is the primary event in the pathophysiology of insulin resistance in the majority of patients and postulate that this seminal event may lead to the development of hypertension, hypertriglyceridemia and depressed HDL levels (i.e., the metabolic syndrome). There are no current effective means to redistribute subcutaneous fat in such persons, current treatment include (1) weight loss with differing responses seen with regards to insulin resistance depending on the size of the fat depot; (2) peroxisome proliferator activated receptor gamma agonists, such as thiazoledinediones which expand the subcutaneous fat depot, (3) expanding alternate storage sites for triglycerides by a variety of techniques, such as resistance training-induced muscle hypertrophy, may also improve insulin resistance; (4) drugs, such as beta 3 adrenergic receptor agonists which promote lipolysis may increase insulin resistance by releasing free fatty acids into the circulation. Inhibitors of the beta oxidation of free fatty acids (e.g., carnitine palmitoyl transferase inhibitors) may cause insulin resistance by sparing fat and (5) liposuction, by reducing the size of the subcutaneous fat depot may worsen insulin resistance, thus increasing the risk of type 2 diabetes mellitus (Cherian M A, Santoro T J, Med. Hypotheses. 2005 Dec. 14; [Epub ahead of print]).

Alterations in subcutaneous fat and skin condition due to hormone changes that occur during ageing and disease are also contemplated areas of use for this invention.

Effects of ovarian and other steroids are important to the metabolism of skin and hair, the changes in body composition and the alterations of the subcutaneous fat distribution throughout life. So called aesthetic endocrinology accesses deficiency or excess of ovarian steroids that lead to different problems skin and hair and other non-genital, i.e., obesity and cellulite. Sex steroids are small molecules that are transported into the skin by topical application when properly formulated, and are contemplated to be added to the extracts presented in this invention in order to achieve local effects but to avoid systemic reactions. Estrogens, delivered orally or topically, may counteract the aging of the skin especially post-menopause. Estrogen alone is not sufficient for reconstitution of juvenile skin but may slow the skin aging process. The hitherto only successful treatment of hair loss in women is by application of the non-hormonal compound minoxidil, and compositions contemplated by this invention may serve to be a different way of treating hair loss. Indeed, the compositions contemplated may stimulate hair sack follicles to regrow or increase the rate and quality of hair, as well as nails. Estrogens also contribute to hirsutism (the excessive growth of thick dark hair in locations where hair growth in women usually is minimal or absent), acne and changes in body composition. (Gruber C J, et al., Current concepts in aesthetic endocrinology. Gynecol Endocrinol. 2002 December; 16(6):431-41). The compositions in the present invention are additionally contemplated for use in hair loss and baldness in males which may be caused by hormones, diet, cancer, chronic illness or stress.

It is contemplated that the present invention can be used to regulate hair growth by stimulating or modulating hair follicle cells to either reduce or enhance or regenerate hair growth in desired areas by topical or sub-dermal applications.

This invention is also useful in the treatment of cellulite. Cellulite is a common term used to describe superficial pockets of trapped fat, which cause uneven dimpling or "orange peel" skin. It appears in 90% of post-adolescent women and is rarely seen in men. Common but not exclusive areas where cellulite is found, are the thighs, buttocks, and the abdomen. Contrary to popular belief, cellulite is not related to obesity, since it occurs in overweight, normal, and thin women. Cellulite can be aided by mechanized devices with motorized rollers and regulated suction. This non-surgical and non-invasive device creates a symmetrical skin fold, which allows for deep tissue mobilization to occur and results in reduction of cellulite and loss of inches. The present invention contemplates application of extracts topically or subcutaneously to regulate the distribution of subcutaneous fat deposits and improve the cosmetic appearance of areas affected by cellulite.

It is contemplated that the present invention may be useful for the repair or rejuvenation or de novo formation of damaged tissues, organs and cells beneath the skin, including all internal organs and tissues, including but not limited to muscle, fat, cartilage, bone, connective tissue, spleen, liver, pancreas, lungs and nervous tissue. Damages to the internal tissues or organs may be induced by i.e. accidents, diseases, medication, cancer, radiation and surgery.

When the body is exposed to high doses of radiation, a complex biological response is initiated that may lead to multi-organ failure (MOF). MOF begins with energy deposits in cellular targets and is propagated and amplified by the tissue response to cell damage. The biology of wound healing is at the root of MOF following surgical trauma, inflammation is the basis for MOF in sepsis, and the biology of the irradiated tissue initiates radiogenic MOF. Tissue response to radiation damage has been suggested to be initiated and co-ordinated by extracellular signaling. It has been demonstrated that transforming growth factor-β1 orchestrates the biology of irradiated tissue as a tissue level sensor of oxidative stress, and is integral to the cellular DNA damage response.
(Barcellos-Hoff M H. How tissues respond to damage at the cellular level: orchestration by transforming growth factor-β (TGF-β) British Journal of Radiology (2005) Supplement_27, 123-127).

In some embodiments, the compositions described above are used to increase collagen production by skin cells. In some embodiments, the compositions are applied to the skin or wounds in the skin in an effective amount, which is the amount required to increase collagen production in the cells. It is contemplated that by increasing collagen production, the compositions of the present invention enhance or improve wound healing in a subject. It is also contemplated that by increasing collagen production upon topical application, the compositions of the present invention can improve attributes of damaged skin, such as general appearance, suppleness, smoothness, amount of wrinkles, moisture, color, etc. Accordingly, the composition of the present invention find use in increasing the collagen content in skin that has been contacted by the composition so that skin moisture is improved or increased, skin wrinkling is improved or decreased, skin suppleness is improved or increased, skin smoothness is improved or increased, skin tone is improved or increased, skin color is improved or normalized, skin stretch marks are improved, decreased, or eliminated or skin roughness is improved or decreased. In other embodiments, the compositions of the present invention are useful for the prophylaxis or prevention of the foregoing skin conditions.

In some embodiments, the compositions described above are used to increase the proliferation of skin cells, and in particular skin fibroblasts. In some embodiments, the compositions are applied to the skin or wounds in the skin in an effective amount, which is the amount required to increase fibroblast proliferation at the site of application. It is contemplated that by increasing fibroblast proliferation, the compositions of the present invention enhance or improve wound healing in a subject. It is also contemplated that by increasing fibroblast proliferation upon topical application, the compositions of the present invention can improve attributes of damaged skin, such as general appearance, suppleness, smoothness, amount of wrinkles, moisture, color, etc. Accordingly, the composition of the present invention find use in increasing the collagen content in skin that has been contacted by the composition so that skin moisture is improved or increased, skin wrinkling is improved or decreased, skin suppleness is improved or increased, skin smoothness is improved or increased, skin tone is improved or increased, skin color is improved or normalized, skin stretch marks are improved, decreased, or eliminated or skin roughness is improved or decreased.

EXAMPLES

Example 1

Cells and Cell Extracts

NCCIT, Jurkat (clone E6-1) and 293T cells (American Type Culture Collection, Bethesda, Md.) are cultured in RPMI 1640 (Sigma, St. Louis, Mo.) with 10% fetal calf serum (FCS), 2 mM L-glutamine, 1 mM sodium pyruvate and non-essential amino acids (complete RPMI). NIH3T3 Swiss-Albino fibroblasts (American Type Culture Collection) are cultured in Dulbecco's modified Eagle's medium (DMEM; Sigma) with 10% FCS, L-glutamine and 0.1 mM β-mercaptoethanol. Mouse ESCs are isolated from inner cell masses of strain sv129 blastocysts and plated on mouse fibroblast γ-irradiated feeder layers in ESC medium (DMEM, 15% FCS, 0.1 mM β-mercaptoethanol, non-essential amino acids, 1% penicillin/streptomycin) supplemented with 1,000 units/ml (10 ng/ml) of recombinant leukemia inhibitory factor (LIF; Sigma) on gelatin-coated plates. Prior to harvesting for preparing extracts, ESCs are passaged and cultured under feeder-free conditions in RPMI containing 10 ng/ml LIF.

To prepare NCCIT extracts, cells are washed in phosphate buffered saline (PBS) and in cell lysis buffer (100 mM HEPES, pH 8.2, 50 mM NaCl, 5 mM $MgCl_2$, 1 mM dithiothreitol and protease inhibitors), sedimented at 400 g, resuspended in 1 volume of cold cell lysis buffer and incubated for 30-45 min on ice. Cells are sonicated on ice in 200-μl aliquots using a Labsonic-M pulse sonicator fitted with a 3-mm diameter probe (B. Braun Biotech, Melsungen, Germany) until all cells and nuclei are lysed, as judged by microscopy. The lysate is sedimented at 15,000 g for 15 min at 4° C. to pellet the coarse material. The supernatant is aliquoted, frozen in liquid nitrogen and stored. Lysate of 95,583±10,966 NCCIT cells is used to generate extract. ESC extracts (25-30 mg/ml protein) are similarly prepared from LIF-adapted ESC cultures. 293T, Jurkat and NIH3T3 extracts are also prepared as above. If necessary, extracts are diluted with $H_2O$ prior to use to adjust osmolarity to ~300 mOsm.

Example 2

Bulge Hair-Follicle Stem Cells

To isolate the vibrissa follicles, the upper lip containing the vibrissa pad of a subject is cut and its inner surface was exposed. In human individuals, hairs from the scalp or other haired body parts may be used instead of vibrissa. The vibrissa or hair follicles are dissected under a binocular microscope. The vibrissa are plucked from the pad by pulling them gently by the neck with fine forceps. The isolated vibrissae were washed in DMEM-F12 (GIBCO/BRL), containing B-27 (GIBCO/BRL) and 1% penicillin/streptomycin (GIBCO/BRL). All surgical procedures were done under a sterile environment. The vibrissa follicular bulge area contained nestin expressing cells. The cells were isolated by exposure to fluorescent anti-nestin antibodies under fluorescence microscopy. The isolated cells were suspended in 1 ml of DMEM-F12 containing B-27 with 1% methylcellulose (Sigma-Aldrich), and 20 ng·$ml^{-1}$ basic FGF (bFGF) (Chemicon). Cells were cultured in 24-well tissue-culture dishes (Corning) at 37° C. in a 5% $CO_2$/95% air tissue-culture incubator. After 4 weeks, the bulge-area cells form colonies.

Example 3

Ex Vivo Therapy

Cells to be reprogrammed ex vivo are washed in cold PBS and in cold Ca2+- and Mg2+-free Hank's balanced salt solution (HBSS; Invitrogen, Gaithersburg, Md.). Cells are resuspended in aliquots of 100,000 cells/100 μA HBSS, or multiples thereof, placed in 1.5 ml tubes and centrifuged at 120 g for 5 min at 4° C. in a swing-out rotor. Sedimented cells are suspended in 97.7 ml cold HBSS, tubes placed in a H2O bath at 37° C. for 2 min and 2.3 ml SLO (Sigma; 100 mg/ml stock diluted 1:10 in cold HBSS) is added to a final SLO concentration of 230 ng/ml. Samples are incubated horizontally in a $H_2O$ bath for 50 min at 37° C. with occasional agitation and set on ice. Samples are diluted with 200 ml cold HBSS and cells are sedimented at 120 g for 5 min at 4° C. Permeabilization is assessed by monitoring uptake of a 70,000 Mr Texas red-conjugated dextran (Molecular Probes, Eugene, Oreg.; 50 μg/ml) in a separate sample 24 h after resealing and replating the cells. Permeabilization efficiency under these conditions is ~80%.

Following permeabilization, cells to be reprogrammed ex vivo are suspended at 1,000 cells/μl in 100 ml extract (or multiples thereof) containing an ATP-regenerating system (1 mM ATP, 10 mM creatine phosphate, 25 mg/ml creatine kinase; Sigma), 100 μM GTP (Sigma) and 1 mM of each nucleotide triphosphate (NTP; Roche Diagnostics, Mannheim, Germany). The tube containing cells is incubated horizontally for 1 h at 37° C. in a $H_2O$ bath with occasional agitation. To reseal plasma membranes, the extract is diluted with complete RPMI containing 2 mM $CaCl_2$ and antibiotics, and cells are seeded at 100,000 cells per well of a 48-well plate. After 2 h, floating cells are removed and plated cells are cultured in complete RPMI. The reprogrammed cells can be transplanted back into patient.

Example 4

Cream Base for Use with Cell Extracts

Water—78%
Proteins—10%
  e.g., Keratin, Filagrin, and/or Growth factors in trace amounts (μM-mM amounts of EGF, IGF, IGFII, Insulin, Substance P, Defensins, NGF)
Lipids—10%
  Squaline 9%, Aliphaic waxes 12%, Sterol esters 33%, Diol esters 7%, Triglycerides 26%, Free sterols 9%, Other lipids 4%.
Cell extract or egg extract or components of extracts—2%

A cream base made from any combination of lipids and/or proteins and/or water containing cell extracts.

Example 5

Preparation of Fish Egg Extracts

Fresh, unfertilized salmon (*Salmo salar*) eggs harvested from females in reproductive phase (late fall) are kept on ice, and the extract preferably made immediately. It is possible to freeze dry eggs in a cryoprotectant (e.g., 1.5 M 1,2-propanediol and 0.2 M sucrose) without disrupting the egg membrane. Freezing should be gradual (−1° C./min) to −80° C. Eggs should be thawed and kept on ice throughout the extract preparation procedure.

Eggs are washed twice in HBSS or seawater with protease inhibitors (10 ug/ml). The washing solution is removed and the eggs are lysed and homogenized in a pre-chilled Dounce glass-glass homogenizator. The lysate is transferred to Beckman Ultra Clear polyallomer centrifuge tubes (5 ml) while avoiding transfer of egg shells, and centrifugated for 15 min at 15.000 g at 4° C. in a Beckman ultracentrifuge using SW55T1 rotor. Three fractions are thereby obtained; lipid top fraction, cytoplasmic middle fraction, and a bottom fraction containing eggshells and nucleic debris. The cytoplasmic middle fraction is the collected extract. This extract is expected to contain most cytosolic organelles including mitochondria, lysosomes and peroxisomes, should be clear and viscous, and have an orange tint. Protease inhibitors (10 ug/ml stock) are added and extracts are kept at −80° C.

Further fractionation of the cytoplasmic extract is possible. Centrifugation at 100,000 g at 4° C. for 60 minutes yields 2-3 fractions, where the top/middle cytoplasmic fraction contains the cytosol with endoplasmic reticulum, SV and microsomes. The extract pH is measured by litmus paper, protein concentration measured by Bradford assay, and osmolarity measured by osmometer.

Mid-blastula Zebra fish embryos are collected, liquid removed and frozen to −20° C. To prepare the extract, embryos are thawed on ice, lysed and homogenized by Dounce glass-glass homogenizator in a small amount of either HBSS or seawater (preferably less than 50% liquid v/v). The lysate is filtered through a sterile linen cloth and centrifugated at 5,000 g at 4° C. for 20 minutes in a SX4250 rotor using a Beckman X-22R centrifuge. The cytoplasmic extract (supernatant) is collected and protease inhibitors (10 ug/ml) are added. The extract may be Millipore filtered (0.22 um MilliQ sterile filter). The extracts are kept at −80° C. The extract pH is measured by litmus paper, protein concentration measured by Bradford assay, and osmolarity measured by osmometer.

This general procedure is useful for the preparation of extracts from sea urchin, shrimp, fish eggs/roe or frog eggs. Briefly, roe collected from gravid female fish soon after they liberated their eggs in a spawning program (hCG hormone injected (1 ml/kg) at 6 to 8 hours before egg liberation, usually at dawn (2-4 am), or from gravid frogs. Roe/eggs are freeze dried or frozen at −20° C. or used fresh. Roe is collected from different kinds of fish. For sea-urchin, 0.5 M KCl is injected around the mouth to evoke shedding of eggs. The extract is prepared from eggs/roe by crushing (cell cracker or dounce-homogenization) or centrifugation at different speeds to separate cytoplasm with all content, with/without egg-shells (zona pellucida), with/without nucleus/cytosol, with/without organelles, with/without lipids. Further fractionation can be conducted to isolate one or more of mRNA, proteins, small peptides, carbohydrates and lipids. Major components of fatty acids in the roe are oleic acid, linoleic acid, and omega-3 fatty acids.

Upon application of the above protocol for salmon egg extracts, the salmon egg extracts had a surprisingly high protein concentration varying from 100-380 mg/ml, pH between 6.4-6.8, and an osmolarity of approximately 350 mOsm. The extracts were clear and viscous and non-filterable (by 0.45 um MilliQ filter). The protein in the extract precipitated easily upon addition of water or hydrous solutions with low buffering capacity due to the high protein content and low pH. Extracts could be neutralized to pH 7.0 by addition of alkaline (1-3 ul 1M NaOH/ml extract), whereupon dilution in water and hydrous solutions was possible. Zebra-fish extracts had a protein concentration varying from 23-26 mg/ml, pH between 6.4-6.8, and an osmolarity between 80-150 mOsm. The extracts were clear and non-viscous, filterable and diluted readily in water at all dilutions.

Example 6

Toxicity Testing of Extracts

Extracts with low pH and that contain certain substances may be toxic to cells. Toxicity of each batch should be tested on each cell type that is to be reprogrammed. Cells are harvested and washed twice in HBSS. Approximately 100,000 cells are pelleted and resuspended in 100 ul extract and incubated in a waterbath at 37° C. for 1 hour. Dilutions of the extracts may be tested to assess cell survival in extracts of varying protein concentration, pH and osmolarity. Optimally, protein concentration should be more than 25 mg/ml, pH should be close to 7.2, and osmolarity close to 280 mOsm. Cells and extract are incubated in wells with normal media (as suited to cell type chosen) for 24 hours, and the morphology of the cells inspected by microscopy. Cells are harvested, stained, and viable cells counted. If more than 50% of cells are non-viable after culture, the extract is considered toxic.

Upon application of the above protocol, 293T cells were viable for at least 3 weeks after incubation with extracts of salmon eggs and zebra fish embryo with protein concentrations varying from 24-380 mg/ml, at osmolarities between 140-350 and pH 6.9-7.7. At osmolarity below 140 mOsm, the cells died.

Cellular morphology of cells reprogrammed with salmon egg extracts or extracts of zebrafish embryos changed after approx. 3 days. 293T cells become rounder, and some populations of cells start to grow in blastoma like spheres. These changes are persistent, and can be observed until 21 days (experiment terminated), although in certain conditions the changes seem to reverse towards normal 293T morphology after 2 weeks. Upon culture of normal 293T cells with extract added to normal media (RPMI-1640 with 10% FCS and 0.2% extract), similar changes in morphology can be observed as seen for reprogrammed cells cultured in normal media. Additionally, cells cultured with salmon egg extracts in particular have an increased growth rate compared to normal cells. When starving cells (RPMI-1640 with 0.5% FCS), growth rate decreases significantly for non-extract treated cells, and morphology of cells changes slightly. For starved cells grown with extracts (0.2% extract in starvation media), the changes are more pronounced. In this case, most cell populations grow in blastomer like spheres, and the spheres detach from the culture vessel and float in the media, where they keep growing. Interestingly, the deceleration in growth rate is reversed in cells cultured with extract added to the starvation medium.

Example 7

Physical Properties of Extracts

RNA, DNA and protein content of LEX were measured using the Qube-iT fluorimeter from InVitrogen. All extracts measured have yielded comparable effects on collagen secretion from human fibroblasts in vitro at 0.5% stimulation for 8 days. Extracts were diluted in PBS and Qube-iT assay buffer prior to measurements.

RNA Content of Salmon and Trout Homogenates and Extracts Average 2-5 mg/ml.

Homogenates of salmon eggs (non-centrifugated) contain 3-4 mg/ml RNA

After centrifugation to 9-15,000 g, RNA content was reduced to 2-3 mg/ml. This is probably due to RNA being centrifugated down or degraded. Interestingly, trout egg homogenates (non-centrifugated) contain 2-3 mg/ml RNA, but after centrifugation to 9-15,000 g, the concentration of RNA sis increased to 3-5 mg/ml. Extracts made from trout eggs are less viscous than extracts made from salmon eggs, and may keep RNA better in water phase suspension during centrifugation.

DNA Content of Salmon and Trout Homogenates and Extracts Between 40-500 ug/ml.

Homogenates of salmon eggs (non-centrifugated) contain 60-200 ug/ml DNA

After centrifugation to 9-15,000 g, DNA content was reduced to 40-51 ug/ml. This is probably due to DNA being centrifugated down. Interestingly, homogenates of trout eggs (non-centrifugated) contain more DNA than salmon egg extracts: 130-530 ug/ml DNA. After centrifugation to 9-15,000 g, DNA content is reduced to 70-125 ug/ml, but is still higher than comparable salmon egg extracts. Extracts made from trout eggs are less viscous than extracts made from salmon eggs, and may keep DNA in better water phase suspension during centrifugation.

The DNA content varies widely between test-homogenates prepared here, and may be caused by differential lysing of nuclei containing gDNA prior to centrifugation. Better lysing of nuclei by variations on the homogenization process during production may yield extracts with higher DNA content. These differential extracts may yield separate effects useful for different applications, such as effects on gene expression in skin cells.

Protein Content of Salmon and Trout Homogenates and Extracts Average 180-300 mg/ml.

Homogenates of salmon eggs (non-centrifugated) contain 180-260 mg/ml protein. After centrifugation to 9-15,000 g, protein content was unchanged or increased slightly to 200-260 mg/ml. Homogenates of trout eggs (non-centrifugated) contain 250-300 mg/ml protein, and after centrifugation to 9-15,000 g, protein content is roughly the same (250-270 mg/ml). The protein fraction of the egg cytosol is not expected to be spun down at the g-forces applied, and may be expected to be similar to the raw protein content of the egg cytosol.

Previous measurements of protein contents in extracts using a Nano-drop spectrophometer showed a range of 150-250 mg/ml. This may be due to an upper detection limit around 250 mg/ml in the Nano-drop. It is probable that the slightly higher fluorometer measurements presented here are more accurate.

TABLE 1

Summary of measurements RNA, DNA and protein content in extracts

| Source of eggs | Centrifugation speed | LEX/corresp to LEX | mg/ml RNA | μg/ml DNA | mg/ml protein |
|---|---|---|---|---|---|
| Salmon | Homogenate, no centrifugation | LEX 20 | 3.51 | 66.8 | 256 |
| Salmon | 15000 xg | LEX 20 | 2.34 | 44 | 252 |
| Salmon | Homogenate, no centrifugation | LEX 24 | 3.42 | 192.4 | 180 |
| Salmon | 12000 xg | LEX 24 | 2.93 | 50.8 | 208 |
| Trout | Homogenate, no centrifugation | LEX 28 | 2.67 | 131.6 | 249 |
| Trout | 15000 xg | LEX 28 | 3.51 | 73.2 | 249 |
| Trout | Homogenate, no centrifugation | LEX 25 | 2.53 | 528 | 296 |
| Trout | 15000 xg | LEX 25 | 3.70 | 72.8 | 262 |
| Trout | 15000 xg | LEX 25 | 3.63 | 99.2 | 210 |
| Trout | 12000 xg | LEX 31 | 4.59 | 87.2 | 270 |
| Trout | 12000 xg | LEX 32 | 4.68 | 124.8 | — |
| Trout | 12000 xg | LEX 33 | 4.67 | 94.4 | 252 |

Lipid Content of Extracts is 3.7-4.5 g/100 g Extract (3.7-4.5%).

The lipid content of extracts were measured by ALS (Germany), and was found to be in the narrow range of 3.7-4.5 g/100 g in all extracts from salmon or trout roe prepared at centrifugations spanning from 1,700 g to 15,000 g. The lower g-force centrifugations appear to require spinning at room temperature to give equal lipid fractionation to higher g-forces at 4 degrees centigrade. At lower centrifugal forces than 1,700 g also applicable to produce an extract the lipid content may be higher (4-7%). The extract may contain the following lipids (right column), and the lipid fraction removed from the extract during production may include the following lipids (left column)

TABLE 2

Lipid content can vary between batch production and specific lipids can include:

| Report by ALS Scandinavia ELEMENT | SAMPLE | Removed from extract LIPID lipid fract. | % of remaining lipids in extract LEX 42 |
|---|---|---|---|
| Fatty acids, saturated | g/100 g | 22.7 | 1.6 |
| Fatty acids, monounsaturated | g/100 g | 36.6 | 2.8 |
| Fatty acids, polyunsaturated | g/100 g | 44.5 | 0.8 |
| C4:0 Butyric acid | g/100 g | <0.10 | <0.10 |
| C6:0 Caproic acid | g/100 g | <0.10 | <0.10 |
| C8:0 Caprylic acid | g/100 g | <0.10 | 0.25 |
| C10:0 Capric acid | g/100 g | <0.10 | 0.62 |
| C11:0 Undecanoic acid | g/100 g | <0.10 | <0.10 |
| C12:0 Lauric acid | g/100 g | <0.10 | <0.10 |
| C13:0 Tridecanoic acid | g/100 g | <0.10 | <0.10 |
| C14:0 Myristic acid | g/100 g | 3 | 4.2 |
| C14:1 Myristoleic acid | g/100 g | 0.11 | 0.15 |
| C15:0 Pentadecanoic acid | g/100 g | 0.3 | 0.34 |
| C15:1 cis10-Pentadecanoic acid | g/100 g | <0.10 | 0.12 |
| C16:0 Palmitic acid | g/100 g | 11 | 14.3 |
| C16:1 Palmitoleic acid | g/100 g | 7.3 | 9.6 |
| C17:0 Heptadecanoic acid | g/100 g | 0.24 | 0.21 |
| C17:1 Heptadecenoic acid | g/100 g | <0.10 | <0.10 |
| C18:0 Stearic acid | g/100 g | 3.6 | 5.4 |
| C18:1 Oleic acid | g/100 g | 22.9 | 33.8 |
| C18:2 Linoleic acid (omega6) | g/100 g | 6.2 | 5 |
| C18:3 Linolenic acid (omega6) | g/100 g | 0.92 | 0.47 |
| C18:3 a-Linolenic acid (omega3) | g/100 g | 2.4 | <0.10 |

TABLE 2-continued

Lipid content can vary between batch production
and specific lipids can include:

| Report by ALS Scandinavia ELEMENT | SAMPLE | Removed from extract LIPID lipid fract. | % of remaining lipids in extract LEX 42 |
|---|---|---|---|
| C18:4 Stearidonic acid (ome3) | g/100 g | 0.57 | 0.23 |
| C20:0 Arachidic acid | g/100 g | 0.85 | 0.43 |
| C20:1 Eicosenoic acid | g/100 g | 0.83 | 1.1 |
| C20:2 Eicosadienoic acid (om6) | g/100 g | 0.49 | 0.34 |
| C20:3 Eicosatrienoic ac (omega6) | g/100 g | 0.3 | 0.14 |
| C20:4 Arachidonic acid (omega6) | g/100 g | 1.6 | 0.78 |
| C20:5 Eicosapentaenoic ac (ome3) | g/100 g | 9.4 | 2.8 |
| C21:0 Heneicosanoic acid | g/100 g | <0.10 | <0.10 |
| C22:0 Behenic acid | g/100 g | 3.1 | 1.3 |
| C22:1 Erucic acid | g/100 g | <0.10 | <0.10 |
| C22:2 Docosadienoic ac (ome6) | g/100 g | <0.10 | <0.10 |
| C22:5 Docosapentaenoic ac (ome3 | g/100 g | 6.8 | 2.3 |
| C22:6 Docosahexaenoic ac (ome3) | g/100 g | 13.5 | <0.10 |
| C24:0 Lignoceric acid | g/100 g | <0.10 | <0.10 |
| C24:1 Nervonic acid | g/100 g | <0.10 | 2.6 |
| Vanninnhold (water) | g/100 g | | 65.9 |

Nutritional Values, Water Content and Vitamins

Analysis by ALS (Germany) reveal that extracts may contain 60-70% water, 100-200 kcal/100 grams, whereof 20-30 grams are proteins, 1-5 grams are ash, and 0-2% are carbohydrates with sodium content from 0-1 gram/100 grams; and a number of vitamins, including vitamin A and vitamin E.

TABLE 3

| Aske (ash) | g/100 g | 2 |
| Protein | g/100 g | 26.4 |
| Karbohydrater (carbohydrates) | g/100 g | 0.4 |
| Energi (kiloJules) | kJ/100 g | 649 |
| Energi (calories) | kcal/100 g | 154 |
| Kostfiber (fiber) | g/100 g | 0.2 |
| Na (sodium) | g/100 g | 0.22 |
| Fett (fat) | g/100 g | 5.2 |
| Vitamin A | µg/100 g | 10.7 |
| Vitamin E | mg/100 g | 9.9 |

Summary of Physical Properties.

Preparation of extract from homogenates of salmon and trout eggs give differential separation of RNA, DNA and protein, but equal separation of lipids. Fertilized and unfertilized salmon egg extracts display the same profiles of protein, RNA and DNA.

1) The protein concentration (180-300 mg/ml) of the extract is roughly comparable to that of the homogenate (no or little protein removed by production method regardless of g-force).

2) The RNA content (2-5 mg/ml) seems roughly equal for salmon and trout homogenates, slightly lower in trout. RNA seems to be increased in the extracts made from trout egg homogenates, which may be due to the lesser viscosity and better solubility of RNA in the extract fraction from these eggs. RNA content in final salmon egg extracts is slightly lower than that of trout egg extracts.

3) The DNA content (40-500 ug/ml) of the extracts is highly variable, which is probably caused by differential lysing of nuclei in the egg-crushing homogenization process. Salmon egg extracts appear to have lower DNA content than trout egg extracts. In both extracts, and DNA content is lower in extracts than in homogenates, indicating that some DNA is spun down at g-forces over 9.379 g.

4) Total lipid content (3.7-4.5%) is roughly equal for salmon and trout extracts. It seems equal amounts of the lipids are separated from the extract fraction at most g-forces over 1700 g. At lower centrifugal forces which may be use to produce the extract, the total lipid content may be higher, 4-7%.

Example 8

Production of Extracts

It has been documented that lipid content of the extract surprisingly is unchanged at centrifugation speeds varying from 1,700 g to 15,000 g (see above), while other parameters such as RNA, DNA and protein content is altered with the increase of g-force during centrifugation. An extract may also be produced by lower centrifugal forces, down to 400 g, whereupon the content of especially lipids may be higher.

An extra step of washing the eggs for 10 minutes with buffodine (1:100 in 0.9% NaCl) before preparation of homogenate is beneficial. This washing step appears to reduce the bacterial content significantly. For safety reasons, all LEX batches packaged in final containers are mildly pasteurized (incubated) by heating to 56° C. for 20 minutes. This pasteurization sterilizes the extract completely, with 0 bacteria found in extracts plated on bacteria dishes incubated for 3 days at room temperature, 4 degrees centigrade or 30 degrees centigrade. 1 colony/100 ul LEX plated on agar dish incubated at room temperature is the maximum observed. This is 100× below safety limits for drinking water (100 bacteria/ml). A single colony seldom observed probably comes from the air during the plating of LEX, and is comparable to bacterial growth of negative control (plate only).

The stability of LEX and collagen secretion effect is retained after LEX is heated to 56 C for 20 minutes. When applied to human fibroblasts in vitro at 0.5% concentration in cell media for 8 days (media changed daily), the effect on collagen secretion (as measured as efflux of collagen from cells to cell medium and compared to untreated control cells), was comparable to cells treated with unheated extract which had been kept at −80 C after preparation. A 200-400% increase compared to controls was observed for both heated and unheated LEX. Previously we have seen a decreased effect on collagen secretion with extracts incubated at 72 C, indicating that active substances in the extracts which may be denatured between 56 and 72 C are responsible for parts of the secretion effects. In this temperature range, proteins are known to denature. It may be deduced that a structured protein is one of the active substances.

Example 9

Pilot Scale Production

This example describes the preparation of LEX extracts from fresh salmon or trout roe/eggs sent on ice overnight from a hatchery. Eggs that have been in transit on ice >48 hours are discarded. If the eggs can't be prepared on the day of arrival, the eggs may be stored at −20° C. for up to 12 months. The extracts are during lab scale production prepared using an Avanti J-26 XP ultracentrifuge with a JLA 8.1000 rotor and 6×1000 ml tubes (polypropylene, #363678 with liner). For pilot-plant scale production, the homogenate and extract are prepared using a 20 liter Hydropress and a Separator, (OTC 3-03-107 Mineral oil centrifuge respectively.

The day before preparation of extracts, the separator components, glass and stainless steel equipment are autoclaved.

Desired volume of PBS/0.9% NaCl and Buffodine (in 0.9% NaCl) are prepared according to the amount of used roe/eggs. The buffers are placed in a cold room.

Pilot-plant production: On the day of extraction, the hydro-press (20, 40 or 90 liter, Vigo, England) and separator OTC 3-03-107 (Gea Westfalia) are assembled according to the manufacturer's instruction. Silicon tubes are sterilized in 70% Ethanol. A coarse polypropylene press sack is washed once in UV-sterilized water for 1 hour.

The materials and the production procedure are handled at room temperature. Thawed eggs are washed in buffodine for 10 minutes (1-2:100 Buffodine in 0.9% NaCl) and drained. The eggs are rinsed 4× in distilled water containing 0.9% NaCl. Eggs are homogenized (pressed) in the Hydropress using a coarse polypropylene press sack. Homogenate is collected in a sterile beaker after being sieved to remove egg shell and debris. Egg shells and debris are discarded from sieve and Hydropress (all extract trash in biowaste). The homogenate is transferred from the beaker to the separator through silicon tubes (2.4 mm wall thickness with an inner diameter of 8 mm $^5/_{16}$") using a peristaltic pump (Watson Marlow 323 S with Pumphead 314D, VWR International). The homogenate is separated in the separator with an internal pressure of 0.5-2.5 bar (the pressure inside the separator removes the fat fraction of the homogenate and reduces the total fat content in the homogenate from ca 7.2 to ca 4.0-5.5%). The middle (cytoplasmic) fraction is collected in a beaker, and is thereafter transferred to freeze-resistant containers (eppendorf tubes (1 ml aliquots), 8-strip PCR tubes (200 µl aliquots) and 500 ml canisters. If desired, extracts can be pasteurized by heating at 56 degree centigrade for 20 minutes prior to freezing Extract aliquots are frozen immediately at −80° C. and can be stored for up to one year. The extracts have a pH of from 6.5-7.0; have a bacterial load of less <100 colonies per ml (e.g. <10 colonies per plate) as tested on antibiotic-free agar plates; an osmolarity of from 300-500 mOsm; and a protein content of from 100-300 mg/ml.

Extract properties from the lab scale- and pilot plant production are provided in Table 4.

TABLE 4

Extract Properties

| Sample | Lab scale production | Pilet plant production |
|---|---|---|
| Protein (mg/ml) | Nanodrop 192-203 Fluoremeter 163-194 | Nanodrop 194-199 Flouremeter 151-178 |
| DNA (ug/ml) | 14.7 | 17.9 |
| Fat (%) | Homogenate (NA) Lex 36 4.9 | Homogenate 7.2 LEX 37 1 bar 4.9, LEX 37 2 bar 4.8 LEX 37 total 5.0 |
| mOsm | 345-364 | 358-361 |
| pH | 6-7 | 6-7 |
| Collagen effect | 3-6 x fold induction | 4-5.5 x fold induction |
| In test creme | No smell | No smell |

Properties of extract produced in lab scale or pilot plant scale (in red letters). NA indicate—Not Analysed.

Example 10

Extract (LEX) Reverses Age Induced Loss of Collagen by Stimulating Collagen Secretion With age, collagen secretion from skin fibroblast decreases. Studies have shown that the natural secretion of collagen decreases by 38% from age 25 to age 80 ((Varani J. et al. Decreased collagen production in chronologically aged skin: roles of age-dependent alteration in fibroblast function and defective mechanical stimulation. Am J. Pathol. 2006 June; 168(6):1861-8.).

Figure 6:
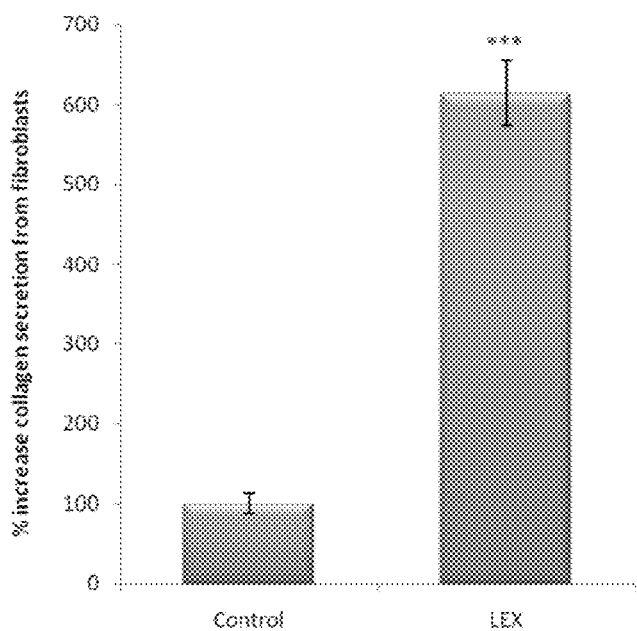
FIG. 6: Collagen secretion from human fibroblasts is increased by 500% in one week in vitro. ***$p<0.001$.

Treating human skin fibroblasts (hSF) for 8 days with 0.5% of the extract in normal cell media increases the collagen secretion from the cells by 500%. See FIG. 6.

Example 11

Extract Treatment Increases the Proliferation of Fibroblasts

Figure 7:
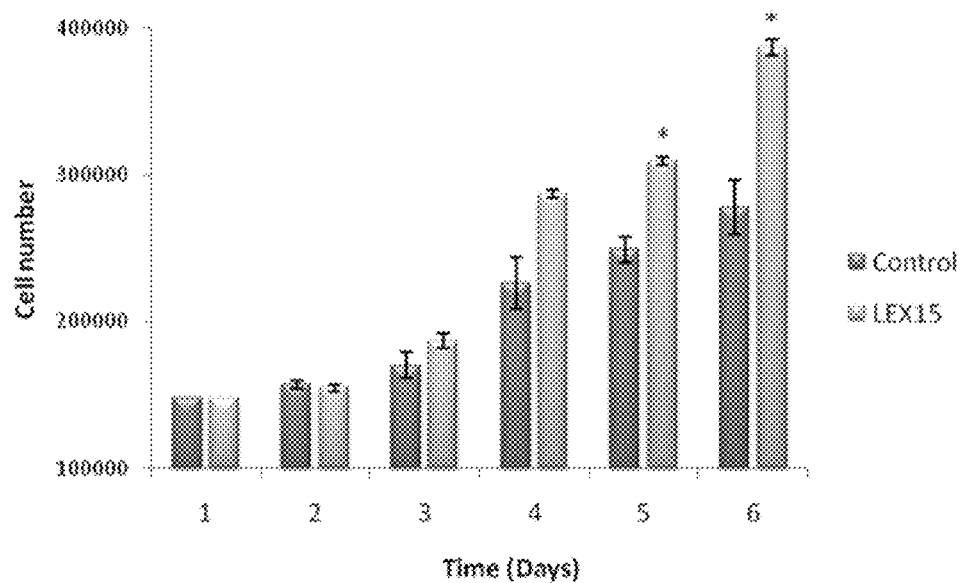
FIG. 7: As the body ages, fewer new cells are produced. LEX can reverse this effect by increasing fibroblast cell number in vitro. *$p<0.05$.

Treatment of human skin fibroblasts (hSF) with 0.5% extract added to normal cell media increases the proliferation of the cells in vitro by 40% in 7 days. See FIG. 7.

Example 12

The Extract Decreases the Appearance of Fine Lines In Vivo

Twenty-two test persons (of Asiatic origin) were divided into 3 groups, the study lasted 56 days, measurements of skin roughness were taken on day 0, 7, 14, 28 and 56. Asian skin usually responds less well to wrinkle reducing treatments than Caucasian or black skin. The significant effect seen with 5% extract in this study may mean a lower % extract may be necessary to have a significant effect in other skin types.

A basic water based serum with 12% glycerol was used a base control (group 3), into which it was added 5% extract (group 1) or 1% extract (group 2).). Test persons applied the appropriate cream daily.

Surface roughness (SA) was measured with from PRIMOS_3D system (Canfield, USA).

Figure 8:
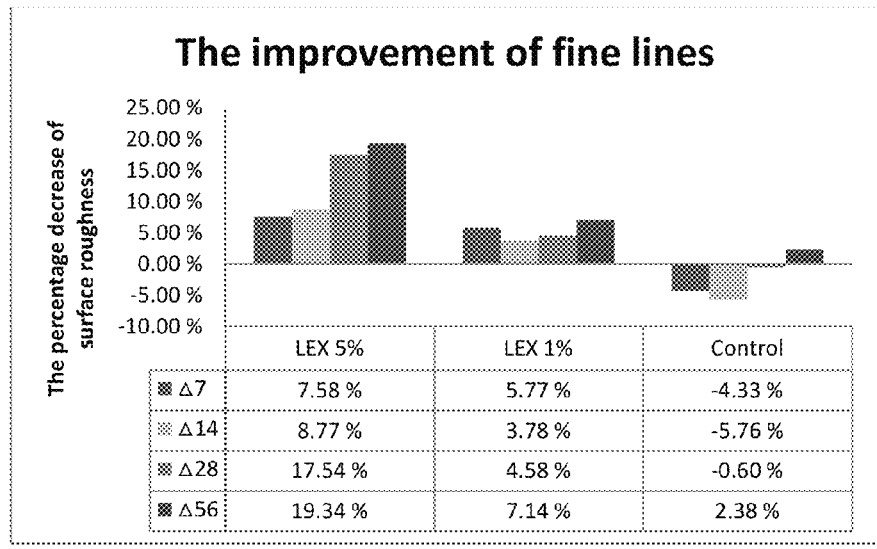
FIG. 8: 5% extract in a serum base gives significant decrease in surface roughness and fine lines over control at day 7, 14 and 28.1% extract has a significant effect over control at day 7. (Average values within groups shown).

5% extract concentration (group 1) decreases the appearance of fine lines by 20% compared to control. The effect is statistically significant. The results for 5% extract shows a significant decrease in surface roughness is significant to control. The dose-response curve show larger improvements over time. This study shows a remarkable, significant effect on the decrease of fine line in only 7 days over control. Significant decrease in fine lines over control (group 3) are found at day 7, 14 and 28. Extract at 1% (group 2) also showed a significant effect over control on day 7. See FIG. 8.

This effect on the reduction of fine lines may be due to an increased production in collagen in the skin and possibly an increase in the number of fibroblasts. Further in vivo studies involving biopsies would need to be conducted to document this. The dose-response curve is in agreement with our in vitro results on fibroblast cells in culture, where collagen secretion increases with time, and is concentration dependent.

However, as with retinoin, not all the volunteers have an effect, even after 56 days. Analyzing the raw data, it appears that for 5% extract, 40% has an extremely good effect, 40% has a moderate effect and 20% has no effect. This can be dependent on age, or the lack of vitamin C or iron, on which the formation of collagen is dependent or genetic factors, or that the test person did not apply the serum as instructed.

According to others studies, only about 45% of women using retinoid-like creams have an improvement after 1 year—the results seen with the extract are thus truly unique. To our knowledge there are no other product tested this way that has such a large and significant improvement in only 28 days as seen here with 5% extract.

Example 13

Extract Gives a Significant Reduction of the Melanin Index in Skin

Twenty-two test persons (of Asiatic origin) were divided into 3 groups, the study lasted 56 days, measurements of skin roughness were taken on day 0, 7, 14, 28 and 56. A basic water based serum with 12% glycerol was used a base control (group 3), into which it was added 5% extract (group 1) or 1% extract (group 2). Test persons applied the appropriate cream daily.

Melanin index (MI) was measured with Mexameter (MX18, Courage+Khazaka, Germany). Measurements were taken at 5 areas of the face: forehead, outer edge of eye, cheekbone, outer edge of mouth and the chin.

The measuring principle for melanin and erythema readings is based on a source of light with three specific wavelengths whose radiation is absorbed by the skin and diffusely reflected. A photo detector analyses the diffuse reflection from the skin. It gives information on microcirculation in the skin and amount of pigmentation.

Increased melanin index is a measure of age spots, uneven skin tone and may be caused by sun exposure and/or aging. A smooth and even skin tone is an important element in the perception of skin and a measure in skin youthfulness.

Statistical analysis show that LEX 5% is significantly better at reducing pigmentation than group 3 (control) at all time points, Group 2 (1% extract) is significant to control at day 7, 14 and 56.

Figure 9:
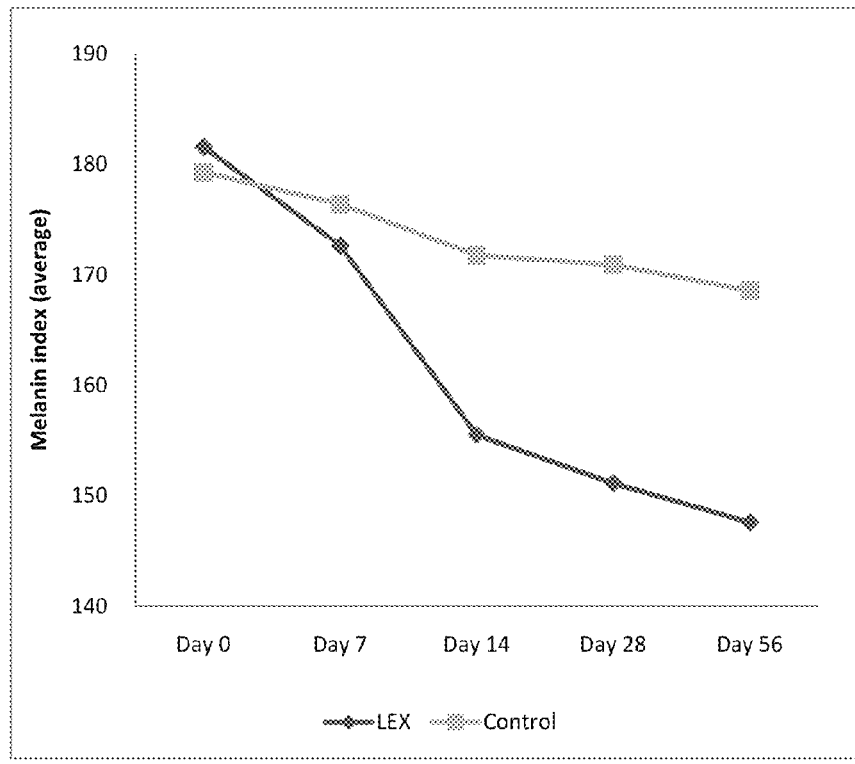
FIG. 9: 5% extract (LEX) is significantly better at reducing melanin in the skin to control.

There is an additional significant increase in the effect between timepoints within Group 1, starting at day 14 significant to day 0 and improving throughout. Day 56 significant to day 0 and day 7. See FIG. 9.

Example 14

Improvement of Erythema Index

Reduced Redness of the Skin

Twenty-two test persons (of Asiatic origin) were divided into 3 groups, the study lasted 56 days, measurements of skin roughness were taken on day 0, 7, 14, 28 and 56.

A basic water based serum with 12% glycerol was used a base control (group 3), into which it was added 5% extract (group 1) or 1% extract (group 2).). Test persons applied the appropriate cream daily.

Erythema index (EI) was measured with Mexameter as with MI, giving a measure of the redness of skin. Measurements were taken at 5 areas of the face: forehead, outer edge of eye, cheekbone, outer edge of mouth and the chin. Red, uneven skintone may be caused by skin irritation or microcirculation becoming visible (varicose veins) in thinning, aging skin.

Figure 10:
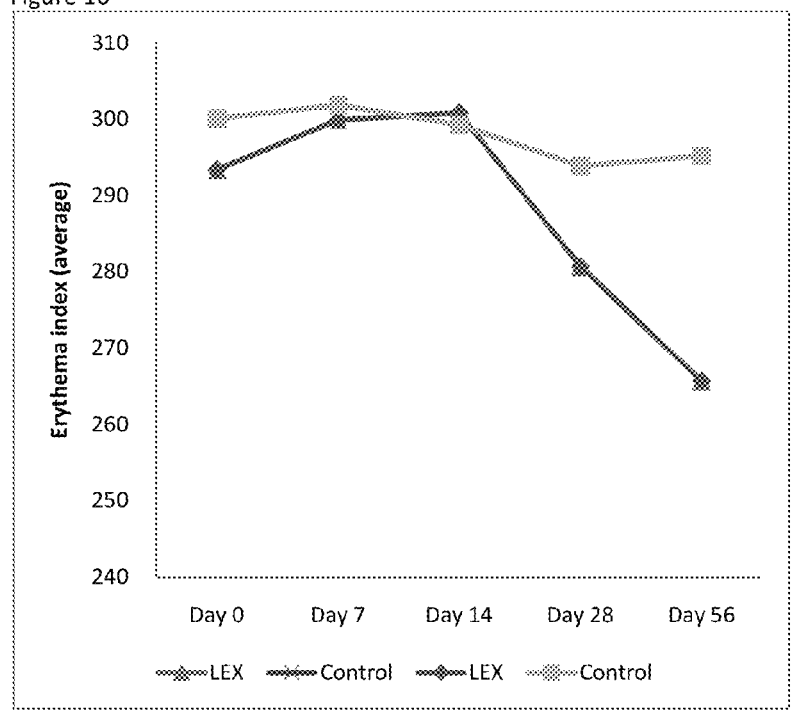
FIG. 10: 5% extract (LEX) is significantly better at reducing redness in the skin to control.

Group 1 (serum with 5% extract) is the only of the only group to have a significant effect. Significant improvement (less redness of skin) is found at day 56 compared to day 0, 7 and 14. See FIG. 10.

Example 15

Improvement in Skin Lucidity, Lightness and Skin Coloration

Twenty-two test persons (of Asiatic origin) were divided into 3 groups, the study lasted 56 days, measurements of skin roughness were taken on day 0, 7, 14, 28 and 56.

A basic water based serum with 12% glycerol was used a base control (group 3), into which it was added 5% extract (group 1) or 1% extract (group 2).). Test persons applied the appropriate cream daily.

L*a*b value measures with a Spectrophotometer (CM2600d, Minolta, Japan), giving a measurement of how light and lucent the skin is Measurements were taken at 5 areas of the face: forehead, outer edge of eye, cheekbone, outer edge of mouth and the chin.

Figure 11:
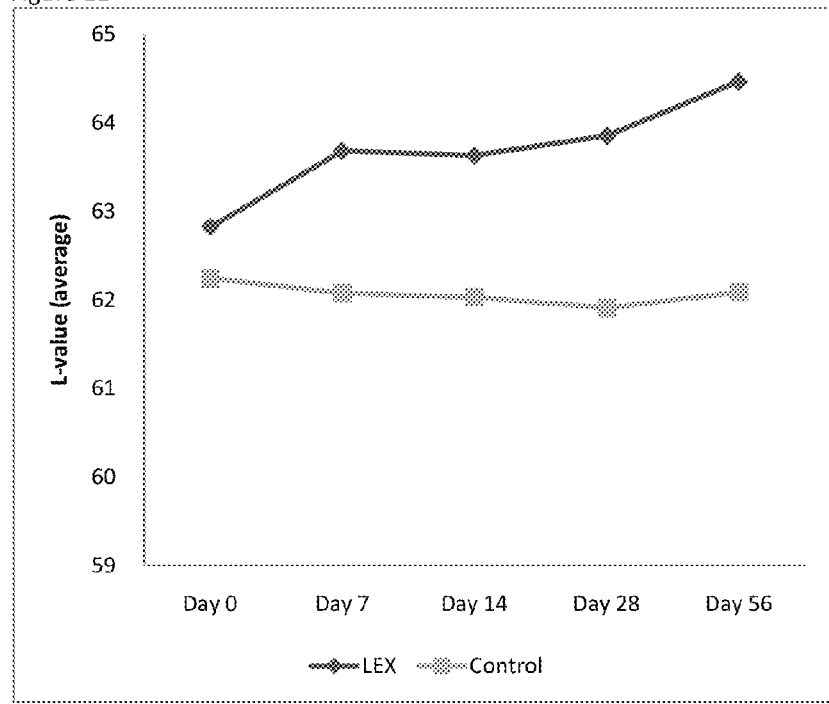
FIG. 11: 5% extract (LEX) is significantly better at improving lucidity (L-value) of the skin to control.

Group 1 (5% extract) gives a significant improvement with increased skin lucidity/lightness. 5% extract gives a significant effect on skin lucidity over all the other groups at day 14.1% extract (not shown) is also significantly better than control on day 7. See FIG. 11.

Example 16

Improvement in Skin Hydration and Skin Water Content and Improvement in Skin Sebum Levels Twenty-two test persons (of Asiatic origin) were divided into 3 groups, the study lasted 56 days, measurements of skin roughness were taken on day 0, 7, 14, 28 and 56.

A basic water based serum with 12% glycerol was used a base control (group 3), into which it was added 5% extract (group 1) or 1% extract (group 2).). Test persons applied the appropriate cream daily.

Measurement of water content in skin by Corneometer (CM825, Courage+Khazaka, Germany). This is an analysis of the moisture retention capacity of the skin, based on the dielectric constant of the water and measured in the superficial layers of the stratum corneum as deep as 10-20 µm to ensure that the measurement is not influenced by capillary blood vessels. Measurements were taken at the cheek area.

Figure 12:
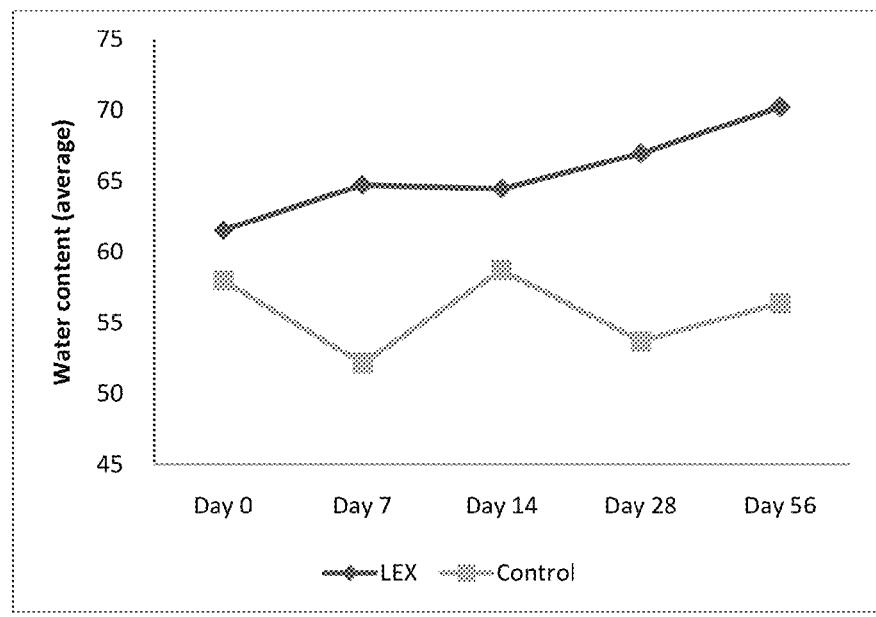
FIG. 12: Water content of the skin is increased significantly by 5% extract compared to control.

Serum with 5% extract (group 1) improves water content in skin significantly better than the other groups at all time points. See FIG. 12.

Figure 13:
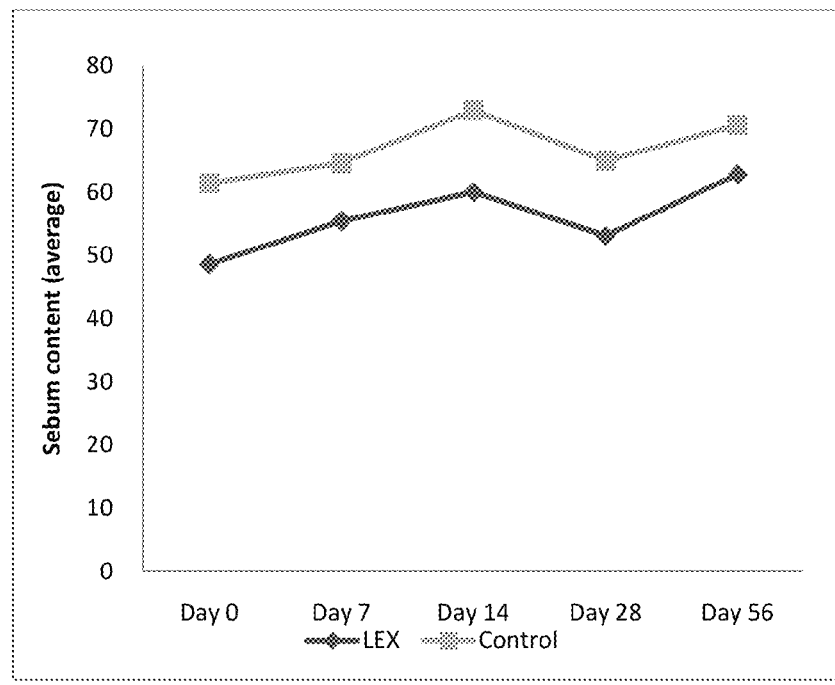
FIG. 13: 5% extract decreases sebum content in the skin compared to control.

Measurements of skin sebum content with Sebumeter (SM810, Courage+Khazaka, Germany) show a decrease in sebum content in the skin, which is beneficial in conditions where skin has excess amounts of sebum. Such a decrease may also indicate that skin has higher water content compared to sebum, which indicates better skin hydration. Measurements were taken at the chin area. See FIG. 13.

Example 17

Evaluating the Melanin Production in Human Epidermal Melanocytes (HEM) after Stimulation with Different Concentrations of LEX Materials:

HEM cells, 25 cm$^2$ culture flasks, LEX 42 (Salmon roe extract), Culture medium: Medium 254 with 1% HMGS and 1% PenStrep, Trypsin-EDTA solution, 1M NaoH with 10% DMSO for cell lysis, Nanodrop for absorbance measurement.

Procedure:

Day zero remove the culture medium of one 175 cm² flask with HEM cell. Add 4 ml of trypsin-EDTA solution until cells are dispersed (1-2 minutes). Add 8 ml culture medium and aspirate cells by gently pipetting up and down. Seed cells in 25 cm² flasks at a density of 7×10^5 per flask. On day one, replace culture media with fresh media supplemented with 0.5%, 1% LEX or normal culture media for control cells. Continue the cultures for seven days, with a media (LEX/Control) change every 24 hours. On day nine, wash the cells with PBS and add 0.5 ml trypsin-EDTA to each 25 cm² flask, count the cells before lysing them in 1M NaOH with 10% DMSO at 80° C. for 2 hours. Spin down the cell debris (13,400 rpm, 10 min) and measure the absorbance of supernatant at 470 nm using the NanoDrop 2000c (Thermo).

Results:

The results showed a decreased proliferation rate in LEX stimulated melanocytes compared to control cells. After eight days of LEX stimulation there were 1.09×10^6 cells per flask treated with 0.5% LEX (33% reduction compared to control), there were 1.12×10^6 cells per flask treated with 1% LEX (32% reduction compared to control), see table 5. The decrease in cell number seen in LEX stimulated cultures demonstrate that LEX reduces the proliferation rate of melanocytes.

Figure 14:
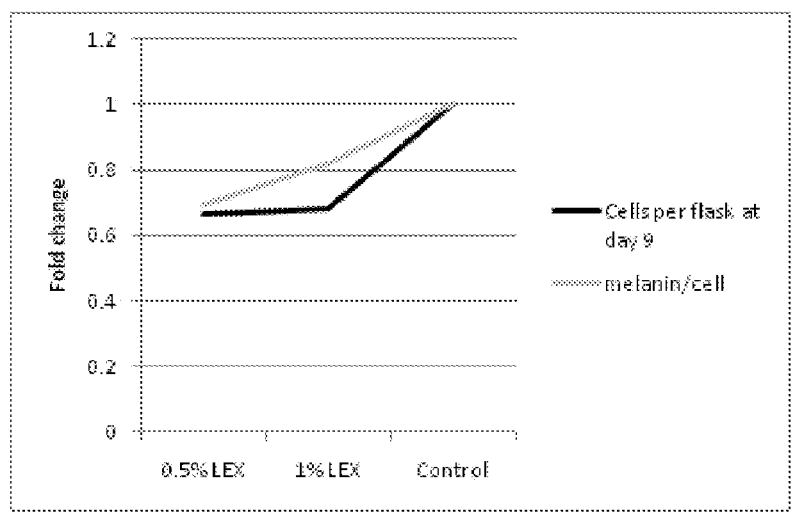
FIG. 14: Fold change in cells per flask from control to LEX stimulated cells and fold change melanin per cell from control to LEX stimulated cells.

The melanin levels were measured for all three conditions after eight days. The results demonstrate that the melanin production in total per flask is lower in the cultures stimulated with LEX compared to control cells, but the numbers of cells were, as mentioned above, also lower in the stimulated cultures than in the control cultures. The melanin content per cell in the cultures treated with 0.5% LEX was 0.7 fold that of control cells, a 30% decrease. For the culture treated with 1% LEX the melanin per cell was 0.82 fold that of the control, an 18% decrease, (following Table and FIG. 14).

These results demonstrate that LEX slows down the proliferation rate of melanocytes, which further leads to a decreased level of melanin produced per cell. In skin this process leads to a lighter skin tone/pigmentation after LEX treatment.

medium, culture medium: DMEM with 10% FBS and 1% PenStrep, starvation medium: DMEM with 1% FBS and 1% PenStrep.

Procedure:

LEX 42 and different concentrations of retinoic acid (0.01M and 0.1M) are applied to fibroblasts (HsF cells) in vitro and collagen production and secretion is measured. Briefly, on day 0, fibroblasts are seeded in 25 cm² cell culture flasks at a density of 2.8×10^5 cells per flask. On day 1, the culture media is replaced with fresh culture media supplemented with 0.5% LEX, 0.01M RA, or 0.1M RA. Control cells are grown with cell culture medium without LEX or RA. The cultures are continued for seven days, with a media (LEX/RA/control) change at day 4. On day 8, the cells are washed 3× with PBS before adding cell culture medium with low serum (1% FBS). On day 9, the culture medium (1.4 ml) is harvested and collagen content assessed using a collagen kit (Biocolor, on the world wide web at biocolor.co.uk/index.php/assay-kits/sircol-1/). The absorbance is measured with Nanodrop 2000c (Thermo).

Figure 15:
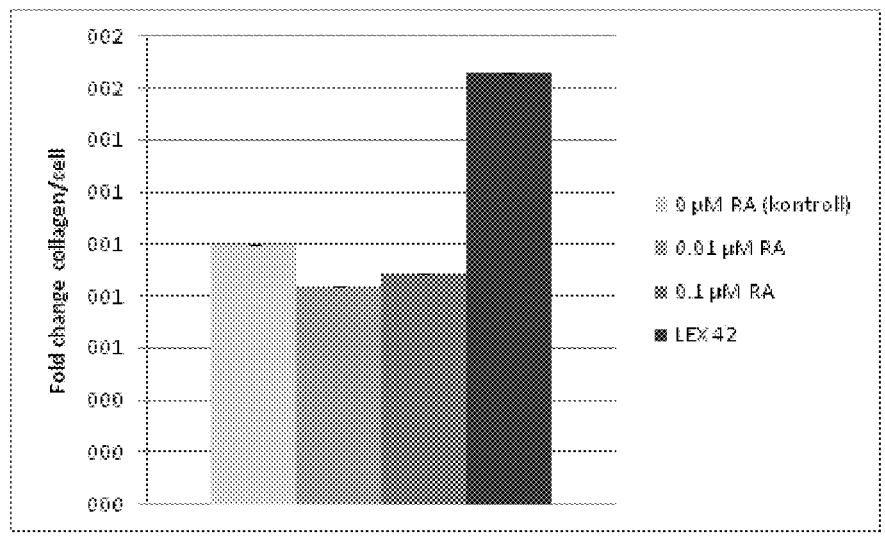
FIG. 15: Comparison of collagen production by retinoic acid and LEX treated cells.
Figure 16:
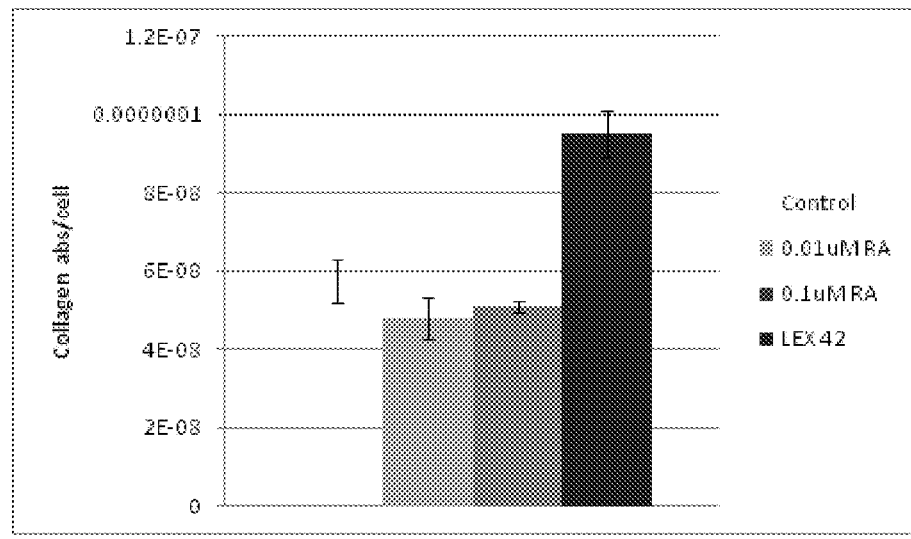
FIG. 16: Comparison of collagen production by retinoic acid and LEX treated cells.
Figure 17:
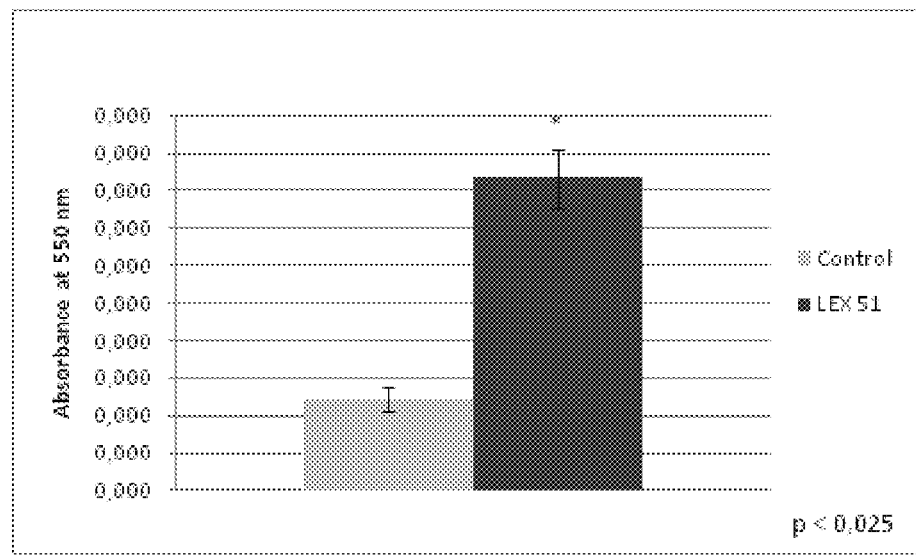
FIG. 17: The absorbance values of collagen present in cell medium from cells stimulated with LEX compared to control cells. The figure shows a 3.42 fold induction of collagen in the medium of LEX stimulated cells (0.167) compared to control cells (0.049), The data are presented as an average (n=3) ±SEM (standard error of the mean).

Results:

After stimulating hsF cells with LEX 42 for eight days a 1.66 fold increase of collagen/cell was found in the stimulated cell medium compared to control. The collagen produced per cell in the RA stimulated cultures showed a decrease compared to LEX stimulated cells and control, the RA cultures showed a 0.84 and 0.89 fold change compared to control cultures, (see following Table, and FIGS. 15 and 16). This corresponds to a 16.5% ($p<0.31$) decrease of collagen produced per cell for the cells stimulated with 0.01M RA, a 11.5% ($p<0.31$) decrease of collagen per cell for the cells stimulated with 0.1M RA and a 65.8 ($p<0.011$) increase for the cells treated with LEX, compared to control.

The result showed a higher proliferation rate in the cultures stimulated with LEX, compared to both control and RA stimulated cells (table 6). LEX stimulated cells showed a 23%

TABLE 5

Overview of cell number, melanin content and melanin per cell after eight days of LEX/control stimulation of melanocytes cells.

| Sample | average final cell # | SEM # of cells | t-test # of cells | abs→µg melanin | Average ng melanin/cell | Fold change | SEM (ng/cell) | T-test (ng/cell) |
|---|---|---|---|---|---|---|---|---|
| 0.5% LEX | 1096030 | 18797 | 2.09642E−05 | 12.09 | 0.0105 | 0.70 | 0.002 | 0.94098677 |
| 0.5% LEX | | | | 7.545 | | | | |
| 0.5% LEX | | | | 14.82 | | | | |
| 1% LEX | 1121900 | 48572 | 0.000497534 | 12.09 | 0.0124 | 0.82 | 0.0006 | 0.018370876 |
| 1% LEX | | | | 15.73 | | | | |
| 1% LEX | | | | 13.91 | | | | |
| Control | 1645410 | 14641 | | 25.73 | 0.0151 | 1.00 | 0.0004 | |
| Control | | | | 24.82 | | | | |
| Control | | | | 23.91 | | | | |

Example 18

Comparing the Effect of Retinoic Acid with LEX Stimulation on Human Skin Fibroblasts In Vitro To compare the in vitro effects of retinoic acid versus LEX on collagen production in human skin fibroblasts.

Materials:

hsF cells, 25 cm² culture flasks, LEX 42 (salmon roe extract), retinoic acid (RA) dissolved in ethanol, 1×PBS at room temperature, Biocolor kit to assay collagen content in increase ($p<0.024$) in cell number after 8 eight days compared to the control cultures. For the 0.1M RA treated cells a 10% ($p<0.5$) increase in cell number, compared to control, was observed, and for the 0.01M RA treated cell only a 3.9% ($p<0.33$) increase in cell number was observed.

These results shows that RA does not induce hsF cells to produce more collagen, which could fill and reduce fine lines/wrinkles, in vitro in the same manner as LEX. No increase in collagen production of hsF cells were seen as a result of stimulation by RA in this experiment.

TABLE 6

Overview of initial and final cell numbers, collagen absorbance values, collagen per cell and percentage change between the treatment regimens LEX, 0.1M RA, 0.01M RA and control cultures.

| Sample | initial # of cells | final # of cells | Collagen Abs | Collagen/cell | Fold induction | Cell % change | Coll/cell % change |
|---|---|---|---|---|---|---|---|
| 3 × 0 µM RA (control) | 280429 | 871667 | 0.050 | 5.73614E−08 | 1.00 | 0 | 0 |
| 3 × 0.01 µM RA | 280429 | 959833 | 0.046 | 4.7925E−08 | 0.84 | 10.1 | −16.5 |
| 3 × 0.1 µM RA | 280429 | 906000 | 0.046 | 5.07726E−08 | 0.89 | 3.9 | −11.5 |
| 3 × LEX 42 | 280429 | 1072333 | 0.102 | 9.51197E−08 | 1.66 | 23.0 | 65.8 |

Example 19

Modification of Collagen Assay to Avoid Overestimation of Collagen Secretion from Fibroblasts Caused by Serum Proteins and LEX Remnants Materials:

hsF cells, 25 cm$^2$ culture flasks, LEX 51 (salmon roe extract), 1×PBS at room temperature, Biocolor kit to assay collagen content in medium, culture medium: DMEM with 10% FBS and 1% PenStrep, starvation medium: DMEM with 1% FBS and 1% PenStrep.

Procedure:

LEX 51 was applied to fibroblasts (HsF cells) in vitro, and collagen production and secretion was assayed. The procedure was as described above, except with the modification of the assay on day 10, were 2 ml of the culture medium is harvested and collagen content assessed using a collagen kit (Biocolor, biocolor.co.uk/index.php/assay-kits/sircol-1/), with the adaptation of isolating collagen from 2 ml of culture medium compared to 1 ml as described in the kit manual. The absorbance is measured at 550 nm (the base line was set to 750 nm) with the Nanodrop 2000 (Thermo)

Results:

The results show a 3.342 fold increase of collagen present in the medium of LEX stimulated cells compared to the control cells. The results show that the fold induction is significant with $p<0.025$ (t-test, tail 2), see table 1. The figure shows a 3.42 fold induction of collagen in the medium of LEX stimulated cells (0.167) compared to control (0.049), the data in FIG. 1 are presented as an average (n=3)±SEM (standard error of the mean) t-test: $p<0.025$.

Example 20

Evaluation of Melanin and Collagen Production in In Vitro Skin Model Including Human Skin Fibroblasts, hsF (ATCC) and Human Epidermal Melanocytes, Hem (Invitrogen)

Materials:

hsF cells, culture flasks (25 cm$^2$), HEM cells, LEX 51 (salmon roe extract), Culture medium for HEM cells (Medium 254 with Human melanocyte Growth Supplement, HMGS (Invitrogen), medium for hsF cells (DMEM with 10% FBS and 1% PenStrep), culture medium for co-culture of both hsF and HEM cells (Medium 254 with 10% FBS and 1% PenStrep), 1×PBS at room temperature, TE to loosen cells from culture flasks, biocolor kit to assay collagen content in medium.

Procedure:

hsF cells are prepared as described above. HEM cells are prepared as described above, and seedHEM cells (200 000/flask) on top of hsF cells. On day two, the culture media is replaced with fresh media supplemented with 0.5% LEX. Control cells were grown in medium without LEX. The culture is continued for seven days, with the media (LEX/control) changed every 24 hours. On day eight, the cells are washed 3× with PBS and medium with low serum is added. On day nine the collagen content of the cell medium is measured by using the sircol collagen assay (Biocolor) and measuring the absorbance against a standard curve of collagen. The level of melanin produced by melanocytes is measured by lysing the cells in 1M NaOH at 80° C. for 2 hours before spinning down the cells at 12,000 rpm, for 10 min (minispin) before measuring the absorbance of the supernatant at 470 nm (Nanodrop 2000c) against a standard curve of melanin.

TABLE 7

Collagen absorbance of hsF cell medium stimulated with LEX 51 and non-stimulated control cells. Triplets of the experiment were run for both stimulated and control cells

| Sample ID | Date and Time | 1 (nm) | 1 (Abs) | abs × 2 ml | Average | Fold Induction | SEM | t-test |
|---|---|---|---|---|---|---|---|---|
| Control | 08.03.2011 14:44:33 | 550 | 0.012 | 0.024 | 0.049 | 1 | 0.006 | |
| Control | 08.03.2011 14:45:14 | 550 | 0.029 | 0.058 | | | | |
| Control | 08.03.2011 14:45:31 | 550 | 0.032 | 0.064 | | | | |
| 51 | 08.03.2011 14:47:29 | 550 | 0.076 | 0.152 | 0.167 | 3.42 | 0.015 | 0.024 |
| 51 | 08.03.2011 14:47:49 | 550 | 0.061 | 0.122 | | | | |
| 51 | 08.03.2011 14:48:08 | 550 | 0.113 | 0.226 | | | | |

Results:

The collagen production in co-culture was similar to what was seen in hsF cells grown in monoculture, see Table below. The comparison was not realistic as the monoculture assay was performed without the isolation and concentration step, making the results from the monoculture assay overestimated, due to serum and LEX proteins present in the medium during the staining procedure.

Figure 18:
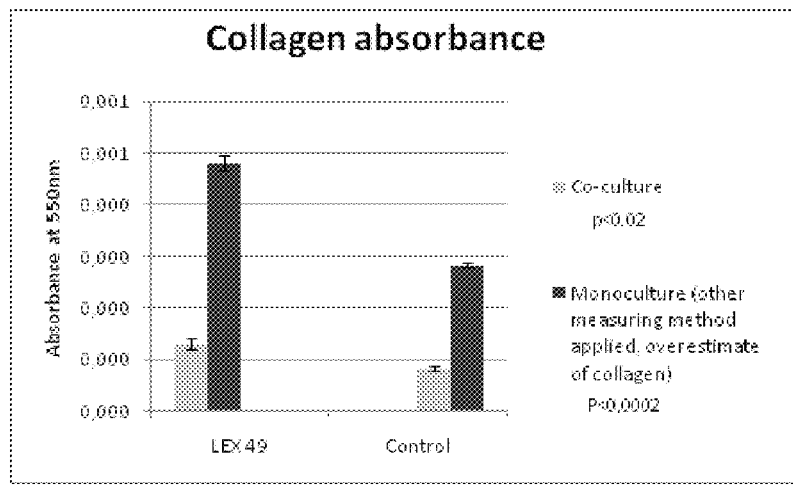
FIG. 18: Collagen absorbance measured for hsF cells both in monoculture (red) and co-culture with HEM cells (blue). Collagen was measured both after LEX stimulation for eight days and for non-stimulated control cells.

LEX stimulation of co-cultured hsF and HEM cells resulted in a higher rate of collagen production/secretion into the medium than for control cells (FIG. 18). A 1.57 (p<0.02) fold increase (Table 8) of collagen in the medium of co-cultured hsF cells was seen. This fold induction was realistic as the collagen is isolated from the background of serum and LEX proteins which is shown to bind the assay dye and contributes to an overestimated collagen level. The collagen levels measured for monocultures of hsF cells stimulated with LEX 49 showed a 1.69 (p>0.0002) fold induction of collagen compared to control, but in this experiment collagen was not isolated from neither LEX nor serum proteins, making the obtained absorbance values an overestimation of collagen present in both stimulated and control medium. These results indicate that co-culturing hsF and HEM cells did not interrupt nor change the hsF cells' ability to increase production of collagen upon LEX stimulation.

Figure 19:
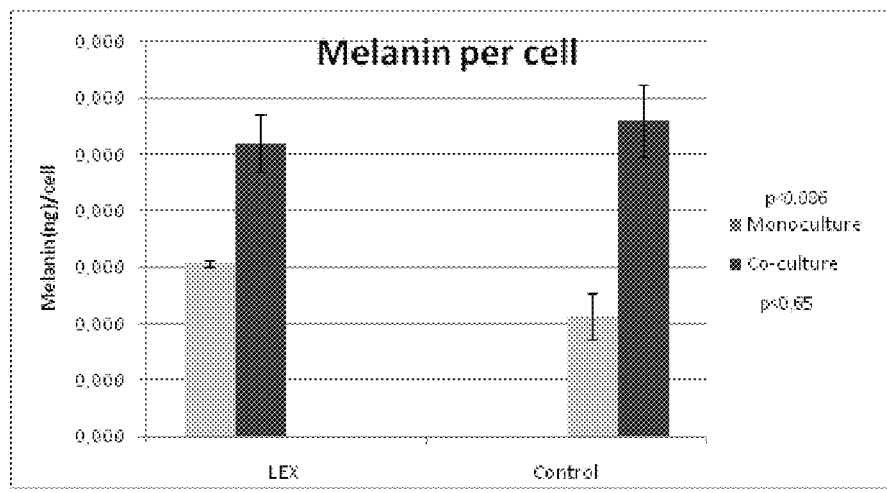
FIG. 19: Melanin levels per melanocyte cell after eight days of hsf-co-culture with or without LEX stimulation.

The level of melanin in the HEM cells was also measured after 8 days of stimulation with LEX 49. When comparing the co-culture melanin levels to melanin measured in melanocytes grown in monoculture, both stimulated and control cells, the results show a higher level of melanin per cell in co-cultured cells than in mono-cultured cells. For the co-cultured HEM cells, 0.028 ng/cell after LEX stimulation and 0.026 ng/cell for control (Table 9, FIG. 19) compared to 0.015 ng/cell in mono-cultured LEX treated cells and 0.011 for non-treated mono-cultured cells. This may demonstrate that melanin production is stimulated/up regulated by factors secreted by fibroblast cells when grown together with HEM cells.

With the co-culture experiment, as seen with mono cultures of melanocytes, LEX affected the proliferation/division of the melanocytes. When stimulating melanocytes with LEX, the cells did not divide as actively as in the control cultures, there were fewer cells after eight days of LEX treatment, 5.87×10^5 cells/flask, compared to 6.99×10^5 cells/flask in the control (table 3). This was also observed for mono-cultured HEM cells, 1.1×10^6 cells per flask compared to 1.64×10^6 cells per flask after eight days. All in all an in vitro model for co-culturing fibroblast and melanocytes has been established, a method that can be used for mimicking the intact skin.

TABLE 9

The level of melanin of the co-cultured melanocytes after 8 days.

| Sample ID | Date and Time | 1 (nm) | 1 (Abs) | abs→µg melanin | Melanin/cell, ng/celle |
|---|---|---|---|---|---|
| Control co-culture | 26.02.2011 10:58:16 | 470 | 0.028 | 23.00 | 0.034 |
| Control co-culture | 26.02.2011 10:58:54 | 470 | 0.024 | 19.36 | 0.027 |
| Control co-culture | 26.02.2011 10:59:21 | 470 | 0.021 | 16.64 | 0.023 |
| LEX co-culture | 26.02.2011 10:59:56 | 470 | 0.017 | 13.00 | 0.023 |
| LEX co-culture | 26.02.2011 11:00:18 | 470 | 0.018 | 13.91 | 0.024 |
| LEX co-culture | 26.02.2011 11:00:37 | 470 | 0.024 | 19.36 | 0.031 |
| Control monoculture | 07.12.2010 | 470 | 0.031 | 25.73 | 0.011 |
| Control monoculture | 07.12.2010 | 470 | 0.030 | 24.82 | 0.007 |
| Control monoculture | 07.12.2010 | 470 | 0.029 | 23.91 | 0.014 |
| LEX monoculture | 07.12.2010 | 470 | 0.016 | 12.09 | 0.016 |
| LEX monoculture | 07.12.2010 | 470 | 0.011 | 7.545 | 0.015 |
| LEX monoculture | 07.12.2010 | 470 | 0.019 | 14.82 | 0.015 |

Example 21

Collagen Production in In Vitro Skin Model Composed of Several Known Skin Cell Types Including Human Skin Fibroblasts, hsF, (ATCC) and Human Epidermal Keratinocytes, HEK and Evaluating the Collagen Production Materials:

hsF cells, culture flasks (25 cm$^2$), HEK cells, LEX 51 (salmon roe extract), Culture medium for HEK cells (Eplife with Human Keratinocyte Growth Supplement, HMGS (Invitrogen), medium for hsF cells (DMEM with 10% FBS and 1% PenStrep), culture medium for co-culture of both hsF and HEK cells (Eplifie with 5% FBS, HKGS and 1% PenStrep), 1×PBS at room temperature, Trypsin-EDTA to loosen cells from culture flasks, Trypsin neutralizer (Invitrogen) and biocolor sircol kit to assay collagen content in medium.

Procedure:

hsF cells were prepared as above and allowed to attach for 24 hours. HEK cells were prepared as described and seeded on top of the hsF cells (200,000 cells/flask). On day two, replace the culture media with fresh co-culture media supplemented with 0.25% LEX. Control cells are grown with cell co-culture medium without LEX). Continue the culture for seven days, with a media (LEX/control) change every 24

TABLE 8

Collagen production of hsF in co-culture with HEM cells and in normal monoculture (below double line).

| Sample ID | Date and Time | 1 (nm) | 1 (Abs) | average absorbance | fold induction | SEM | T-test (p) |
|---|---|---|---|---|---|---|---|
| Control co-culture | 27.02.2011 15:39:43 | 540 | 0.079 | 0.083 | 1 | 0.004 | |
| Control co-culture | 27.02.2011 15:40:01 | 540 | 0.091 | | | | |
| Control co-culture | 27.02.2011 15:40:18 | 540 | 0.079 | | | | |
| LEX 49 co-culture | 27.02.2011 15:40:53 | 540 | 0.109 | 0.131 | 1.57 | 0.012 | 0.0203 |
| LEX 49 co-culture | 27.02.2011 15:41:17 | 540 | 0.132 | | | | |
| LEX 49 co-culture | 27.02.2011 15:41:35 | 540 | 0.151 | | | | |
| LEX 49 | 25.11.2010 13:41:52 | 540 | 0.508 | 0.480 | 1.69 | 0.015 | 0.0002 |
| LEX 49 | 25.11.2010 13:42:14 | 540 | 0.476 | | | | |
| LEX 49 | 25.11.2010 13:42:35 | 540 | 0.457 | | | | |
| Control | 25.11.2010 13:36:41 | 540 | 0.278 | 0.284 | 1.00 | 0.004 | |
| Control | 25.11.2010 13:37:08 | 540 | 0.282 | | | | |
| Control | 25.11.2010 13:37:33 | 540 | 0.291 | | | | | hours. On day eight, wash the cells 3 times with PBS and add medium with low serum. On day nine, assay the collagen content of the cell medium using Sircol collagen assay (Biocolor).

Results: Co-Culture of hsF and HEK Cells

In earlier experiments LEX has been tested on monoculture of HEK cells, resulting in all the cells dying within 2-4 days. The lower the concentration of LEX added to the culture medium, the longer the cells survived. When co-culturing HEK cells with fibroblasts, however, they kept a normal morphology as well as looking healthy while being stimulated with 0.25% LEX for eight days.

The results show that fibroblasts and keratinocytes can be co-cultured in the medium mentioned above, as well LEX is not toxic for keratinocytes when co-cultured with fibroblast cells.

Fibroblasts in co-culture with HEK cells produced collagen at a comparable level to when grown in monoculture (table 4), demonstrating an established model for co-culturing keratinocytes and fibroblasts.

TABLE 10

Collagen concentration of the medium of hsF and HEK cells co-cultured with LEX stimulation for eight days before allowing cells to secrete collagen into medium (low serum, 1%) for 24 hours.

| Sample ID | Date and Time | Collagen concentration (ug) |
|---|---|---|
| co-culture LEX | 24.03.2011 13:55:37 | 6.89 |
| co-culture LEX | 24.03.2011 13:55:58 | 8.85 |
| co-culture LEX | 24.03.2011 13:56:17 | 9.09 |

Example 22

Stem Cell Proliferation Assay

An In Vitro Model Studying the Effect of LEX on Stem Cell Proliferation

Materials:
Cells
 ADSC adipose derived stem cells at passage up to 25
Kit
 Cell proliferation kit XTT, Applichem
Medium and Solutions
 1×PBS, phosphate buffered saline
 DMEM, Dulbecco's modified eagle medium, Sigma
 FBS, Fetal bovine serum, Sigma
 P/S, Penicillin Streptomycin, Sigma
Material
 96 well plates, Corning Costar
 Nanodrop 2000c, Thermo scientific
Methods:

LEX 51 extract prepared as described earlier is applied to adipose-derived stem cells (ADSC) in vitro and proliferation rate is measured and compared to un-stimulated control cells. 5000 ADSC are seeded per well, in 96 well plate. 2 days after seeding the culture media is replaced with (100 µl per well) fresh culture media added 0.1, 0.25, 0.5 and 1.0% LEX. Control cells are cultured with (100 µl per well) cell culture medium without LEX. The cell cultures are added fresh medium every 24 hours (with or without LEX). Proliferation rate is measured at day 3, 6 and 9, using the cell proliferation kit XTT from Applichem. XTT reagent- and activation solution is prepared as described in Applichem product sheet (on the world-wide web at applichem.com/en/shop/product-detail/as/zellproliferations-testkit-xtt/). Three culture wells from control and stimulated cells is analyzed on day 3, 6 and 9. Before measuring absorbance (high absorbance demonstrate high proliferation and vice a versa) each well is washed several times using PBS, to remove excess LEX and FBS. This is because LEX retains the color from the proliferation assay giving overestimated measures. XTT reaction solution (50 µl) is added to each of the wells, the culture plate is afterwards incubated for 8 hours. Shake the plate gently to distribute the dye in each well, 10 µl of the dyed medium is then extracted for analyzing the absorbance. One blank sample is also prepared (100 µl fresh medium and 50 µl XTT reaction solution). The absorbance is then measured using Nanodrop 2000c from Thermo scientific. Wavelengths of 450-500 nm is used to measure, the background with wavelengths of 630-690 nm are subtracted.

Results:

To evaluate the optimal time point for reading the absorbance with the XTT proliferation assay on ADSC cells, an analysis was done. By extracting samples every two hours after adding reagent solution and plotting these against absorbance, an optimal time point for reading was found; after 8 hours. Results from this analysis are shown in FIG. 20.

Figure 20:
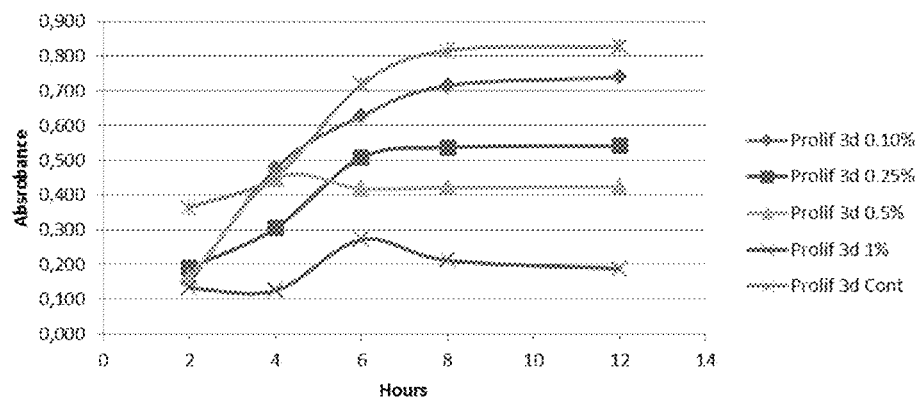
FIG. 20: Absorbance measurements on XTT proliferation assay. ADSC stimulated with 0.1, 0.25, 0.5 and 1% LEX+ ADSC un-stimulated control. Samples stimulated for 3 days and measurements done over 2 to 12 hours.

FIG. 20 show absorbance readings over 2-12 hours with ADSC stimulated and control cells at day 3. Cells stimulated with 0.1%, 0.25%, 0.5% and 1.0%, and control cells were analyzed. It was found during this testing that it is necessary to add a washing step with PBS during the assay to remove LEX and FBS. FIG. 1 show lower proliferation rate with higher LEX concentration stimulation, this was found not to be the case since LEX retained color in the absorbance assay. Values were observed to stabilize after 8 hours of reaction time. Henceforth absorbance reading was done 8 hours after adding XTT reaction solution.

Figure 21:
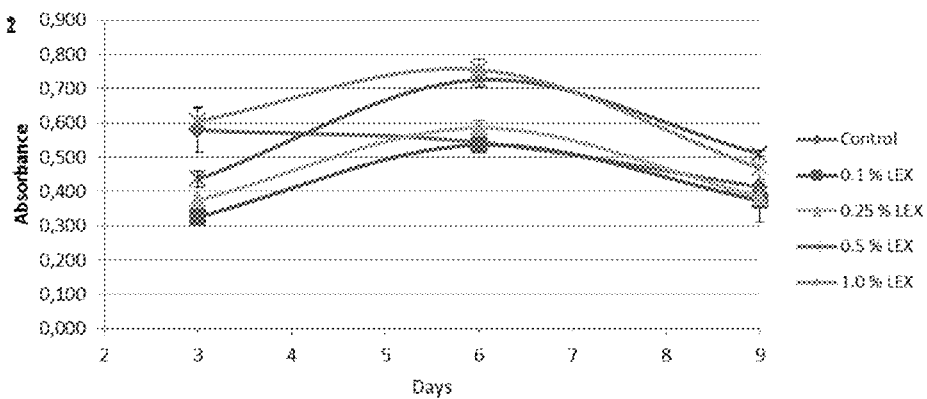
FIG. 21: Absorbance measurements on XTT proliferation assay. ADSC stimulated with 0.1, 0.25, 0.5 and 1% LEX and control using 1% FBS. Samples stimulated for 3 days and measurements done over 8 hours, using baseline 650 nm. *P<0.05 and **P<0.05 for 0.5% and 1.0%

Following this analysis a complete proliferation assay was done as described above but also adding the washing step. The proliferation assay were done both with 1% and 10% FBS to evaluate whether FBS contains signaling molecules that increase the proliferation rate in ADSC. Result from the complete proliferation assay is given in FIG. 21, *P<0.05 and **P<0.05 for 0.5% and 1.0%

Figure 22:
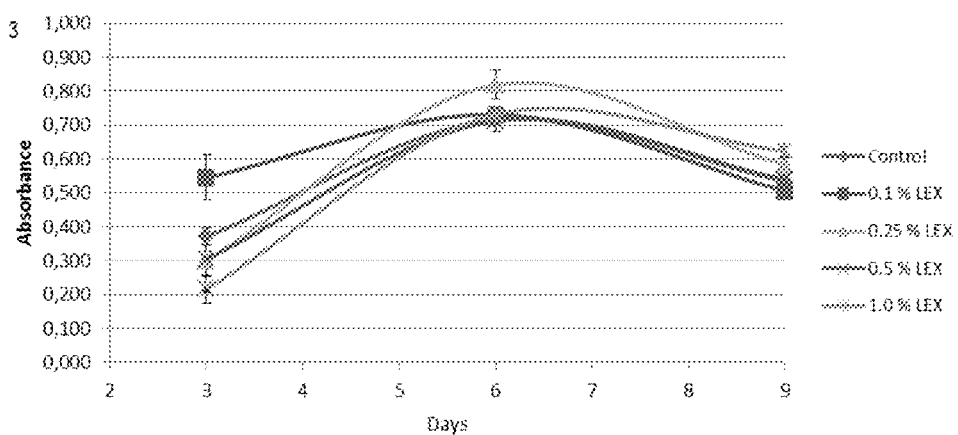
FIG. 22: Absorbance measurements on XTT proliferation assay. ADSC stimulated with 0.1, 0.25, 0.5 and 1% LEX+ ADSC un-stimulated control using 10% FBS. Samples stimulated for 3 days and measurements done over 8 hours, using baseline 650 nm. *P<0.05 and **P<0.05 for 0.1%, 0.25% and 1.0%

Results from proliferation assay using 10% FBS are given in FIG. 22. FIG. 22 show a similar shape as seen with 1% FBS with the highest absorbance at day 6 of stimulation. The values of stimulated samples on day 6 is not significant compared to control. At day 9, the 0.1%, 0.25% and 1.0% LEX stimulated samples are significant compared to un-stimulated samples.**

The proliferation assay results were not unambiguous concerning significant values in 1% FBS and 10% FBS. This would indicate that FBS might affect the proliferation rate in ADSC. Still the general trend of the 3, 6 and 9 days samples was still roughly the same with the highest absorption values after 6 days of stimulation, demonstrating that LEX increase the proliferation rate in ADSC.

Example 23

Microarray Analysis

Micro array data of fibroblasts stimulated 8 days with three different batches of extract (LEX 40, 42, 43) the three different groups are not significant different from each other, confirming that the different batches of the extract produces the same up or down regulation of genes. The micro array data of fibroblasts show up/down regulation of more than 550 genes compared to untreated cells. These genes include but are not limited to several genes previously shown to be involved in the process which is related to wound healing/cell regeneration/cell proliferation. Examples of genes regulated by the extract are; extra cellular matrix proteins like collagen I, III and V; syntases like hyaluronan (HAS2); enzymes like matrix metalloproteinases (MMP3) important for ECM remodeling and members of the kinesin family, important for translating ATP into mechanical work; signaling proteins like interleukin 13 receptor and suppressor of cytokine signaling (SOCS1); proteins important for proliferation like discs, large (Drosophila) homolog-associated protein 5 (DLGAP5) and cyclin A2 (CCNA2)

TABLE 11

Examples of gene regulation in human skin fibroblasts (hSF) after extract treatment

| Symbol | FC | Reg | Biological process |
|---|---|---|---|
| PDK4 | 2.78 | up | Carbohydrate/glucose/pyruvate metabolic process |
| MYBPH | 2.65 | up | cell adhesion, regulation of striated muscle contraction |
| ANGPTL4 | 2.47 | up | Cell differentiation/neg regulation of apoptosis/pos reg of angiogenesis/signal transduction |
| HMOX1 | 2.26 | up | wound healing involved in inflammatory response/anti apoptosis/+++++ |
| PLIN2 | 1.99 | up | Cellular lipid metabolic process/lipid storage |
| CYP26B1 | 1.96 | up | Cell fate determination/neg reg of RA receptor signaling patway/retinoic acid catabolic process |
| FBXL5 | 1.87 | up | Protein ubiquitination |
| FOS | 1.83 | up | Aging, inflammatory response, innate immune resp |
| IL13RA2 | 1.83 | up | cytokine mediated sign pathway/signal transuction |
| SOX18 | 1.79 | up | hair cycle/folllicle development, |
| CDC20 | 1.79 | up | Cell cycle controler/check point |
| THBD | 1.75 | up | Blood coagulation |
| DLGAP5 | 1.76 | up | Cell cycle, proliferation, cell-cells signaling |
| RSPO3 | 1.69 | up | Response to stimulus, wnt receptor signaling patway |
| PLK4 | 1.66 | up | protein phosphorylation |
| CENPM | 1.64 | up | Cell cycle (mitotic) |
| CEP55 | 1.66 | up | Cell division |
| GTSE1 | 1.66 | up | G2 phase of mitotic cycle/DNA damage response induced by p53 resulting in cell cycle arrest |
| MAD2L1 | 1.66 | up | Cell division check point protein |
| CHTF18 | 1.63 | up | Cell cycle/DNA replication |
| CDC25C | 1.67 | up | Cell cycle/division, cell proliferation, DNA replication, regulation of cell cycle |
| PTTG1 | 1.63 | up | Cell cycle/division, negative reg of prolif, reg of cell growth |
| PENK | 1.62 | up | Behavior, nueropeptide sig path, perception of pain |
| TACC3 | 1.61 | up | Cell proliferation, regulation of cell cycle |
| TPX2 | 1.6 | up | Activation of protein kinase acivity, apoptosis, cell cycle/division, |
| KIF4A | 1.61 | up | Axon guidance, blood coagulation |
| KIF20A | 1.6 | up | Microtubule based movement, m phase of mitiotic cycle, protein transport |
| TROAP | 1.58 | up | Cell adhesion |
| ASPM | 1.58 | up | Cell cycle/divsion, negative reg of symmetric division |
| CDCA8 | 1.58 | up | Cell cycle/divsion, |
| HJURP | 1.57 | up | Cell cycle |
| CDC25B | 1.56 | up | Cell cycle/division, pos reg of protein kinase activity |
| FAM83D | 1.57 | up | Cell cycle/division |
| CENPF | 1.55 | up | Cell differentiation, cycle/divsion, proliferation, reg of muscle tissue development, |
| PKMYT1 | 1.57 | up | cell cycle, phosphorylation, kinase activity |
| ANLN | 1.55 | up | Cell cycle, mitosis, |
| SPC24 | 1.54 | up | Cell cycle/division, mitosis |
| DEPDC1 | 1.55 | up | Intracellular signal transduction |
| TYMS | 1.54 | up | Aging, cartilage development, organ regeneration, cell cycle/regulation of transcription, |
| DDIT4L | 1.53 | up | negative regulation of signal transduction |
| TK1 | 1.52 | up | DNA replication, liver development, response to nutrient levels, |
| CENPE | 1.53 | up | microtubule based movement, pos reg of prot kinase activity |
| MELK | 1.51 | up | Protein phosphorylation |
| NCAPG | 1.51 | up | chromosome condensation |
| CCNB1 | 1.49 | up | Cell cycle checkpoint/division |
| PLCXD3 | 1.46 | up | lipid metabolism and intracellular signaling |
| C1QTNF6 | 1.47 | up | |
| CCNF | 1.45 | up | Cell cycle/division |
| RASD2 | 1.43 | up | Signal transduction |
| CDCA3 | 1.44 | up | |
| CCNA2 | 1.43 | up | positive regulation of fibroblast proliferation, cell cycle/divsion |
| KIF18A | 1.42 | up | |
| MMP3 | 1.41 | up | |
| KIF11 | 1.43 | up | |
| KIF14 | 1.41 | up | |
| UCP2 | 1.41 | up | Electron transport chain, response to glucose, fatty acids, hormones/insulin., protein transport |
| SOCS1 | 1.41 | up | signaling patway, fat cell differentiation, regulation of growth |
| RFC3 | 1.41 | up | cell cycle check point, telomere maintenance |
| NCAPD2 | 1.4 | up | cell cycle/division |
| COL1A1 | 1.4 | up | |

TABLE 11-continued

Examples of gene regulation in human skin fibroblasts (hSF) after extract treatment

| Symbol | FC | Reg | Biological process |
| --- | --- | --- | --- |
| ANGPTL4 | 1.42 | up | cell differentiation, lipid metabolism, neg reg of apoptosis, pos reg of angiogenesis |
| NFIL3 | 1.4 | up | immune response |
| CCNB2 | 1.39 | up | cell cycle/division |
| KRT14 | 1.38 | up | epithelial cell differentiation, keratin fillament, epidermis development |
| ITGA3 | 1.38 | up | cell adhesion, blood coagulation |
| FAH | 1.36 | up | amino acid metabolism |
| ITGA5 | 1.36 | up | cell adhesion, blood coagulation, leukocyte migration, WOUND HEALING, pos reg VEGF patway |
| PGF | 1.34 | up | cell cell signaling, angiogenesis, cell division, pos reg proliferation |
| COL3A1 | 1.34 | up | |
| CSPG4 | 1.34 | up | ECM molekyl, angiogenesis, differentiation |
| HMMR | 1.33 | up | migration and transformation of fibroblasts, binds hyaluronic acid |

Example 24

Milling Process

Materials and Methods:

The mill consists of two metal-milling rolls produced by Monster Brewing Hardware. One of the rollers is idle while the other roller is driven by a drive-shaft for drill. These are connected to a holder with adjustment screws for adjusting gap size between the rolls ~0.5 mm to 2 mm. A specially made "hopper" is placed on top of the mill, working as a funnel for containing the roe and directing them directly to the mill. The top length and width are 322 mm and 290 mm, respectively. The lower opening has the dimensions, 147 mm and 18 mm.

Frozen, unfertilized salmon (*Salmo salar*) eggs are thawed at room temperature in Type 1 quality water produced by Milli-Q system. The water used for thawing is added NaCl (1:100 in 0.9%). Thawed eggs is then sieved and washed in Type 1 quality water produced with 0.9% NaCl and 2% buffodine from Evans Vanodine International Plc. Buffodine is an iodine complex fish egg disinfectant. Buffodine is effective against viruses, bacteria and fungi. Roe is washed in buffodine solution for ≥10 minutes. When finished washing, the eggs are cleaned using Type 1 quality water with NaCl (1:100 in 0.9%) and sieved again. During thawing, washing and cleaning steps the eggs is covered with water. About 3-4 kg sieved eggs are then added to the hopper. The drill then runs at a constant, speed (100-150 Rpm) running the rolls to homogenize salmon roe. The homogenate gather in a sieve, retaining the solids (roe shell) while liquid gathers in a food-grade container. The remaining steps of the production procedure are as described earlier.

The mill has been implemented in the production procedure since batch 47.

Results:

The production procedure is now more efficient and retains the same effect on collagen production and secretion from hSF (fibroblast), which is used as an effect control for LEX. The results are seen in Table 2.

Quality Control:

Protein concentration, pH and bacterial content was measured using Nano-drop (ND-1000 Spectrophotometer, Nano-Drop Technologies, Inc.), pH-indicator paper, Merck and Caso agar plates from VWR, respectively. The results from quality control on LEX 47 to 51 are shown in Table 1.

TABLE 12

Quality control on LEX batches 47-51, showing species, preparation method, pH, protein concentration, as well as bacterial content in colony- forming units (CFU).

| Species | Preparation | LEX # correspond to | pH | mg/ml protein | Bacterial content (CFU/ 100 µl) |
| --- | --- | --- | --- | --- | --- |
| Salmon | Malt mill and | LEX 47 | 6.4 | 179 | 1.3 |
| Salmon | separator at 0-0.5 | LEX 48 | 6.4 | 201 | 2.4 |
| Salmon | bar pressure | LEX 49 | 6.4 | 182 | 0.0 |
| Salmon | | LEX 50 | 6.4 | 255 | 0.1 |
| Salmon | | LEX 51 | 6.7 | 369 | 0.0 |

The pH measurements on batch 47 to 51 show little variation and are all within the predetermined acceptable values. The protein concentration is varying between batches going from 179 up to 369 mg/ml. Concerning bacterial content, none of the batches were outside of the predetermined criteria for sale. Showing that heat treatment at 65° C. removes bacteria from the extract.

TABLE 13

Quality control testing on LEX 47-51, showing species, preparation method and fold induction on collagen production and secretion.

| Species | Preparation | LEX # correspond to | Fold induction, collagen production and secretion |
| --- | --- | --- | --- |
| Salmon | Malt mill and separator at | LEX 47 | 3.3 X |
| Salmon | 0-0.5 bar pressure | LEX 48 | 7.8 X |
| Salmon | | LEX 49 | 6.3 X |
| Salmon | | LEX 50 | 3.0 X |
| Salmon | | LEX 51 | 3.9 X |

Collagen assay from Biocolor was used to analyze the effect of LEX on hSF (fibroblast). This assay measures the produced and secreted collagen from hSF (fibroblasts). The measurements from un-stimulated control was compared to LEX stimulated hSF (fibroblasts) and noted as fold induction. All collagen assay measurements from LEX 47-51 are within the predetermined quality specification.

Example 25

Content Analysis on LEX Batches

Fat Content- and Profile Analysis

Under production of LEX, a small fraction of fats remains in the extract. Tests have shown that remaining fats do not compromise the product. To confirm a stabile fat content and fat profile between LEX batches, samples have been analyzed by ALS laboratory Group Norway AS, specializing in analytical chemistry and testing services.

A fat analysis was run to find eventual differences between LEX batches 46 to 48 plus 42, shown in Table 1.

the general uniformity of the batches, an analysis was done using Nanodrop 2000c spectrophotometer. The resulting values have been filled in Table 1.

TABLE 1

Summary of measurements RNA, DNA and protein content in extracts

| Source of eggs | Centrifugation speed | LEX/corresp to LEX | mg/ml RNA | µg/ml DNA | mg/ml protein |
|---|---|---|---|---|---|
| Salmon | Homogenate, no centrifugation | LEX 20 | 3.51 | 66.8 | 256 |
| Salmon | 15000 xg | LEX 20 | 2.34 | 44 | 252 |

TABLE 14

Fat content- and profile analysis of LEX 46, 47, 48 and 42 done by ALS laboratory Group Norway AS

| ELEMENT | SAMPLE | LEX 46 (Hydropress) | LEX 42 (Hydropress) | LEX 47 (Mill) | LEX 48 (Mill) |
|---|---|---|---|---|---|
| Fett | g/100 g | 5.2 | 5.3 | 5.1 | 5.4 |
| Fatty acids, saturated | g/100 g | 1.6 | 1.2 | 1.1 | 1.1 |
| Fatty acids, monounsaturated | g/100 g | 2.8 | 2.6 | 2.7 | 2.8 |
| Fatty acids, polyunsaturated | g/100 g | 0.8 | 1.5 | 1.3 | 1.6 |
| Transfettsyrer | g/100 g |  | 0 | 0 | 0 |
| Sum omega-3 fettsyrer | g/100 g |  | 0.9 | 0.8 | 1 |
| Sum omega-6 fettsyrer | g/100 g |  | 0.5 | 0.5 | 0.6 |
| C4:0 Butyric acid | g/100 g | <0.10 | 0 | 0.042 | 0 |
| C6:0 Caproic acid | g/100 g | <0.10 | 0.044 | 0.061 | 0 |
| C8:0 Caprylic acid | g/100 g | 0.25 | 0.05 | 0.15 | 0.049 |
| C10:0 Capric acid | g/100 g | 0.62 | 0.031 | 0.067 | 0.028 |
| C11:0 Undecanoic acid | g/100 g | <0.10 | 0 | 0.026 | 0 |
| C12:0 Lauric acid | g/100 g | <0.10 | 0.15 | 0.11 | 0.16 |
| C13:0 Tridecanoic acid | g/100 g | <0.10 | 0 | 0.016 | 0 |
| C14:0 Myristic acid | g/100 g | 4.2 | 3.1 | 2.7 | 3 |
| C14:1 Myristoleic acid | g/100 g | 0.15 | 0.046 | 0.047 | 0.046 |
| C15:0 Pentadecanoic acid | g/100 g | 0.34 | 0.33 | 0.3 | 0.31 |
| C15:1 cis10-Pentadecanoic acid | g/100 g | 0.12 | 0 | 0 | 0 |
| C16:0 Palmitic acid | g/100 g | 14.3 | 12.1 | 10.9 | 10.4 |
| C16:1 Palmitoleic acid | g/100 g | 9.6 | 7.6 | 5.7 | 6.7 |
| C17:0 Heptadecanoic acid | g/100 g | 0.21 | 0.29 | 0.28 | 0.27 |
| C17:1 Heptadecenoic acid | g/100 g | <0.10 | 0 | 0 | 0 |
| C18:0 Stearic acid | g/100 g | 5.4 | 5.5 | 4.5 | 3.9 |
| C18:1 Oleic acid | g/100 g | 33.8 | 33.9 | 40 | 37.2 |
| C18:2 Linoleic acid (omega6) | g/100 g | 5 | 6.8 | 9.3 | 8.7 |
| C18:3 Linolenic acid (omega6) | g/100 g | 0.47 | 0.071 | 0.12 | 0.1 |
| C18:3 a-Linolenic acid (omega3) | g/100 g | <0.10 | 2.2 | 2.8 | 2.8 |
| C18:4 Stearidonic acid (ome3) | g/100 g | 0.23 | 0.3 | 0.22 | 0.3 |
| C20:0 Arachidic acid | g/100 g | 0.43 | 0.35 | 0.29 | 0.34 |
| C20:1 Eicosenoic acid | g/100 g | 1.1 | 1.4 | 1.3 | 1.2 |
| C20:2 Eicosadienoic acid (om6) | g/100 g | 0.34 | 0.54 | 0.5 | 0.55 |
| C20:3 Eicosatrienoic ac (omega6) | g/100 g | 0.14 | 0.24 | 0 | 0 |
| C20:4 Arachidonic acid (omega6) | g/100 g | 0.78 | 1 | 0.18 | 0.27 |
| C20:5 Eicosapentaenoic ac (ome3) | g/100 g | 2.8 | 4.8 | 3.5 | 4.5 |
| C21:0 Heneicosanoic acid | g/100 g | <0.10 | 0 | 0 | 0 |
| C22:0 Behenic acid | g/100 g | 1.3 | 0.58 | 0.44 | 0.55 |
| C22:1 Erucic acid | g/100 g | <0.10 | 0.1 | 0.15 | 0.089 |
| C22:2 Docosadienoic ac (ome6) | g/100 g | <0.10 | 0 | 0.0062 | 0 |
| C22:5 Docosapentaenoic ac (ome3) | g/100 g | 2.3 | 3.8 | 2.8 | 3.6 |
| C22:6 Docosahexaenoic ac (ome3) | g/100 g | <0.10 | 4.5 | 3.9 | 4.5 |
| C24:0 Lignoceric acid | g/100 g | <0.10 | 0.11 | 0.13 | 0.073 |
| C24:1 Nervonic acid | g/100 g | 2.6 | 0.18 | 0.14 | 0.11 |

There are individual fatty acids showing differing values in some of the batches, though the analysis shows a general uniformity in the fatty acid content between all batches.

DNA, RNA and Protein Analysis

Salmon roe have been homogenized using several homogenizing methods, which include centrifugation, separator, hydro press and milling. Using these different homogenizing methods it was important to confirm the stability of the product with regard to DNA, RNA and protein content. To confirm TABLE 1-continued Summary of measurements RNA, DNA and protein content in extracts

| Source of eggs | Centrifugation speed | LEX/corresp to LEX | mg/ml RNA | µg/ml DNA | mg/ml protein |
|---|---|---|---|---|---|
| Salmon | Homogenate, no centrifugation | LEX 24 | 3.42 | 192.4 | 180 |
| Salmon | 12000 xg | LEX 24 | 2.93 | 50.8 | 208 |
| Trout | Homogenate, no centrifugation | LEX 28 | 2.67 | 131.6 | 249 |

TABLE 1-continued

Summary of measurements RNA, DNA and protein content in extracts

| Source of eggs | Centrifugation speed | LEX/corresp to LEX | mg/ml RNA | µg/ml DNA | mg/ml protein |
|---|---|---|---|---|---|
| Trout | 15000 xg | LEX 28 | 3.51 | 73.2 | 249 |
| Trout | Homogenate, no centrifugation | LEX 25 | 2.53 | 528 | 296 |
| Trout | 15000 xg | LEX 25 | 3.70 | 72.8 | 262 |
| Trout | 15000 xg | LEX 25 | 3.63 | 99.2 | 210 |
| Trout | 12000 xg | LEX 31 | 4.59 | 87.2 | 270 |
| Trout | 12000 xg | LEX 32 | 4.68 | 124.8 | — |
| Trout | 12000 xg | LEX 33 | 4.67 | 94.4 | 252 |
| Salmon | 12000 xg | LEX 35 | — | — | 192 |
| Salmon | Hydropress/separator | LEX 46 | 4.3 | 5.3 | 213 |
| Salmon | Hydropress/separator | LEX 47 | 3.6 | 4.6 | 179 |
| Salmon | Mill/separator | LEX 48 | 4.1 | 5.1 | 201 |

By comparing DNA and protein content in LEX batches produced with several production methods, values show slight differences between batches and homogenization methods. However, the RNA content decreases dramatically by the use of separator as a production method. Showing that RNA may be precipitated or separated from the extract during the separation step.

What is claimed is:

1. A method of treating a subject comprising:
contacting the skin of said subject with a water soluble, cytoplasmic fraction of salmon eggs in an amount effective to cause one or more effects selected from the group consisting of reduction of fine lines in the skin, normalization of skin color, increasing skin water content and hydration, decreasing or normalizing the amount of sebum in the skin, decreasing production of melanin, increasing collagen protein production, increasing collagen gene expression, increasing adult stem cell proliferation, increasing cellular metabolism of carbohydrates, increasing cellular metabolism of lipids, prevention of apoptosis, increasing angiogenesis, upregulation the cell cycle of cells, increasing angiogenesis, increasing the hair cycle, increasing follicular development, and increasing cell proliferation.

2. The method of claim 1, wherein said normalization of skin color comprises a reduction of skin melanin index.

3. The method of claim 1, wherein said normalization of skin color comprises a reduction of skin erythema index.

4. The method of claim 1, wherein said cellular extract comprises about 100 to 380 mg/ml protein in an aqueous solution; about 0.1 to 10 mg/ml RNA; about 0.1 to 5 mg/ml DNA and 0.1-10% lipids w/w; wherein said composition has an osmolarity of from about 330 to 440 mOsm, a pH of from about 5.0 to 7.7, and density of from about 0.8 to 1.4 g/ml.

5. The method of claim 1, wherein said cellular extract is selected from the group consisting of an extract of an activated fish egg cellular extract and an unactivated fish egg cellular extract.

6. The method of claim 5, wherein said fish egg cellular extract is from a fertilized egg.

7. The method of claim 1, wherein said cellular extract is provided in a cream, gel, emulsion, ointment, spray, powder or lotion.

8. The method of claim 1, wherein said cellular extract is a cytoplasmic extract.

9. The method of claim 1, wherein said wherein said effects are on one or more cell-types associated with the skin.

10. The method of claim 9, wherein said cell type associated with the skin is selected from the group consisting of a keratinocyte, fibroblast, melanocyte, and adipocyte.

11. The method of claim 1, wherein said effect is reduction of fine lines in the skin.

12. The method of claim 1, wherein said effect is normalization of skin color.

13. The method of claim 1, wherein said effect is increasing skin water content and hydration.

14. The method of claim 1, wherein said effect is decreasing or normalizing the amount of sebum in the skin.

15. The method of claim 1, wherein said effect is decreasing production of melanin.

16. The method of claim 1, wherein said effect is increasing collagen protein production.

17. The method of claim 1, wherein said effect is increasing collagen gene expression.

18. The method of claim 1, wherein said effect is increasing adult stem cell proliferation.

19. The method of claim 1, wherein said effect is increasing cellular metabolism of carbohydrates.

20. The method of claim 1, wherein said effect is increasing cellular metabolism of lipids.

21. The method of claim 1, wherein said effect is prevention of apoptosis.

22. The method of claim 1, wherein said effect is increasing angiogenesis.

23. The method of claim 1, wherein said effect is upregulation the cell cycle of cells.

24. The method of claim 1, wherein said effect is increasing the hair cycle.

25. The method of claim 1, wherein said effect is increasing follicular development.

26. The method of claim 1, wherein said effect is increasing cell proliferation.

* * * * *